(12) United States Patent
Griffith et al.

(10) Patent No.: US 9,463,335 B2
(45) Date of Patent: *Oct. 11, 2016

(54) SYSTEM AND METHOD FOR PLANNING AND MONITORING MULTI-DOSE RADIOPHARMACEUTICAL USAGE ON RADIOPHARMACEUTICAL INJECTORS

(71) Applicant: BAYER MEDICAL CARE INC, Indianola, PA (US)

(72) Inventors: Scott R. Griffith, Murrysville, PA (US); James A. Agamaite, Wexford, PA (US); Douglas Descalzi, Pittsburgh, PA (US); Charles Marsh, Cranberry Township, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/826,602

(22) Filed: Aug. 14, 2015

(65) Prior Publication Data

US 2015/0352371 A1    Dec. 10, 2015

Related U.S. Application Data

(63) Continuation of application No. 13/700,266, filed as application No. PCT/US2011/039106 on Jun. 3, 2011, now Pat. No. 9,108,047.

(60) Provisional application No. 61/351,463, filed on Jun. 4, 2010.

(51) Int. Cl.
| | |
|---|---|
| *A61N 5/00* | (2006.01) |
| *A61N 5/10* | (2006.01) |
| *A61B 6/03* | (2006.01) |
| *A61M 3/00* | (2006.01) |
| *G06F 19/00* | (2011.01) |

(52) U.S. Cl.
CPC ............. *A61N 5/1038* (2013.01); *A61B 6/037* (2013.01); *A61M 3/00* (2013.01); *A61N 5/00* (2013.01); *A61N 5/1007* (2013.01); *A61N 5/1031* (2013.01); *G06F 19/3468* (2013.01); *H05K 999/00* (2013.01); *A61N 2005/1021* (2013.01)

(58) Field of Classification Search
CPC ....... A61N 5/00; A61N 5/1007; A61N 5/103
USPC .......................................................... 600/1–8
See application file for complete search history.

(56) References Cited

U.S. PATENT DOCUMENTS

| | | |
|---|---|---|
| 1,988,480 A | 1/1935 | Campkin |
| 2,027,588 A | 1/1936 | Hannon |
| 2,112,160 A | 3/1938 | Johnson |
| 2,584,397 A | 2/1952 | Pitman |
| 2,702,547 A | 2/1955 | Glass |
| 2,761,717 A | 9/1956 | Mahlke |
| 3,051,173 A | 8/1962 | Johnson et al. |
| 3,191,789 A | 6/1965 | Davidson |
| 3,604,417 A | 9/1971 | Stolzenberg |
| 3,623,474 A | 11/1971 | Heilman et al. |
| 3,645,262 A | 2/1972 | Harrigan |
| 3,701,345 A | 10/1972 | Heilman et al. |
| 3,718,138 A | 2/1973 | Alexandrov et al. |
| 3,720,211 A | 3/1973 | Kyrias |
| 3,738,539 A | 6/1973 | Beich |
| 3,752,145 A | 8/1973 | Runnells et al. |
| 3,760,806 A | 9/1973 | Leeper |
| 3,790,804 A | 2/1974 | Hunt |
| 3,796,218 A | 3/1974 | Burke et al. |
| 3,812,843 A | 5/1974 | Wootten et al. |
| 3,908,652 A | 9/1975 | Weissinger |
| 3,964,139 A | 6/1976 | Kleinmann et al. |
| 3,984,695 A | 10/1976 | Collica et al. |
| 3,987,940 A | 10/1976 | Tischlinger |
| 4,006,736 A | 2/1977 | Kranys et al. |
| 4,030,498 A | 6/1977 | Tompkins |
| 4,080,967 A | 3/1978 | O'Leary |
| 4,084,097 A | 4/1978 | Czaplinski et al. |

(Continued)

FOREIGN PATENT DOCUMENTS

| | | |
|---|---|---|
| DE | 2919978 A1 | 11/1980 |
| DE | 4017920 A1 | 12/1991 |

(Continued)

OTHER PUBLICATIONS

Extended European Search Report dated Oct. 12, 2015 from EP 11790483.9.
Brochure for "Angiomat 6000" of Liebel-Farsheim, 2111 E. Galbraith Road, Cincinnati, OH 45215, © 1987.
Brochure for "Angiomat CT" of Liebel-Farsheim, 2111 E. Galbraith Road, Cincinnati, OH 45215, © 1988.
Brochure for "Cordis Lymphography Injector," Cordis Corporation, Miami, FL 33137 (1972).

(Continued)

*Primary Examiner* — John Lacyk
(74) *Attorney, Agent, or Firm* — Joseph L. Kent; David Schramm; James R. Stevenson

(57) ABSTRACT

A method for planning and monitoring radiopharmaceutical usage during a plurality of radiopharmaceutical injection procedures includes: providing a schedule of the plurality of radiopharmaceutical injection procedures to produce a planned patient schedule; based on the planned patient schedule, calculating a multi-dose container configuration for use during the plurality of radiopharmaceutical injection procedures; transferring the planned patient schedule to a radiopharmaceutical fluid delivery system; loading the multi-dose patient configuration into the radiopharmaceutical fluid delivery system; and conducting the plurality of radiopharmaceutical injection procedures based on the planned patient schedule.

18 Claims, 33 Drawing Sheets

(56) References Cited

U.S. PATENT DOCUMENTS

| | | |
|---|---|---|
| 4,092,546 A | 5/1978 | Larrabee |
| 4,155,490 A | 5/1979 | Glenn |
| 4,207,889 A | 6/1980 | Buehring et al. |
| 4,226,236 A | 10/1980 | Genese |
| 4,252,118 A | 2/1981 | Richard et al. |
| 4,278,086 A | 7/1981 | Hodgins et al. |
| 4,307,713 A | 12/1981 | Galkin et al. |
| 4,345,595 A | 8/1982 | Whitney et al. |
| 4,351,332 A | 9/1982 | Whitney et al. |
| 4,356,822 A | 11/1982 | Winstead-Hall |
| 4,401,108 A | 8/1983 | Galkin et al. |
| 4,405,163 A | 9/1983 | Voges et al. |
| 4,405,312 A | 9/1983 | Gross et al. |
| 4,409,488 A | 10/1983 | King |
| 4,409,966 A | 10/1983 | Lambrecht et al. |
| 4,410,108 A | 10/1983 | Minard |
| 4,424,720 A | 1/1984 | Bucchianeri |
| 4,452,251 A | 6/1984 | Heilman |
| 4,453,934 A | 6/1984 | Gaehwiler et al. |
| 4,464,265 A | 8/1984 | Joyner |
| 4,465,472 A | 8/1984 | Urbaniak |
| 4,465,473 A | 8/1984 | Rueegg |
| 4,467,588 A | 8/1984 | Carveth |
| 4,472,403 A | 9/1984 | Trijzelaar et al. |
| 4,475,666 A | 10/1984 | Bilbrey et al. |
| 4,476,381 A | 10/1984 | Rubin |
| 4,493,646 A | 1/1985 | Lacour et al. |
| 4,512,764 A | 4/1985 | Wunsch |
| 4,529,401 A | 7/1985 | Leslie et al. |
| 4,562,829 A | 1/1986 | Bergner |
| 4,563,175 A | 1/1986 | LaFond |
| 4,568,335 A | 2/1986 | Updike et al. |
| 4,573,978 A | 3/1986 | Reilly |
| 4,585,009 A | 4/1986 | Barker et al. |
| 4,585,439 A | 4/1986 | Michel |
| 4,585,941 A | 4/1986 | Bergner |
| 4,604,847 A | 8/1986 | Moulding, Jr. et al. |
| 4,612,010 A | 9/1986 | Hamacher et al. |
| 4,617,016 A | 10/1986 | Blomberg |
| 4,632,123 A | 12/1986 | Govaert et al. |
| 4,636,198 A | 1/1987 | Stade |
| 4,645,073 A | 2/1987 | Homan |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,681,566 A | 7/1987 | Fenton, Jr. et al. |
| 4,685,903 A | 8/1987 | Cable et al. |
| 4,695,271 A | 9/1987 | Goethel |
| 4,697,622 A | 10/1987 | Swift et al. |
| 4,705,509 A | 11/1987 | Stade |
| 4,722,734 A | 2/1988 | Kolln |
| 4,741,732 A | 5/1988 | Crankshaw et al. |
| 4,741,736 A | 5/1988 | Brown |
| 4,744,826 A | 5/1988 | Iijima |
| 4,747,826 A | 5/1988 | Sassano |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,804,847 A | 2/1989 | Uber, III |
| 4,837,110 A | 6/1989 | Kuhlmann et al. |
| 4,838,856 A | 6/1989 | Mulreany et al. |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,853,521 A | 8/1989 | Claeys et al. |
| 4,853,546 A | 8/1989 | Abe et al. |
| 4,854,324 A | 8/1989 | Hirschman et al. |
| 4,857,728 A | 8/1989 | Smith, Jr. |
| 4,869,720 A | 9/1989 | Chernack |
| 4,878,896 A | 11/1989 | Garrison et al. |
| 4,911,695 A | 3/1990 | Lindner |
| 4,925,444 A | 5/1990 | Orkin et al. |
| 4,929,238 A | 5/1990 | Baum |
| 4,936,833 A | 6/1990 | Sams |
| 4,936,841 A | 6/1990 | Aoki et al. |
| 4,943,279 A | 7/1990 | Samiotes et al. |
| 4,966,579 A | 10/1990 | Polaschegg |
| 4,966,601 A | 10/1990 | Draenert |
| 4,968,305 A | 11/1990 | Takahashi et al. |
| 4,969,874 A | 11/1990 | Michel et al. |
| 4,973,309 A | 11/1990 | Sultan |
| 4,978,335 A | 12/1990 | Arthur, III |
| 4,988,337 A | 1/1991 | Ito |
| 4,994,012 A | 2/1991 | Nakayama et al. |
| 5,002,528 A | 3/1991 | Palestrant |
| 5,007,904 A | 4/1991 | Densmore et al. |
| 5,017,191 A | 5/1991 | Yamada et al. |
| 5,033,650 A | 7/1991 | Colin et al. |
| 5,034,004 A | 7/1991 | Crankshaw |
| 5,039,863 A | 8/1991 | Matsuno et al. |
| 5,047,014 A | 9/1991 | Mosebach et al. |
| 5,049,128 A | 9/1991 | Duquette |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,093,079 A | 3/1992 | Bakaitis et al. |
| 5,104,374 A | 4/1992 | Bishko et al. |
| 5,106,379 A | 4/1992 | Leap |
| 5,112,327 A | 5/1992 | Iinuma et al. |
| 5,135,489 A | 8/1992 | Jepson et al. |
| 5,135,507 A | 8/1992 | Haber et al. |
| 5,139,484 A | 8/1992 | Hazon et al. |
| 5,145,083 A | 9/1992 | Takahashi |
| 5,147,311 A | 9/1992 | Pickhard |
| 5,153,827 A | 10/1992 | Coutre et al. |
| 5,188,603 A | 2/1993 | Vaillancourt |
| 5,190,522 A | 3/1993 | Wojcicki et al. |
| 5,207,642 A | 5/1993 | Orkin et al. |
| 5,226,897 A | 7/1993 | Nevens et al. |
| 5,236,416 A | 8/1993 | McDaniel et al. |
| 5,242,403 A | 9/1993 | Falb et al. |
| 5,242,408 A | 9/1993 | Jhuboo et al. |
| 5,254,086 A | 10/1993 | Palmer et al. |
| 5,254,094 A | 10/1993 | Starkey et al. |
| 5,254,101 A | 10/1993 | Trombley, III |
| 5,256,157 A | 10/1993 | Samiotes et al. |
| 5,269,762 A | 12/1993 | Armbruster et al. |
| 5,274,239 A | 12/1993 | Lane et al. |
| 5,275,582 A | 1/1994 | Wimmer |
| 5,279,569 A | 1/1994 | Neer et al. |
| 5,282,792 A | 2/1994 | Imbert |
| 5,288,285 A | 2/1994 | Carter |
| 5,300,031 A | 4/1994 | Neer et al. |
| 5,308,334 A | 5/1994 | Sancoff |
| 5,316,146 A | 5/1994 | Graff |
| 5,317,506 A | 5/1994 | Coutre et al. |
| 5,324,273 A | 6/1994 | Discko, Jr. |
| 5,334,179 A | 8/1994 | Poli et al. |
| 5,338,309 A | 8/1994 | Imbert |
| 5,342,298 A | 8/1994 | Michaels et al. |
| 5,342,346 A | 8/1994 | Honda et al. |
| 5,354,287 A | 10/1994 | Wacks |
| 5,356,375 A | 10/1994 | Higley |
| 5,356,393 A | 10/1994 | Haber et al. |
| 5,360,413 A | 11/1994 | Leason et al. |
| 5,383,858 A | 1/1995 | Reilly et al. |
| 5,415,843 A | 5/1995 | Andersson |
| 5,423,746 A | 6/1995 | Burkett et al. |
| 5,425,716 A | 6/1995 | Kawasaki et al. |
| 5,429,485 A | 7/1995 | Dodge |
| 5,429,602 A | 7/1995 | Hauser |
| 5,429,611 A | 7/1995 | Rait |

(56) References Cited

U.S. PATENT DOCUMENTS

| | | |
|---|---|---|
| 5,431,627 A | 7/1995 | Pastrone et al. |
| 5,433,712 A | 7/1995 | Stiles et al. |
| 5,439,451 A | 8/1995 | Collinson et al. |
| 5,439,452 A | 8/1995 | McCarty |
| 5,445,622 A | 8/1995 | Brown |
| 5,451,211 A | 9/1995 | Neer et al. |
| 5,456,670 A | 10/1995 | Neer et al. |
| 5,472,403 A | 12/1995 | Cornacchia et al. |
| 5,489,931 A | 2/1996 | Shibata et al. |
| 5,492,147 A | 2/1996 | Challender et al. |
| 5,494,036 A | 2/1996 | Uber, III et al. |
| 5,501,674 A | 3/1996 | Trombley, III et al. |
| 5,505,707 A | 4/1996 | Manzie et al. |
| 5,514,071 A | 5/1996 | Sielaff, Jr. et al. |
| 5,520,653 A | 5/1996 | Reilly et al. |
| 5,523,578 A | 6/1996 | Herskovic |
| 5,531,698 A | 7/1996 | Olsen |
| 5,533,981 A | 7/1996 | Mandro et al. |
| 5,535,746 A | 7/1996 | Hoover et al. |
| 5,545,140 A | 8/1996 | Conero et al. |
| 5,562,591 A | 10/1996 | Marchand et al. |
| 5,569,181 A | 10/1996 | Heilman et al. |
| 5,573,515 A | 11/1996 | Wilson et al. |
| 5,611,785 A | 3/1997 | Mito et al. |
| 5,656,035 A | 8/1997 | Avoy |
| 5,658,261 A | 8/1997 | Neer et al. |
| 5,662,612 A | 9/1997 | Niehoff |
| 5,665,074 A | 9/1997 | Kelly |
| 5,681,285 A | 10/1997 | Ford et al. |
| 5,681,286 A | 10/1997 | Niehoff |
| 5,683,367 A | 11/1997 | Jordan et al. |
| 5,685,842 A | 11/1997 | Drivas |
| 5,685,866 A | 11/1997 | Lopez |
| 5,694,686 A | 12/1997 | Lopez |
| 5,733,259 A | 3/1998 | Valcke et al. |
| 5,738,659 A | 4/1998 | Neer et al. |
| 5,739,508 A | 4/1998 | Uber, III |
| 5,741,227 A | 4/1998 | Sealfon |
| 5,741,232 A | 4/1998 | Reilly et al. |
| 5,755,692 A | 5/1998 | Manicom |
| 5,779,675 A | 7/1998 | Reilly et al. |
| 5,782,815 A | 7/1998 | Yanai et al. |
| 5,795,333 A | 8/1998 | Reilly et al. |
| 5,806,519 A | 9/1998 | Evans, III et al. |
| 5,808,203 A | 9/1998 | Nolan, Jr. et al. |
| 5,820,614 A | 10/1998 | Erskine et al. |
| 5,827,219 A | 10/1998 | Uber, III et al. |
| 5,840,026 A | 11/1998 | Uber, III et al. |
| 5,840,058 A | 11/1998 | Ammann et al. |
| 5,840,068 A | 11/1998 | Cartledge |
| 5,843,037 A | 12/1998 | Uber, III |
| 5,865,766 A | 2/1999 | Bonsall et al. |
| 5,865,805 A | 2/1999 | Ziemba |
| 5,873,861 A | 2/1999 | Hitchins et al. |
| 5,882,343 A | 3/1999 | Wilson et al. |
| 5,885,216 A | 3/1999 | Evans, III et al. |
| 5,897,530 A | 4/1999 | Jackson |
| 5,899,885 A | 5/1999 | Reilly et al. |
| 5,911,252 A | 6/1999 | Cassel |
| 5,913,844 A | 6/1999 | Ziemba et al. |
| 5,916,197 A | 6/1999 | Reilly et al. |
| 5,919,167 A | 7/1999 | Mulhauser et al. |
| 5,921,966 A | 7/1999 | Bendek et al. |
| 5,927,351 A | 7/1999 | Zhu et al. |
| 5,928,194 A | 7/1999 | Maget |
| 5,938,636 A | 8/1999 | Kramer et al. |
| 5,938,639 A | 8/1999 | Reilly et al. |
| 5,944,694 A | 8/1999 | Hitchins et al. |
| 5,947,911 A | 9/1999 | Wong et al. |
| 5,947,929 A | 9/1999 | Trull |
| 5,947,935 A | 9/1999 | Rhinehart et al. |
| 5,954,695 A | 9/1999 | Sims et al. |
| 5,954,697 A | 9/1999 | Srisathapat et al. |
| 5,954,700 A | 9/1999 | Kovelman |
| 5,967,983 A | 10/1999 | Ashburn |
| 5,978,445 A | 11/1999 | Schultheiss et al. |
| 5,993,425 A | 11/1999 | Kriesel |
| 5,997,502 A | 12/1999 | Reilly et al. |
| RE36,648 E | 4/2000 | Uber, III et al. |
| 6,048,334 A | 4/2000 | Hirschman et al. |
| 6,048,335 A | 4/2000 | Mayer |
| 6,059,756 A | 5/2000 | Yeh |
| 6,063,052 A | 5/2000 | Uber, III et al. |
| 6,074,359 A | 6/2000 | Keshaviah et al. |
| 6,080,136 A | 6/2000 | Trull et al. |
| 6,083,197 A | 7/2000 | Umbaugh |
| 6,090,064 A | 7/2000 | Reilly et al. |
| 6,096,011 A | 8/2000 | Trombley, III et al. |
| 6,099,502 A | 8/2000 | Duchon et al. |
| 6,149,627 A | 11/2000 | Uber, III |
| 6,162,198 A | 12/2000 | Coffey et al. |
| 6,179,569 B1 | 1/2001 | Kojima et al. |
| 6,180,082 B1 | 1/2001 | Woltering et al. |
| 6,197,000 B1 | 3/2001 | Reilly et al. |
| 6,221,045 B1 | 4/2001 | Duchon et al. |
| 6,237,374 B1 | 5/2001 | Malchow et al. |
| 6,238,374 B1 | 5/2001 | Winkler |
| 6,258,078 B1 | 7/2001 | Thilly |
| 6,306,117 B1 | 10/2001 | Uber, III |
| 6,317,623 B1 | 11/2001 | Griffiths et al. |
| RE37,487 E | 12/2001 | Reilly et al. |
| 6,336,913 B1 | 1/2002 | Spohn et al. |
| 6,339,718 B1 | 1/2002 | Zatezalo et al. |
| 6,344,030 B1 | 2/2002 | Duchon et al. |
| 6,362,472 B1 | 3/2002 | Yarnall et al. |
| 6,397,098 B1 | 5/2002 | Uber, III et al. |
| 6,425,174 B1 | 7/2002 | Reich |
| 6,440,107 B1 | 8/2002 | Trombley, III et al. |
| 6,454,162 B1 | 9/2002 | Teller |
| 6,471,674 B1 | 10/2002 | Emig et al. |
| 6,482,170 B1 | 11/2002 | Andersen |
| 6,520,930 B2 | 2/2003 | Critchlow et al. |
| 6,521,184 B1 | 2/2003 | Edgson et al. |
| 6,542,751 B1 | 4/2003 | Blink et al. |
| 6,547,787 B1 | 4/2003 | Altman et al. |
| 6,569,127 B1 | 5/2003 | Fago et al. |
| 6,572,823 B1 | 6/2003 | Donahue et al. |
| 6,575,930 B1 | 6/2003 | Trombley, III et al. |
| 6,582,407 B1 | 6/2003 | Lo |
| 6,585,684 B1 | 7/2003 | Hughett et al. |
| 6,585,700 B1 | 7/2003 | Trocki et al. |
| 6,586,758 B2 | 7/2003 | Martin |
| 6,589,158 B2 | 7/2003 | Winkler |
| 6,602,488 B1 | 8/2003 | Daghighian |
| 6,614,040 B1 | 9/2003 | Zens |
| 6,620,134 B1 | 9/2003 | Trombley, III et al. |
| 6,632,189 B1 | 10/2003 | Fallen et al. |
| 6,643,537 B1 | 11/2003 | Zatezalo et al. |
| 6,649,829 B2 | 11/2003 | Garber et al. |
| 6,652,489 B2 | 11/2003 | Trocki et al. |
| 6,673,033 B1 | 1/2004 | Sciulli et al. |
| 6,689,091 B2 | 2/2004 | Bui et al. |
| 6,699,219 B2 | 3/2004 | Emig et al. |
| 6,712,786 B2 | 3/2004 | Azzolini |
| 6,743,202 B2 | 6/2004 | Hirschman et al. |
| 6,767,319 B2 | 7/2004 | Reilly et al. |
| 6,773,673 B1 | 8/2004 | Layfield et al. |
| 6,866,654 B2 | 3/2005 | Callan et al. |
| 6,870,175 B2 | 3/2005 | Dell et al. |
| 6,897,374 B2 | 5/2005 | Garber et al. |
| 6,948,522 B2 | 9/2005 | Newbrough et al. |
| 6,958,053 B1 | 10/2005 | Reilly |
| 6,970,735 B2 | 11/2005 | Uber et al. |
| 6,972,001 B2 | 12/2005 | Emig et al. |
| 7,040,856 B2 | 5/2006 | Reich |
| 7,086,133 B2 | 8/2006 | Reich |
| 7,086,431 B2 | 8/2006 | D'Antonio et al. |
| 7,094,216 B2 | 8/2006 | Trombley et al. |
| 7,105,846 B2 | 9/2006 | Eguchi |
| 7,148,806 B2 | 12/2006 | Anttila et al. |
| 7,151,267 B2 | 12/2006 | Lemer |
| 7,163,031 B2 | 1/2007 | Graves et al. |
| 7,169,135 B2 | 1/2007 | Duchon et al. |
| 7,180,069 B2 | 2/2007 | Motomura et al. |

(56) References Cited

U.S. PATENT DOCUMENTS

| | | |
|---|---|---|
| 7,191,777 B2 | 3/2007 | Brand et al. |
| 7,198,172 B2 | 4/2007 | Harvey et al. |
| 7,268,359 B2 | 9/2007 | Fu et al. |
| 7,335,902 B2 | 2/2008 | Soundararajan |
| 7,419,478 B1 | 9/2008 | Reilly et al. |
| 7,552,746 B2 | 6/2009 | Shin et al. |
| 7,553,294 B2 | 6/2009 | Lazzaro et al. |
| 7,618,397 B2 | 11/2009 | Hicks |
| 7,666,169 B2 | 2/2010 | Cowan et al. |
| 7,694,610 B2 | 4/2010 | Flores et al. |
| 7,712,491 B2 | 5/2010 | Tochon-Danguy et al. |
| 7,713,231 B2 | 5/2010 | Wulfman et al. |
| 7,713,235 B2 | 5/2010 | Torrance et al. |
| 7,713,239 B2 | 5/2010 | Uber et al. |
| 7,734,331 B2 | 6/2010 | Dhawale et al. |
| 7,772,565 B2 | 8/2010 | Wilson |
| 7,887,513 B2 | 2/2011 | Nemoto et al. |
| 7,975,733 B2 | 7/2011 | Horppu et al. |
| 8,071,959 B2 | 12/2011 | Dekemp |
| 8,198,599 B2 | 6/2012 | Bouton et al. |
| 8,415,581 B2 | 4/2013 | Ukai et al. |
| 8,475,404 B2 | 7/2013 | Foshee et al. |
| 8,517,905 B2 | 8/2013 | Buck et al. |
| 8,852,071 B2 | 10/2014 | Buck et al. |
| 9,108,047 B2 * | 8/2015 | Agamaite ............ A61N 5/1007 |
| 2001/0009904 A1 | 7/2001 | Wolff et al. |
| 2001/0009994 A1 | 7/2001 | Small et al. |
| 2002/0128606 A1 | 9/2002 | Cowan et al. |
| 2002/0147429 A1 | 10/2002 | Cowan et al. |
| 2002/0168317 A1 | 11/2002 | Daighighian et al. |
| 2002/0188259 A1 | 12/2002 | Hickle et al. |
| 2003/0014035 A1 | 1/2003 | Trombley et al. |
| 2003/0036674 A1 | 2/2003 | Bouton |
| 2003/0036713 A1 | 2/2003 | Bouton et al. |
| 2003/0065287 A1 | 4/2003 | Spohn et al. |
| 2003/0175196 A1 | 9/2003 | Blackwell et al. |
| 2003/0212707 A1 | 11/2003 | Uber et al. |
| 2003/0216609 A1 | 11/2003 | Dell et al. |
| 2003/0222228 A1 | 12/2003 | Chen et al. |
| 2004/0015038 A1 | 1/2004 | Lemer |
| 2004/0054248 A1 | 3/2004 | Kimchy et al. |
| 2004/0064041 A1 | 4/2004 | Lazzaro et al. |
| 2004/0064101 A1 | 4/2004 | Kowan et al. |
| 2004/0073177 A1 | 4/2004 | Hickle |
| 2004/0073189 A1 | 4/2004 | Wyatt et al. |
| 2004/0082918 A1 | 4/2004 | Evans et al. |
| 2004/0086437 A1 | 5/2004 | Jackson |
| 2004/0092905 A1 | 5/2004 | Azzolini |
| 2004/0133162 A1 | 7/2004 | Trocki et al. |
| 2004/0162515 A1 | 8/2004 | Chornenky et al. |
| 2004/0176676 A1 | 9/2004 | Graw |
| 2004/0205343 A1 | 10/2004 | Forth et al. |
| 2004/0254525 A1 | 12/2004 | Uber et al. |
| 2004/0254533 A1 | 12/2004 | Schriver et al. |
| 2004/0258615 A1 | 12/2004 | Buchanan et al. |
| 2004/0260143 A1 | 12/2004 | Reilly et al. |
| 2004/0260242 A1 | 12/2004 | Hughes et al. |
| 2005/0027196 A1 * | 2/2005 | Fitzgerald ............ A61N 5/103 600/436 |
| 2005/0029465 A1 | 2/2005 | Lemer |
| 2005/0033238 A1 | 2/2005 | Cope et al. |
| 2005/0085682 A1 | 4/2005 | Sasaki et al. |
| 2005/0107698 A1 | 5/2005 | Powers et al. |
| 2005/0129170 A1 | 6/2005 | Watson et al. |
| 2005/0199647 A1 | 9/2005 | Muto et al. |
| 2005/0203329 A1 | 9/2005 | Muto et al. |
| 2005/0203330 A1 | 9/2005 | Muto et al. |
| 2005/0226776 A1 | 10/2005 | Brady et al. |
| 2005/0232387 A1 | 10/2005 | Padgett et al. |
| 2005/0234424 A1 | 10/2005 | Besing et al. |
| 2005/0238576 A1 | 10/2005 | Dell et al. |
| 2005/0247893 A1 | 11/2005 | Fu et al. |
| 2005/0277833 A1 | 12/2005 | Williams, Jr. |
| 2005/0277873 A1 | 12/2005 | Stewart et al. |
| 2005/0277890 A1 | 12/2005 | Stewart et al. |
| 2006/0004243 A1 | 1/2006 | Shimizu et al. |
| 2006/0073048 A1 | 4/2006 | Malackowski |
| 2006/0089604 A1 | 4/2006 | Guerrero |
| 2006/0100578 A1 | 5/2006 | Lieberman |
| 2006/0106345 A1 | 5/2006 | Flaker et al. |
| 2006/0135843 A1 | 6/2006 | Heath |
| 2006/0151048 A1 | 7/2006 | Tochon-Danguy et al. |
| 2006/0195045 A1 | 8/2006 | Gable et al. |
| 2006/0211989 A1 | 9/2006 | Rhinehart et al. |
| 2006/0293553 A1 | 12/2006 | Polsinelli et al. |
| 2007/0034537 A1 | 2/2007 | Fago et al. |
| 2007/0060898 A1 | 3/2007 | Shaughnessy et al. |
| 2007/0088252 A1 | 4/2007 | Pestotnik et al. |
| 2007/0191690 A1 | 8/2007 | Hasse et al. |
| 2008/0038839 A1 | 2/2008 | Linder et al. |
| 2008/0131362 A1 | 6/2008 | Rousso et al. |
| 2008/0161634 A1 | 7/2008 | Nemoto et al. |
| 2008/0166292 A1 | 7/2008 | Levin et al. |
| 2008/0177126 A1 | 7/2008 | Tate et al. |
| 2008/0200747 A1 | 8/2008 | Wagner et al. |
| 2008/0242915 A1 | 10/2008 | Jackson et al. |
| 2009/0116616 A1 | 5/2009 | Lu et al. |
| 2009/0131862 A1 | 5/2009 | Buck et al. |
| 2009/0149744 A1 | 6/2009 | Nemoto et al. |
| 2009/0177050 A1 | 7/2009 | Griffiths et al. |
| 2009/0257949 A1 | 10/2009 | Hefti et al. |
| 2009/0312695 A1 | 12/2009 | Wilson et al. |
| 2010/0030181 A1 | 2/2010 | Helle et al. |
| 2010/0160889 A1 | 6/2010 | Smith et al. |
| 2010/0185040 A1 | 7/2010 | Uber, III et al. |
| 2011/0076317 A1 | 3/2011 | Alessi et al. |
| 2011/0152679 A1 | 6/2011 | Morag |
| 2011/0178359 A1 | 7/2011 | Hirschman et al. |
| 2011/0201867 A1 | 8/2011 | Wagner |
| 2011/0209764 A1 | 9/2011 | Uber et al. |
| 2011/0214781 A1 | 9/2011 | Horppu et al. |
| 2012/0074330 A1 | 3/2012 | Bouton et al. |
| 2012/0226447 A1 | 9/2012 | Nelson et al. |
| 2013/0123567 A1 | 5/2013 | Agamaite et al. |
| 2013/0194080 A1 | 8/2013 | Bowden et al. |

FOREIGN PATENT DOCUMENTS

| | | |
|---|---|---|
| DE | 19601214 A1 | 8/1996 |
| DE | 19633530 A1 | 2/1998 |
| EP | 0160303 A2 | 11/1985 |
| EP | 0164904 A2 | 12/1985 |
| EP | 0320168 A1 | 6/1989 |
| EP | 0323321 A1 | 7/1989 |
| EP | 0333276 A1 | 9/1989 |
| EP | 0346950 A2 | 12/1989 |
| EP | 0364010 A2 | 4/1990 |
| EP | 0379177 A1 | 7/1990 |
| EP | 0384657 A1 | 8/1990 |
| EP | 0482677 A1 | 4/1992 |
| EP | 0486283 A2 | 5/1992 |
| EP | 0523343 A1 | 1/1993 |
| EP | 0567944 A1 | 11/1993 |
| EP | 0584531 A2 | 3/1994 |
| EP | 0736306 A1 | 10/1996 |
| EP | 0749757 A2 | 12/1996 |
| EP | 0795342 A2 | 9/1997 |
| EP | 0900573 A2 | 3/1999 |
| EP | 0915760 A2 | 5/1999 |
| EP | 0919251 A2 | 6/1999 |
| EP | 1616587 A1 | 1/2006 |
| EP | 1723977 A1 | 11/2006 |
| EP | 1927996 A2 | 6/2008 |
| GB | 847914 A | 9/1960 |
| GB | 1380873 A | 1/1975 |
| GB | 2108852 A | 5/1983 |
| GB | 2228168 A | 8/1990 |
| GB | 2299162 A | 9/1996 |
| JP | H06312009 A | 11/1994 |
| JP | H06345133 A | 12/1994 |
| JP | H0811907 A | 1/1996 |
| JP | 2000167053 A | 6/2000 |
| JP | 2000350783 A | 12/2000 |
| JP | 2002021007 A | 1/2002 |

(56) References Cited

FOREIGN PATENT DOCUMENTS

| | | |
|---|---|---|
| JP | 2002341040 A | 11/2002 |
| JP | 2004353875 A | 12/2004 |
| JP | 2005024291 A | 1/2005 |
| JP | 2005040197 A | 2/2005 |
| JP | 2005230366 A | 9/2005 |
| JP | 2005283431 A | 10/2005 |
| JP | 2005324007 A | 11/2005 |
| JP | 2006003223 A | 1/2006 |
| JP | 2006015055 A | 1/2006 |
| JP | 2006017660 A | 1/2006 |
| JP | 2006034845 A | 2/2006 |
| JP | 2006132984 A | 5/2006 |
| JP | 2006133139 A | 5/2006 |
| JP | 2006325826 A | 12/2006 |
| JP | 2006325827 A | 12/2006 |
| JP | 2008-23346 | 2/2008 |
| JP | 2008023346 A | 2/2008 |
| JP | 2008-136786 | 6/2008 |
| JP | 2008136786 A | 6/2008 |
| WO | 8002376 A1 | 11/1980 |
| WO | 8500292 A1 | 1/1985 |
| WO | 8502256 A1 | 5/1985 |
| WO | 8909071 A1 | 10/1989 |
| WO | 8911310 A1 | 11/1989 |
| WO | 9001962 A1 | 3/1990 |
| WO | 9104759 A1 | 4/1991 |
| WO | 9221391 A1 | 12/1992 |
| WO | 9310834 A1 | 6/1993 |
| WO | 9425089 A1 | 11/1994 |
| WO | 9632887 A1 | 10/1996 |
| WO | 9632975 A1 | 10/1996 |
| WO | 9736635 A1 | 10/1997 |
| WO | 9807462 A1 | 2/1998 |
| WO | 9820920 A2 | 5/1998 |
| WO | 9832411 A1 | 7/1998 |
| WO | 9938562 A1 | 8/1999 |
| WO | 9965548 A1 | 12/1999 |
| WO | 0053242 A1 | 9/2000 |
| WO | 0137905 A2 | 5/2001 |
| WO | 0189028 A2 | 11/2001 |
| WO | 0204049 A1 | 1/2002 |
| WO | 03010557 A1 | 2/2003 |
| WO | 2004004787 A2 | 1/2004 |
| WO | 2005000403 A2 | 1/2005 |
| WO | 2005002971 A1 | 1/2005 |
| WO | 2005020274 A2 | 3/2005 |
| WO | 2005089835 A1 | 9/2005 |
| WO | 2005118031 A1 | 12/2005 |
| WO | 2006007750 A1 | 1/2006 |
| WO | 2006051531 A2 | 5/2006 |
| WO | 2006084464 A1 | 8/2006 |
| WO | 2006108026 A2 | 10/2006 |
| WO | 2006124775 A2 | 11/2006 |
| WO | 2006129301 A2 | 12/2006 |
| WO | 2007010534 A2 | 1/2007 |
| WO | 2008083313 A2 | 7/2008 |
| WO | 2009042577 A2 | 4/2009 |

OTHER PUBLICATIONS

Brochure for "PercuPump 1A" of E-Z-Em, Inc, 717 Main Street, Westbury, NY 11590, ©1990.
Brochure for the "The First and Only True Injection System, " Medrad Mark V System, Control No. 85106-00-BA-02, Nov. 1988.
Celler., A., et al., "Investigation of the dynamic SPECT (dSPECT) method for Teboroxime using a 4-D kinetic thorax model Dmcat," sixth international meeting on fully three-dimensional image reconstruction in radiology and nuclear medicine, pp. 4 (2001).
Coxson, Pg, et al., "Consequences of Using a Simplified Kinetic Model for Dynamic Pet Data," J Nuc Med, vol. 38, Issue 4, pp. 660-667 (Apr. 1, 1997).
European Search Report for European Application No. EP10015627, mailed on Jun. 16, 2011.
Feichtinger, M., et al., "Automatic and remote controlled ictal SPECT injection for seizure focus localization by use of a commercial contrast agent application pump," Epilepsia, vol. 48, Issue 7, pp. 1409-1413 (Jul. 2007).
Final Office Action mailed Oct. 17, 2012 in U.S. Appl. No. 12/748,682, Arthur E. Uber III, filed Mar. 29, 2010.
"iGEM.supTM.Sensor Module Spectroscopy Engine for Portable Instruments," eV PRODUCTS a kromek company, Retrieved from the Internet URL: http://evproducts.com/igemsm.html, on May 27, 2015, p. 1.
Injektron 82 MRT User Instructions, Version MR2, CEO535, Med-Tron GmbH(Mar. 10, 1999).
International Search Report and Written Opinion for Application No. PCT/US20071088028, mailed on Mar. 20, 2009, 13 pages.
International Search Report and Written Opinion for Application No. PCT/US2013/044031, mailed on May 28, 2014, 8 pages.
International Search Report and Written Opinion for International Application No. PCT/US09/46437, mailed on Aug. 11, 2009.
International Search Report and Written Opinion for International Application No. PCT/US11/31949, mailed on Jun. 17, 2011.
International Search Report and Written Opinion for International Application No. PCT/US2014/019229, mailed on Aug. 5, 2014.
International Search Report for International Application No. PCT/AU01/00830, mailed on Nov. 1, 2001.
International Search Report for International Application No. PCT/CH2005/000403, mailed on Sep. 15, 2009.
International Search Report for International Application No. PCT/US01/12781, mailed on Oct. 30, 2001.
International Search Report for International Application No. PCT/US03/17305, mailed on Oct. 21, 2003.
International Search Report for International Application No. PCT/US2011/039106, mailed on Oct. 3, 2011.
International Search Report for WO 2011/153457, Agamaite et al., System and Method for Planning and Monitoring Multi-Dose Radiopharmaceutical Usage on Radiopharmaceutical Injectors, Oct. 3, 2011.
LabVIEW System Design Software, National Instruments, Retrieved from the internet URL: http://www.ni.com/labview/, on May 26, 2015, pp. 1-2.
Lee, J. J., et al., "Ictal SPECT using an Attachable Automated Injector: Clinical Usefulness in the Prediction of Ictal Onset Zone," Acta Radiological, vol. 50, Issue 10, pp. 1160-1168 (Dec. 2009).
Liebel-Flarsheim company—Angiomat 6000 Digital Injection System Operator's Manual, 600950 Rev 1 (1990); p. 3-6 to 3-8, 4-52 to 4-56.
Mallinckrodt Optistar MR Digital Injection System, Operator's Manual, 801900-A (Nov. 1999).
Medrad Envision CT Injector Operation Manual, EOM 700E, 92401-T-123 Rev E, pp. 2-10 to 2-11 and pp. 2-30 to 2-35(Copyright 1995).
Medrad, Mark V/Mark V Plus Injector Operation Manual,KMP 805P Rev. B (1990); pp. 1-18 to 1-28, 3-7 to 3-13, 14-1 to 14-4.
Medrad Spectris MR Injector Operation Manual; 92901-T-107, Rev. E, pp. 2-1 to 2-18, 4-1 to 4-8 and 6-1 to 6-10 (1996).
Morris, E. D., et al., "Comparison of Two Compartmental Models for DescribingReceptor Ligand Kinetics and Receptor Availability in Multiple Injection PET Studies," Journal of Cerebral Blood Flow and Metabolism, vol. 16, Issue 5, pp. 841-853 (Sep. 1996).
"Pegasus Infusion Pump," Instechlabs, Retrieved from Internet URL: https://web.archive.org/web/20090101215244/http://www.instechlabs.com/Pum-ps/pegasus/index.php, on Mar. 26, 2015, pp. 1-2.
"Pulse Spray Injector," AngioDynamics, Retrieved from the internet URL: http://www.angiodynamics.com/pages/products/%20pulsespray.sub.-injector.-asp, on May 26, 2015, pp. 1-17.
Schiwilden, H., "A General Method for calculating the Dosage Scheme in Linear Pharmacokinetics," European Journal of Clinical Pharmacology, vol. 20, Issue 5, pp. 379-386 (1981).
Strauss, L. G., et al., "Shortened PET Data Acquisition Protocol for the Quantification of 18 F-FDG Kinetics," J Nuc Med, vol. 44, Issue 12, pp. 1933-1939 (Dec. 2003).

(56) References Cited

OTHER PUBLICATIONS

Sugawara, Y., et al., "Germ Cell Tumor: Differentiation of Viable Tumor, Mature Teratoma, and NecroticTissue with FDG PET and Kinetic Modeling," Radiology, vol. 211, Issue 1, pp. 249-256 (Apr. 1999).

Zasadny, Kr, et al., "FDG Metabolism and Uptake Versus Blood Flow in Women with Untreated Primary Breast Cancers," Eur J Nuc Med Mol Imaging, vol. 30, Issue 2, pp. 274-280 (Feb. 2003).

Zhuang, H., et al., "Dual Time Point F18-FDG PET Imaging for Differentiating Malignant from Inflammatory Processes," J Nuc Med., vol. 42, Issue 9, pp. 1412-1417 (Sep. 2001).

* cited by examiner

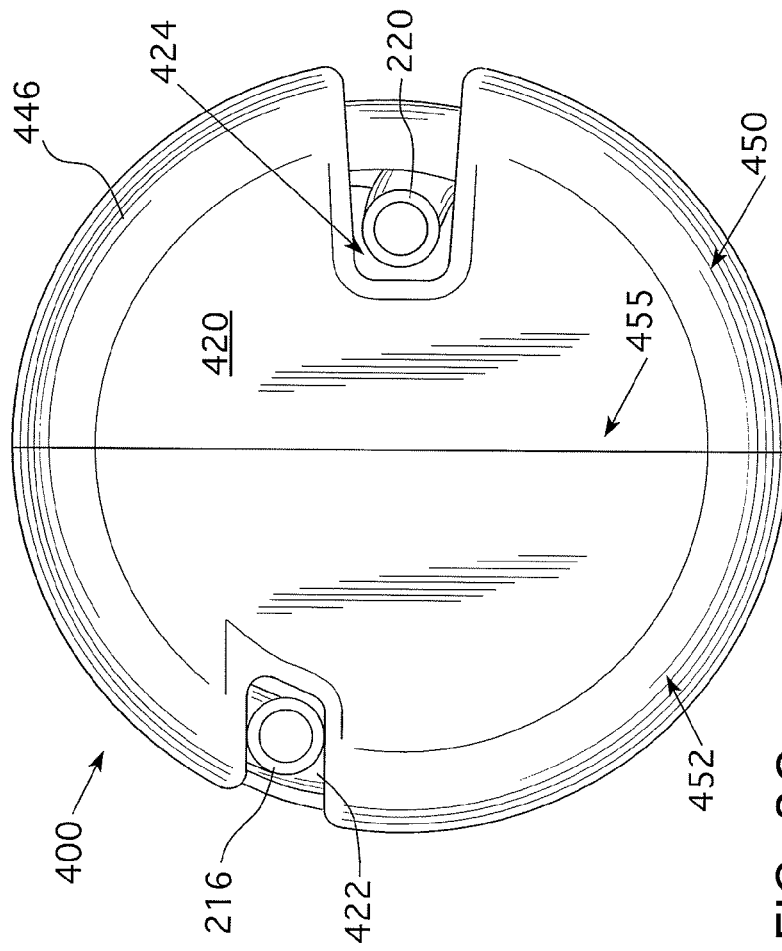
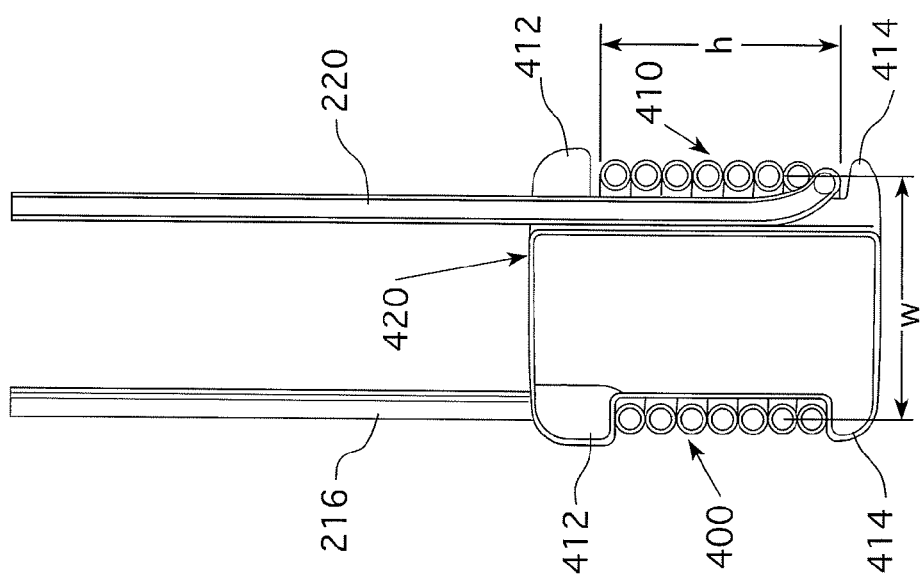

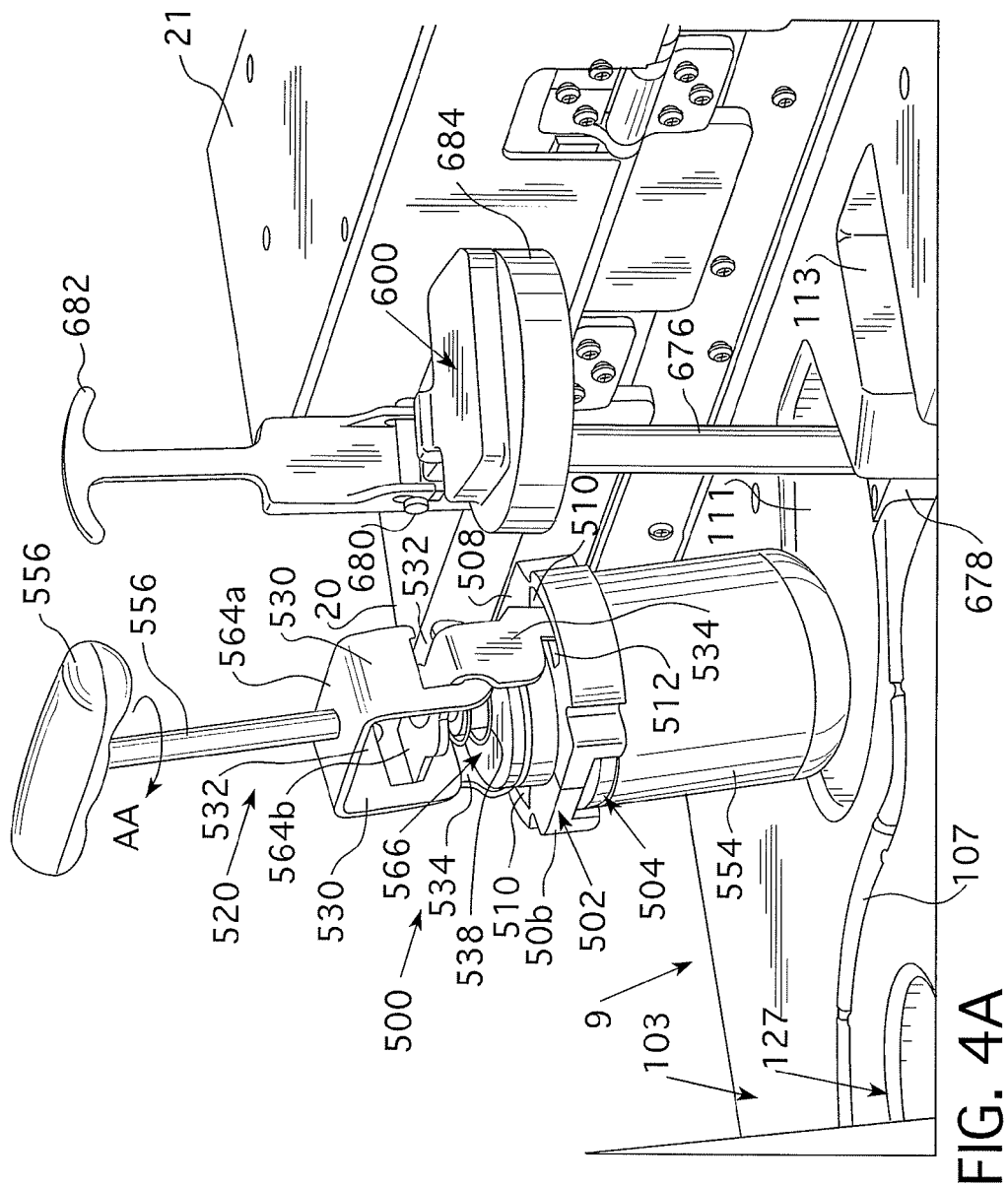

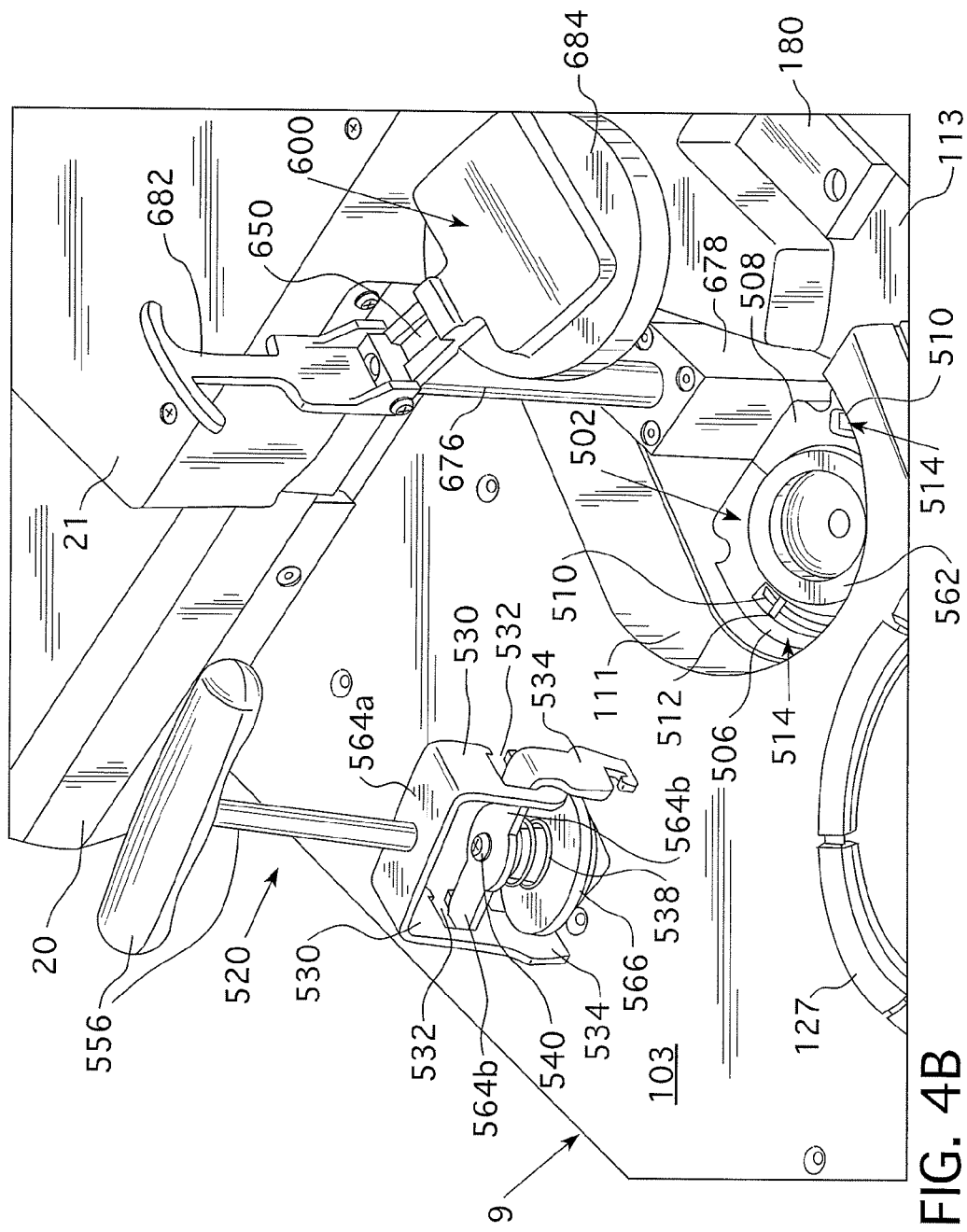

SYSTEM AND METHOD FOR PLANNING AND MONITORING MULTI-DOSE RADIOPHARMACEUTICAL USAGE ON RADIOPHARMACEUTICAL INJECTORS

CROSS REFERENCE TO RELATED APPLICATIONS

The present application is a Continuation of U.S. Ser. No. 13/700,266, having a 371(c) date of Nov. 27, 2012, which is a 371 national phase application of PCT International Application No. PCT/US2011/039106, filed on Jun. 3, 2011, and designating the United States of America, which claims the benefit of U.S. Provisional Application Ser. No. 61/351,463, filed on Jun. 4, 2010, the contents of each of which are incorporated herein by reference.

BACKGROUND

1. Technical Field

This disclosure relates to the administration of pharmaceutical substances, typically intrinsically harmful or toxic pharmaceutical substances such as radioactive pharmaceutical substances, generally known as radiopharmaceuticals, to human and animal subjects and, more specifically, to a method of and a system for planning and monitoring multi-dose radiopharmaceutical usage on radiopharmaceutical injectors.

2. Description of Related Art

Administration of radioactive pharmaceutical substances or drugs, generally termed radiopharmaceuticals, is often used in the medical field to provide information or imagery of internal body structures and/or functions including, but not limited to, bone, vasculature, organs and organ systems, and other tissue. Additionally, such radiopharmaceuticals may be used as therapeutic agents to kill or inhibit the growth of targeted cells or tissue, such as cancer cells.

Two types of imaging procedures utilizing radiopharmaceuticals are positron emission tomography (PET) or single-photon emission computerized tomography (SPECT) procedures. PET and SPECT are noninvasive, three-dimensional, imaging procedures that provide information regarding physiological and biochemical processes in patients. PET and SPECT images of, for example, the brain or another organ, are produced by injecting the patient with a dose of a radiopharmaceutical and then creating an image based on the radiation emitted by the radiopharmaceutical. The radiopharmaceutical generally includes a radioactive substance, such as a radioisotope, that can be absorbed by certain cells in the brain or other organs, concentrating it there.

Radioisotopes, especially those with short half-lives, can be relatively safely administered to patients in the form of a labeled substrate, ligand, drug, antibody, neurotransmitter, or other compound or molecule that is normally processed or used by the body (for example, glucose). The radioisotope acts as a tracer of specific physiological or biological processes. For example, fluorodeoxyglucose (FDG) is a normal molecule of glucose, the basic energy fuel of cells, to which is attached a radioisotope or radioactive fluorine (i.e., $^{18}F$). The $^{18}F$ radioisotope is produced in a cyclotron equipped with a unit to synthesize the FDG molecule.

Cells (for example, in the brain) that are more active in a given period of time after an injection of FDG will absorb more FDG because they have a higher metabolism and require more energy. The $^{18}F$ radioisotope in the FDG molecule experiences a radioactive decay, emitting a positron. When a positron collides with an electron, annihilation occurs, liberating a burst of energy in the form of two beams of gamma rays in opposite directions. The PET scanner detects the emitted gamma rays to compile a three dimensional image.

To allow for cell uptake of the radiopharmaceutical, the patient typically rests for a period of time (45-90 minutes for FDG) after the radiopharmaceutical is injected. After sufficient time for cell uptake has elapsed, the patient is typically placed on a movable bed that slides into the PET (or SPECT), or other suitable scanner. The PET scanner includes several rings of radiation detectors. Each detector emits a brief pulse of light every time it is struck with a gamma ray coming from the radioisotope within the patient's body. The pulse of light is amplified by, for example, a photomultiplier, and the information is sent to the computer for forming images of the patient.

To minimize the radiation dose to patients, radiopharmaceuticals containing radioisotopes, such as Flourine-18, Technetium-99, Carbon-11, Copper-64, Gallium-67, Iodine-123, Nitrogen-13, Oxygen-15, Rubidium-82, Thallium-201, Chromium-51, Iodine-131, Iodine-151, Iridium-192, Phosphorus-32, Samarium-153, and Yttrium-90, having relatively short half-lives are typically used for PET and SPECT imaging procedures and other radio-therapies. $^{18}F$, for example, has a half-life of 109.7 minutes.

Because of its short half-life, the radioactivity level of the radioisotope will quickly decrease after it is manufactured in a cyclotron or a reactor. Consequently, the elapsed time (and corresponding decrease in radioactivity level of the radioisotope) after synthesis of the radiopharmaceutical must be factored into calculating the volume of radiopharmaceutical required to be injected into the patient to deliver the desired radioactivity dose. If the time delay after synthesis is long in relation to the radioisotope's half-life or if the calculated volume of radiopharmaceutical to be injected into the patient is insufficient to deliver the desired radioactivity dose, the delivered radioactivity dose may be too low to provide diagnostic-quality images, resulting in wasted time and effort and exposing the patient and medical personnel to unnecessary radiation.

In addition, radiopharmaceutical agents used in imaging procedures and therapeutic procedures are hazardous to attending medical personnel. These agents are toxic and can have physical and/or chemical effects for attending medical personnel such as clinicians, imaging technicians, nurses, and pharmacists. Excessive radiation exposure is harmful to attending medical personnel due to their occupational repeated exposure to the radiopharmaceuticals. However, due to the short half-life of typical radiopharmaceutical agents and small applied dosages, the radiation exposure risk-to-benefit ratio for individual patients is acceptable. The constant and repeated exposure of medical personnel to radiopharmaceuticals over an extended period of time is a significant problem in the nuclear medicine field.

With the foregoing background in place, exemplary current practice of generating, preparing, and administration of radiopharmaceuticals will now be described. Typical radiopharmaceutical treatment practice in the United States includes having the radiopharmaceutical agent initially generated off-site from a treatment location, typically a hospital, by an outside nuclear medicine facility and then delivered to the treatment location for further preparation, for example, individual dosing and administration. The treatment location, for example, a hospital, orders specific radioactive substances to be ready at specific times for specific patients. These substances are prepared by the outside nuclear medicine facility and with sufficient radioactivity that they will have the desired radioactivity level at the targeted time. For example, the outside nuclear medicine provider may have a facility equipped with a cyclotron or radioisotope generator in, for example, a lead-shielded enclosure wherein the radiopharmaceutical agent, namely, a radioactive isotope is generated or created. Further refining or dose preparation steps, namely, placing the radioisotope in injectable form, may occur at the off-treatment site. Thus, the outside provider may provide a radiopharmaceutical substance to the treatment site having a desired radioactivity level at the targeted time. Further "individual" dose preparation of the radiopharmaceutical agent may occur at the treatment site. Alternatively, the outside provider may provide a "finished" radiopharmaceutical agent ready for injection to a specified patient at a specified time so that treatment site personnel are only required to confirm that the correct radioactive dosage is present in the radiopharmaceutical agent, for example, in a stand-alone radiation dosimetry device as described previously. During the forgoing process, there is frequent close-proximity contact with radioactive materials by personnel and, as described previously, handling and transport shielding devices are needed for the protection of these personnel.

Transport pigs are commonly employed to transport the radiopharmaceutical agents, which are individual doses prepared for individual patients, to the treatment facility. At the treatment facility, data about each unit dose is entered into a facility computer either manually or through reading a bar code, floppy disk, or other similar data format, which may accompany or be on the transport pig or the radiopharmaceutical agent container. When it is time to deliver a specified unit dose to a specified patient, treatment facility personnel must remove, for example, a syringe containing the radiopharmaceutical agent from the transport pig and confirm that the dose in the syringe is within the range prescribed for that patient. Alternatively, the attending personnel must transfer the radiopharmaceutical agent to a shielded syringe as identified previously and confirm dosage. If the dose is too high, some is discarded into a shielded waste container. If the dose is too low, either a different syringe is used and/or additional agent is loaded into the syringe if available. While it is possible for the attending treatment site personnel to be involved with dosage preparation, typical United States practice is to have the radiopharmaceutical agent delivered to the treatment site which will have the desired radioactivity level at the targeted time. Manual manipulation of the radiopharmaceutical agent at the treatment site is limited at the treatment site due to this procedure. Nonetheless, various manual checks are required to confirm that a correct radiopharmaceutical dose is ready for injection into a specific patient. These manual checks include visual inspections and radioactivity measurements as noted above.

As an example of the foregoing, in PET imaging, an injectable radiopharmaceutical agent such as, for instance, FDG (fluorodeoxyglucose) is fabricated in a cyclotron device at an outside nuclear medicine facility. Thereafter, the FDG is processed to be in a radiopharmaceutical form and is transferred in an individual dose container (i.e., container, bottle, syringe, etc.) and the container is loaded into a transport pig to prevent unnecessary radiation exposure to personnel, such as the radio-pharmacist, technician, and driver responsible for creation, handling, and transport of the FDG from the cyclotron site to the PET imaging site. Since the half-life of FDG is short, approximately 110 minutes, it is necessary to quickly transport the FDG to the PET imaging site. Depending upon the elapsed transport time and the initial radioactivity level of the FDG at the time of fabrication, the radioactivity level of the FDG may need to be re-measured at the PET imaging site. As an example, if the radioactivity level is too high, the transport radio-pharmacist or a radio-pharmacist at the PET imaging site may be required to dilute the FDG with a diluent such as, for instance, saline solution, and remove part of the volume or extract fluid to reduce radioactivity prior to patient injection. During this entire process, the handling of FDG from creation to patient injection may be entirely manual. Within this process, shielding products, as described previously (i.e., transport pigs, syringe shields, L-blocks, etc.) are used to shield individuals from FDG. While shielding may reduce the radiation exposure of the radio-pharmacist, the radio-pharmacist may still be exposed to emissions from the radiopharmaceutical agent during the manual mixing, volume reduction, and/or dilution process needed to obtain the required dose. After injection and often after an additional delay to allow the radiopharmaceutical to reach and be absorbed by the desired regions of interest in the body, the patient is typically placed on a movable bed that slides by remote control into a circular opening of an imaging scanner referred to as the gantry. Positioned around the circular opening and inside the gantry are several rings of radiation detectors. In one type of radiation detector, each detector emits a brief pulse of light every time it is struck with a gamma ray coming from the radionuclide within the patient's body. The pulse of light is amplified by a photomultiplier converted to an electronic signal and the information is sent to the computer that controls the apparatus and records imaging data.

Clinical sites that inject radiopharmaceuticals typically do so using single-use doses provided for each patient. Sites order unit doses assayed to the planned injection time for each planned patient. These doses are often ordered with a sufficient activity margin to accommodate radiopharmaceutical decay due to slight differences between planned and actual injection times. Sites typically order extra unit doses to handle add-on patients or to mitigate drastic schedule variations within their planned patient set.

However, it is becoming more common to have radiopharmaceutical agents delivered in a multi-dose format to the treatment site. A multi-dose container provides all scheduled patient doses in a single container. A patient's dose is extracted from the multi-dose container at the time of injection. Ideally the multi-dose container will service all patients, including planned patients that are not dosed at their scheduled time and possibly unplanned for patients.

When determining the container configuration for their patient schedule, clinicians must trade off minimizing cost with being able to handle schedule deviations. As such, the container configuration will typically only account for a typical schedule variation for a given clinician's site. There will be times when extreme schedule variations will render the ordered multi-dose container inadequate to service the planned patient schedule. Clinicians must take corrective actions, such as ordering more doses, when they are going to have activity shortfalls. Due to the long turn-around time when ordering doses, it is imperative that clinicians are made aware of a suspected shortfall in their multi-dose container as early as possible. Accordingly, a need exists for a system and a method to quickly and easily determine a multi-dose container configuration that meets a planned patient schedule with a sufficient margin to account for reasonable schedule variation while minimizing multi-dose container cost.

Furthermore, when determining the container configuration for their patient schedule, clinician's must trade off minimizing cost with being able to handle schedule deviations. As such, the container configuration will typically only account for typical schedule variation for a given clinicians site. There will be times when extreme schedule variations will render the ordered multi-dose container inadequate to service the planned patient schedule. Clinicians must take corrective actions, such as ordering more doses, when they are going to have activity shortfalls. Due to the long turn-around time when ordering doses, it is imperative that clinicians are made aware of a suspected shortfall in their multi-dose container as early as possible. Accordingly, a further need exists for a system and method for monitoring multi-dose container usage and predicting a likely shortfall at the earliest possible moment.

BRIEF SUMMARY

Therefore, it is an object of the present disclosure to provide a method and system that overcome some or all of the drawbacks and deficiencies evident in the prior art. More specifically, the systems and methods described herein allow for a clinician to quickly and easily determine a multi-dose container configuration that meets a planned patient schedule with a sufficient margin to account for reasonable schedule variation while minimizing multi-dose container cost. In addition, the systems and methods of the present disclosure allow for the monitoring of multi-dose container usage and predict a likely shortfall at the earliest possible moment.

Accordingly, provided is a method for planning and monitoring radiopharmaceutical usage during a plurality of radiopharmaceutical injection procedures. The method includes: providing a schedule of the plurality of radiopharmaceutical injection procedures to produce a planned patient schedule; based on the planned patient schedule, calculating a multi-dose container configuration for use during the plurality of radiopharmaceutical injection procedures; transferring the planned patient schedule to a radiopharmaceutical fluid delivery system; providing the multi-dose container configuration to the radiopharmaceutical fluid delivery system; and conducting the plurality of radiopharmaceutical injection procedures based on the planned patient schedule.

The schedule may include the time of an injection procedure for each patient and an activity removed from the multi-dose container of radiopharmaceutical for each patient. The step of providing the schedule may include at least one of: manually entering the time and activity for each patient into a computer; retrieving the time and activity for each patient from a memory device associated with the computer; and retrieving the time and activity for each patient from a remotely located patient device over a network. The planned patient schedule may be provided such that it is editable after being initially provided to accommodate add-on patients, cancellations, time modifications to patients already provided on the planned patient schedule, modifications to an activity removed from the multi-dose container of radiopharmaceutical to patients already provided on the planned patient schedule, or any combination thereof.

The method may further include the steps of: monitoring the multi-dose container configuration during the plurality of radiopharmaceutical injection procedures; determining if there is a risk that at least one of the plurality of radiopharmaceutical injection procedures may not be completed properly; and alerting an operator if there is risk that at least one of the plurality of radiopharmaceutical injection procedures may not be completed. The step of monitoring the multi-dose container configuration may include: determining remaining radiopharmaceutical activity and volume of the multi-dose container configuration to provide a remaining activity estimation; and adjusting the remaining activity estimation based on isotope decay. The step of determining the remaining radiopharmaceutical activity of the multi-dose container configuration may be performed by one of an ionization chamber, a CZT crystal detector, a Geiger-Müller counter, and a scintillating counter.

The method may further include the step of displaying the planned patient schedule on a graphical user interface of the radiopharmaceutical fluid delivery system. The step of alerting an operator may include highlighting one of the plurality of radiopharmaceutical injection procedures in the planned patient schedule. The method may also include the step of updating the planned patient schedule to accommodate a maximum number of the plurality of radiopharmaceutical injection procedures if there is risk that at least one of the plurality of radiopharmaceutical injection procedures may not be completed.

Further provided is an article having a machine-readable storage medium containing instructions that, if executed, enable a processor to: load a schedule of a plurality of radiopharmaceutical injection procedures to produce a planned patient schedule; and based on the planned patient schedule, calculate a multi-dose container configuration for use during the plurality of radiopharmaceutical injection procedures.

The article may also include instructions that, if executed, enable the processor to transfer the planned patient schedule to a radiopharmaceutical fluid delivery system. The schedule may include time of an injection procedure for each patient and an activity removed from the multi-dose container of radiopharmaceutical for each patient. The step of providing the schedule may include at least one of manually entering the time and activity for each patient into a computer, retrieving the time and activity for each patient from a memory device associated with the computer, and retrieving the time and activity for each patient from a remotely located patient device over a network. The planned patient schedule may be editable after initial loading to accommodate add-on patients, cancellations, time modifications to patients already provided on the planned patient schedule, modifications to an activity removed from the multi-dose container of radiopharmaceutical to patients already provided on the planned patient schedule, or any combination thereof.

Also provided is a planning and monitoring software stored on a storage medium to plan and monitor radiopharmaceutical usage during a plurality of radiopharmaceutical injection procedures. The software includes programming instructions that, if executed, enable a processor to: load a schedule of a plurality of radiopharmaceutical injection procedures to produce a planned patient schedule; and based on the planned patient schedule, calculate a multi-dose container configuration for use during the plurality of radiopharmaceutical injection procedures.

The planning and monitoring software may further include instructions that, if executed, enable the processor to transfer the planned patient schedule to a radiopharmaceutical fluid delivery system. The schedule may include time of an injection procedure for each patient and an activity removed from the multi-dose container of radiopharmaceutical for each patient. The step of providing the schedule may include at least one of manually entering the time and activity for each patient into a computer, retrieving the time and activity for each patient from a memory device associated with the computer, and retrieving the time and activity for each patient from a remotely located patient device over a network. The planned patient schedule may be provided such that it is editable after initial loading to accommodate add-on patients, cancellations, time modifications to patients already provided on the planned patient schedule, modifications to an activity removed from the multi-dose container of radiopharmaceutical to patients already provided on the planned patient schedule, or any combination thereof.

Further provided is a radiopharmaceutical fluid delivery device for performing a radiopharmaceutical injection procedure. The radiopharmaceutical fluid delivery device includes: a disposable administration set for allowing fluid flow from a radiopharmaceutical source of the radiopharmaceutical fluid delivery device to a patient; a pumping mechanism in fluid communication with the disposable administration set and the radiopharmaceutical source to pump fluid from the radiopharmaceutical source and through the disposable administration set to the patient; a control unit operatively coupled to the pumping mechanism and configured to: a) receive a schedule of a plurality of radiopharmaceutical injection procedures; and b) control the pumping mechanism to conduct the plurality of radiopharmaceutical injection procedures based on the schedule; and a display unit operatively coupled to the control unit for displaying the schedule to an operator.

The control unit may be further configured to: c) monitor the multi-dose container configuration during the plurality of radiopharmaceutical injection procedures; d) determine if there is a risk that at least one of the plurality of radiopharmaceutical injection procedures may not be completed properly; and e) alert an operator if there is risk that at least one of the plurality of radiopharmaceutical injection procedures may not be completed.

The disposable administration set may be a multipatient disposable administration set that includes a medical fluid component; a radiopharmaceutical component; a coil component coupled to the medical fluid component and the radiopharmaceutical component; and a waste component coupled to the medical fluid component, the coil component, and the radiopharmaceutical component.

Also provided is a method for optimizing a schedule of a plurality of radiopharmaceutical injection procedures. The method includes the steps of: providing a schedule of the plurality of radiopharmaceutical injection procedures to produce a planned patient schedule; transferring the planned patient schedule to a radiopharmaceutical fluid delivery system; changing the planned patient schedule; and suggesting changes in at least one of radioactive dose and infusion time for at least one future patient in the planned patient schedule. The method may also include the step of: determining a new, optimized patient schedule based on the changes suggested.

The schedule may include the time of an injection procedure for each patient and an activity removed from the multi-dose container of radiopharmaceutical for each patient. The step of providing the schedule may include at least one of: manually entering the time and activity for each patient into a computer; retrieving the time and activity for each patient from a memory device associated with the computer; and retrieving the time and activity for each patient from a remotely located patient device over a network. The planned patient schedule may be provided such that it is editable after being initially provided to accommodate add-on patients, cancellations, time modifications to patients already provided on the planned patient schedule, modifications to an activity removed from the multi-dose container of radiopharmaceutical to patients already provided on the planned patient schedule, or any combination thereof.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended to limit the scope of this disclosure. As used in the specification and the claims, the singular form of "a", "an", and "the" include plural referents unless the context clearly dictates otherwise.

BRIEF DESCRIPTION OF THE DRAWINGS

FIG. 3B is a partial cross-sectional view of FIG. 3A;

FIG. 3C is a plan view (in partial cross-section) taken along line 3C-3C of FIG. 3A;

FIG. 4A is an elevational view of preferred embodiments of a container shield carrying system and a container access system according to an embodiment;

FIG. 4B is a perspective view showing the container shield, the container shield carrying system, and the container access system of FIG. 4A;

DETAILED DESCRIPTION

Figure 1A:
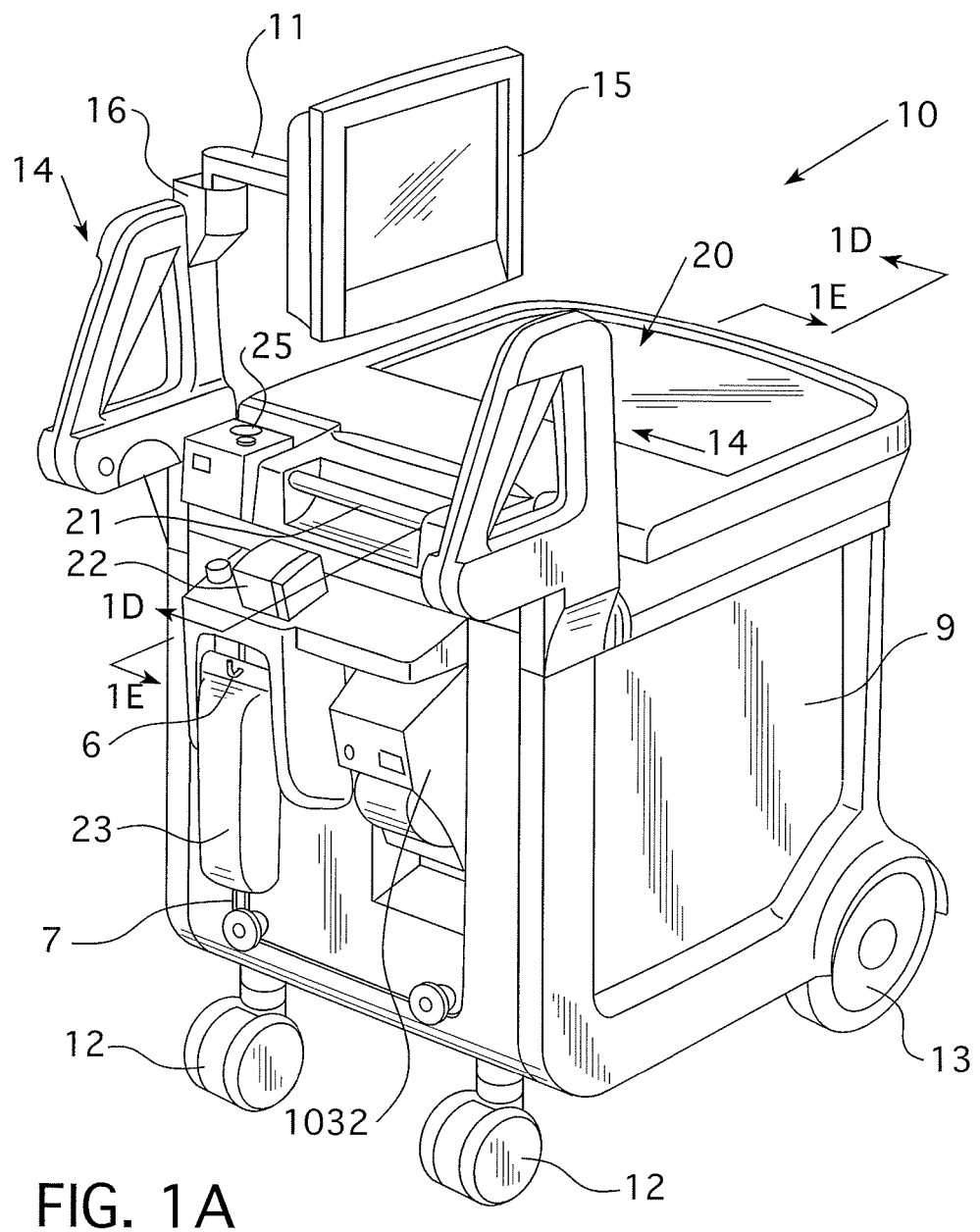
FIG. 1A is a perspective view of a fluid delivery system according to an embodiment.

For purposes of the description hereinafter, the terms "upper", "lower", "right", "left", "vertical", "horizontal", "top", "bottom", "lateral", "longitudinal", and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments.

An exemplary radiopharmaceutical fluid delivery system for use with the system disclosed herein is disclosed in United States Patent Application Publication No. 2008/0177126 to Tate et al., the disclosure of which is incorporated herein by reference. More specifically, FIGS. 1A-1F show an exemplary embodiment of such a radiopharmaceutical fluid delivery system 10. The fluid delivery system 10 may be configured as a cart-like apparatus 9 having wheels 13 and/or casters 12 for allowing the system to be movable. One or more of the wheels 13 may be lockable to prevent the system 10 from moving once it is in position. The system 10 also preferably includes one or more handles 14 for allowing an operator to move or position the system 10. Alternately, the fluid delivery system 10 may be a stand-alone or fixed-position apparatus.

The fluid delivery system 10 includes a display or graphical user interface (GUI) 15 for programming and operating the system 10. The GUI display 15 may be attached to one of the handles 14 (as shown) of the system 10. The display 15 may be a color display and incorporate touch-screen capability, as known in the art, for ease of use. The display 15 may be fixed, but is preferably pivotally connected to the fluid delivery system 10 (as shown), by means of a movable arm 11 that is pivotally connected to a joint 16. Further, the display 15 may be tilted or swiveled with respect to the arm 11 to allow for optimal positioning of the display 15 by an operator.

Figure 1B:
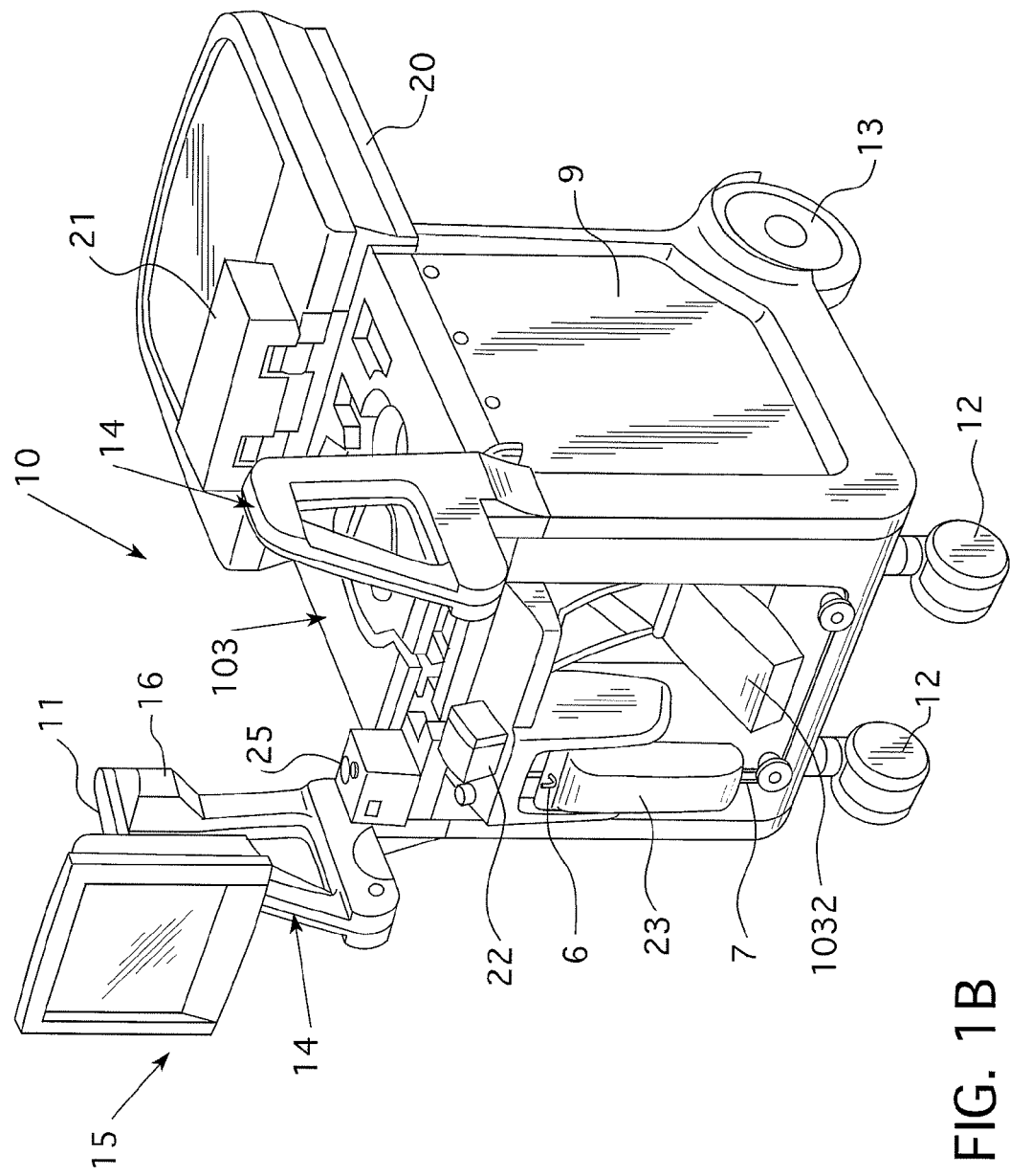
FIG. 1B is another perspective view of the fluid delivery system of FIG. 1A with the shielded cover thereof in a retracted position.
Figure 1C:
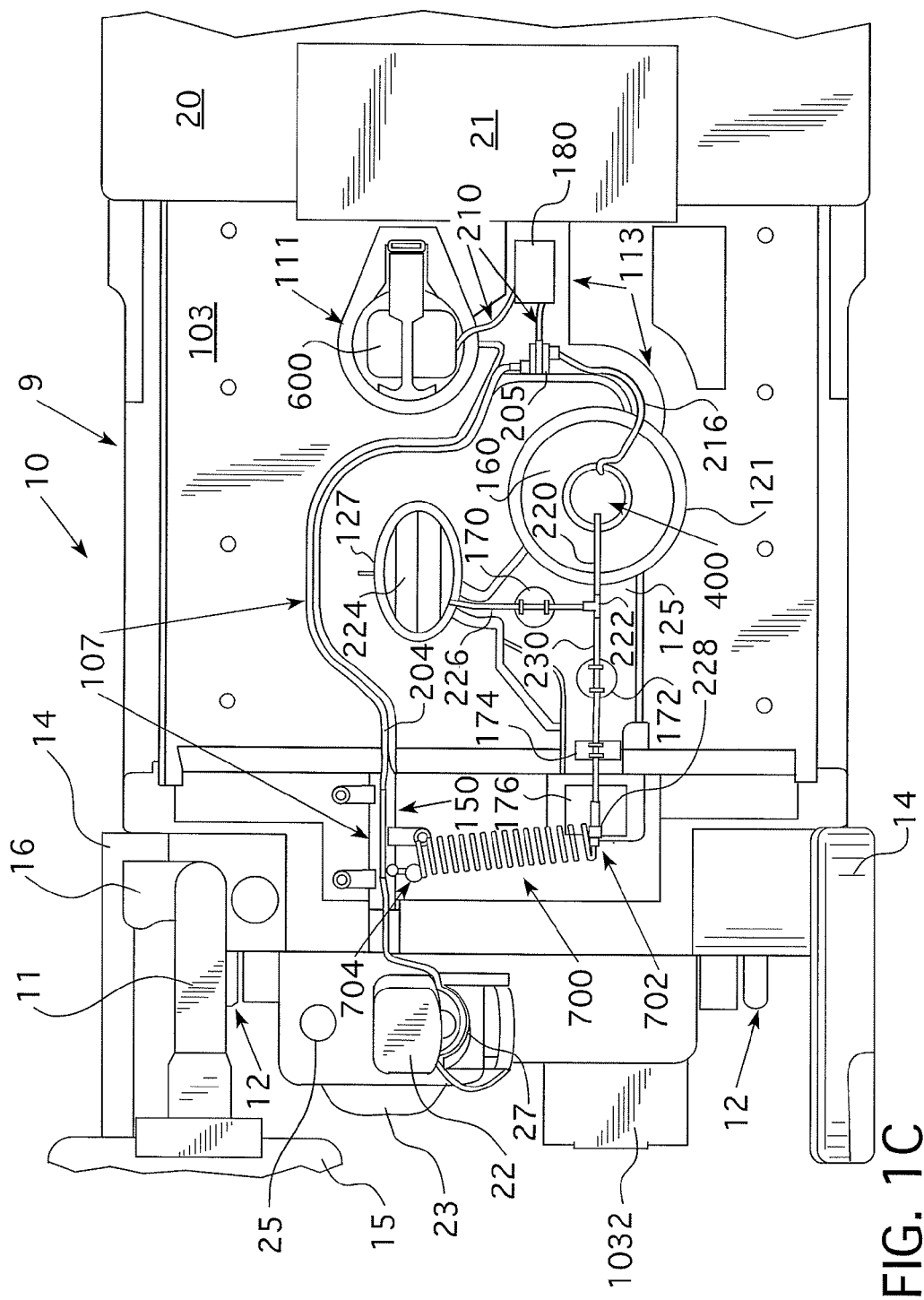
FIG. 1C is a top plan view of the fluid delivery system shown in FIGS. 1A and 1B with various fluid path components positioned therein.
Figure 1D:
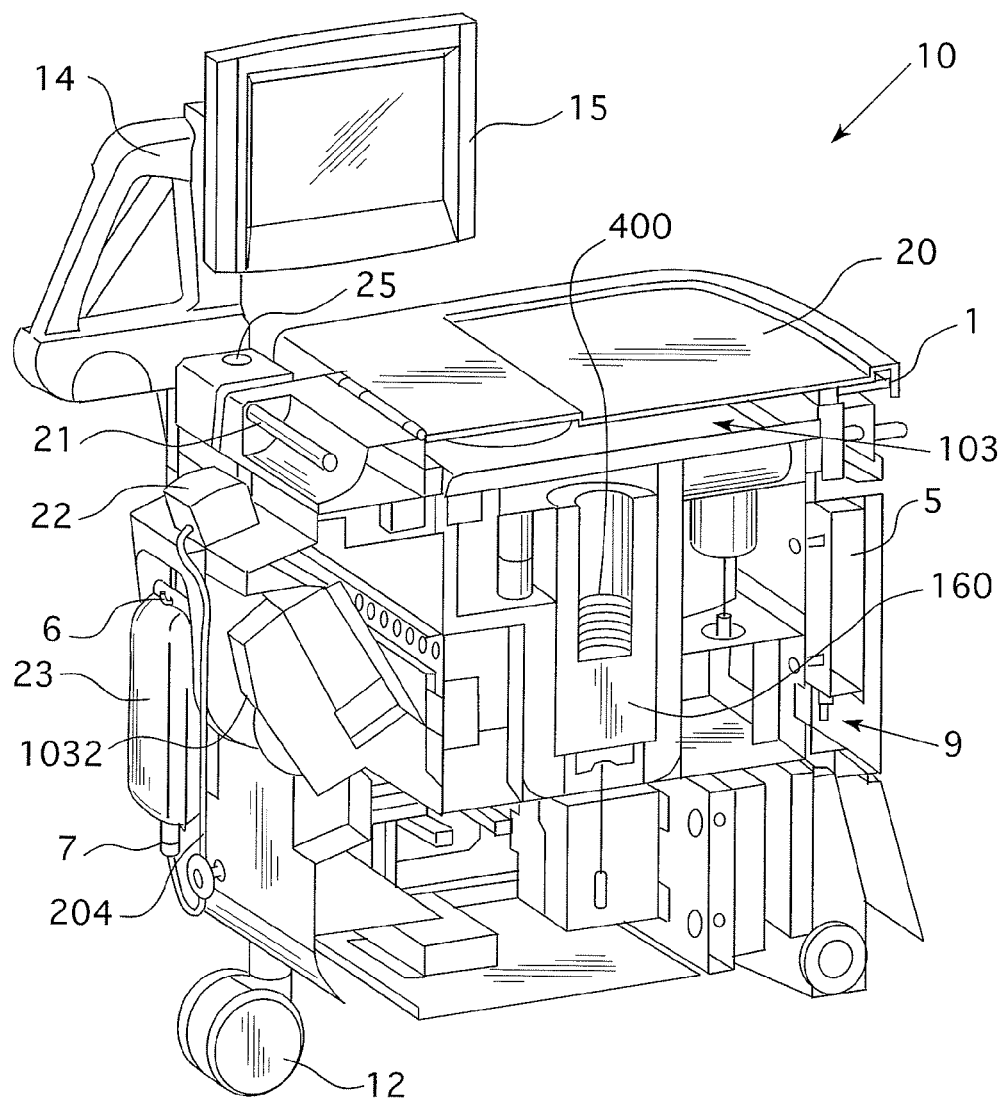
FIG. 1D is a cross-sectional view taken along line 1D-1D of FIG. 1A.
Figure 1E:
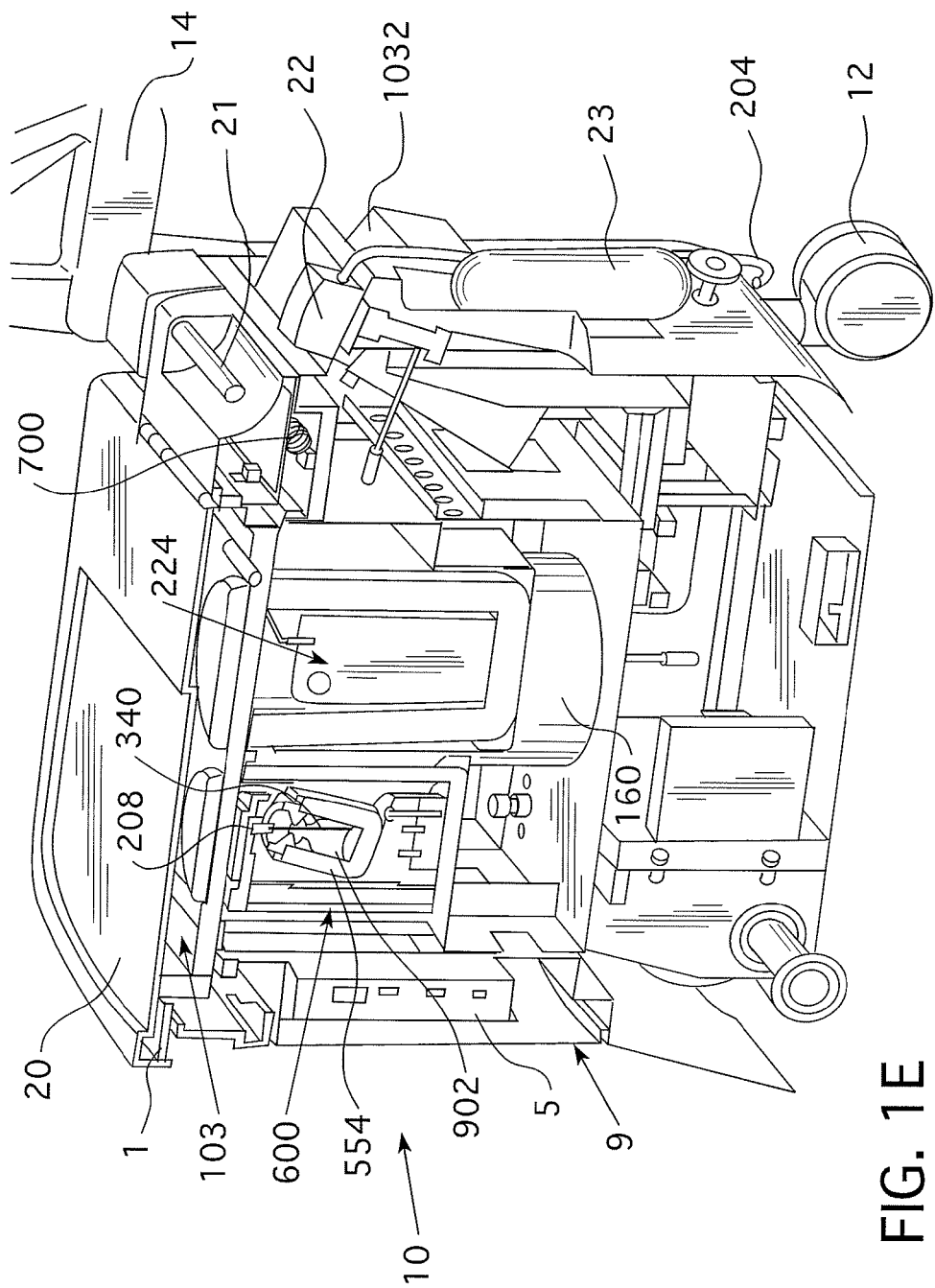
FIG. 1E is a cross-sectional view taken along line 1E-1E of FIG. 1A.
Figure 1F:
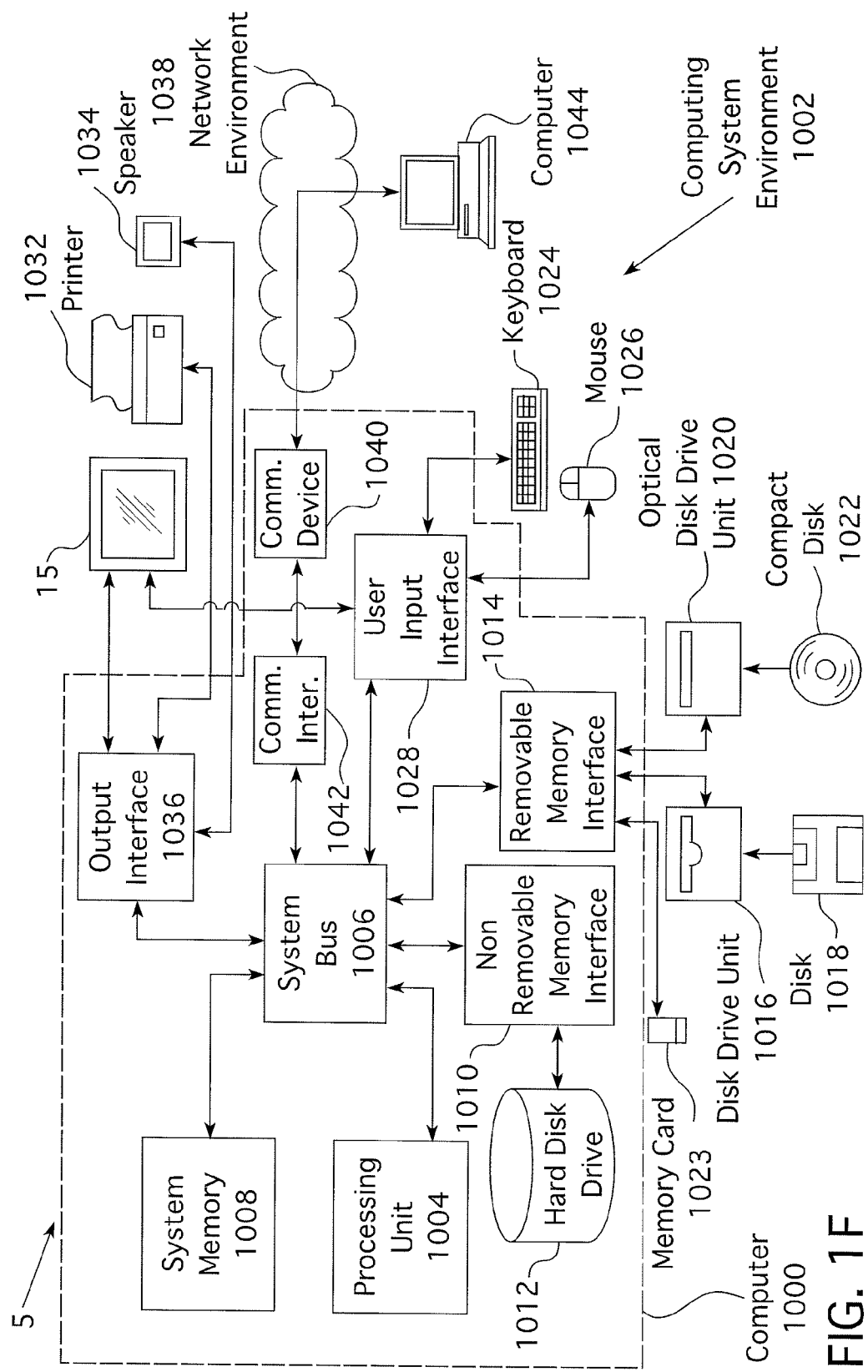
FIG. 1F is a block diagram illustrating a control system for use with the fluid delivery system of FIG. 1A.

With specific reference to FIG. 1F, GUI touch-screen display 15 may be part of a control system 5 embodied as a computer 1000 in a computing system environment 1002 used for controlling an injection procedure of the fluid delivery system 10. While any suitable computing device may be used to control the fluid delivery system 10, an exemplary embodiment of one computing system and computing system environment 1002 will be discussed hereinafter with reference to FIG. 1F. This computing system environment 1002 may include, but is not limited to, at least one computer 1000 having certain components for appropriate operation, execution of code, and creation and communication of data. For example, the computer 1000 includes a processing unit 1004 (typically referred to as a central processing unit or CPU) that serves to execute computer-based instructions received in the appropriate data form and format. Further, this processing unit 1004 may be in the form of multiple processors executing code in series, in parallel, or in any other manner for appropriate implementation of the computer-based instructions.

In order to facilitate appropriate data communication and processing information between the various components of the computer 1000, a system bus 1006 is utilized. The system bus 1006 may be any of several types of bus structures, including a memory bus or memory controller, a peripheral bus, or a local bus using any of a variety of bus architectures. In particular, the system bus 1006 facilitates data and information communication between the various components (whether internal or external to the computer 1000) through a variety of interfaces, as discussed hereinafter.

The computer 1000 may include a variety of discrete computer-readable media components. For example, this computer-readable media may include any media that can be accessed by the computer 1000, such as volatile media, non-volatile media, removable media, non-removable media, etc. As a further example, this computer-readable media may include computer storage media, such as media implemented in any method or technology for storage of information such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 1000. Further, this computer-readable media may include communications media, such as computer-readable instructions, data structures, program modules, or other data in a modulated data signal such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The computer 1000 further includes a system memory 1008 with computer storage media in the form of volatile and non-volatile memory, such as ROM and RAM. A basic input/output system (BIOS) with appropriate computer-based routines assists in transferring information between components within the computer 1000 and is normally stored in ROM. The RAM portion of the system memory 1008 typically contains data and program modules that are immediately accessible to or presently being operated on by processing unit 1004, e.g., an operating system, application programming interfaces, application programs, program modules, program data, and other instruction-based computer-readable code.

The computer 1000 may also include other removable or non-removable, volatile or non-volatile computer storage media products. For example, the computer 1000 may include a non-removable memory interface 1010 that communicates with and controls a hard disk drive 1012, i.e., a non-removable, non-volatile magnetic medium, a removable, non-volatile memory interface 1014 that communicates with and controls a magnetic disk drive unit 1016 (which reads from and writes to a removable, non-volatile magnetic disk 1018), an optical disk drive unit 1020 (which reads from and writes to a removable, non-volatile optical disk, such as a CD ROM 1022), a Universal Serial Bus (USB) port for use in connection with a removable memory card 1023, etc. However, it is envisioned that other removable or non-removable, volatile or non-volatile computer storage media can be used in the exemplary computing system environment 1002, including, but not limited to, magnetic tape cassettes, DVDs, digital video tape, solid state RAM, solid state ROM, etc. These various removable or non-removable, volatile or non-volatile magnetic media are in communication with the processing unit 1004 and other components of the computer 1000 via the system bus 1006. The drives and their associated computer storage media discussed above and illustrated in FIG. 1F provide storage of operating systems, computer-readable instructions, application programs, data structures, program modules, program data, and other instruction-based computer-readable code for the computer 1000 (whether duplicative or not of the information and data in the system memory 1008).

Desirably, an operator of the fluid delivery system 10 will enter commands, information, and data into the computer 1000 using the touch-screen of the GUI display 15 via an operator input interface 1028. However, it has been envisioned that an operator may enter commands, information, and data into the computer 1000 using other attachable or operable input devices, such as a keyboard 1024, a mouse 1026, etc., via the operator input interface 1028. Of course, a variety of such input devices may be utilized, e.g., a microphone, a trackball, a joystick, a touchpad, a scanner, etc., including any arrangement that facilitates the input of data and information to the computer 1000 from an outside source. As discussed, these and other input devices are often connected to the processing unit 1004 through the operator input interface 1028 coupled to the system bus 1006, but may be connected by other interface and bus structures, such as a parallel port, game port, or a USB. Still further, data and information can be presented or provided to an operator in an intelligible form or format through certain output devices, such as the GUI display 15 (to visually display this information and data in electronic form), a printer 1032 (to physically display this information and data in print form), a speaker 1034 (to audibly present this information and data in audible form), etc. All of these devices are in communication with the computer 1000 through an output interface 1036 coupled to the system bus 1006. It is envisioned that any such peripheral output devices be used to provide information and data to the operator.

The computer 1000 may operate in a network environment 1038 through the use of a communications device 1040, which is integral to the computer or remote therefrom. This communications device 1040 is operable by and in communication with the other components of the computer 1000 through a communications interface 1042. Using such an arrangement, the computer 1000 may connect with or otherwise communicate with one or more remote computers, such as a remote computer 1044 of a hospital information system, which typically includes many or all of the components described above in connection with the computer 1000. Using appropriate communications devices 1040, e.g., a modem, a network interface, or adapter, etc., the computer 1000 may operate within and communicate through a local area network (LAN) and a wide area network (WAN), but may also include other networks such as a virtual private network (VPN), an office network, an enterprise network, an intranet, the Internet, etc. It will be appreciated that the network connections shown are exemplary and other means of establishing a communications link between the computers 1000, 1044 may be used.

As used herein, the computer 1000 includes or is operable to execute appropriate custom-designed or conventional software to perform and implement the processing steps of the methods and systems disclosed herein, thereby forming a specialized and particular computing system. Accordingly, the presently-invented methods and systems may include one or more computers 1000 or similar computing devices having a computer-readable storage medium capable of storing computer-readable program code or instructions that cause the processing unit 1004 to execute, configure, or otherwise implement the methods, processes, and transformational data manipulations discussed herein. Still further, the computer 1000 may be in the form of a personal computer coupled to the fluid delivery system 10, a processor formed integrally with the fluid delivery system 10, a computer provided remotely from the fluid delivery system 10, or any other type of computing device having the necessary processing hardware to appropriately process data to effectively implement the presently-invented computer-implemented method and system.

Figure 4C:
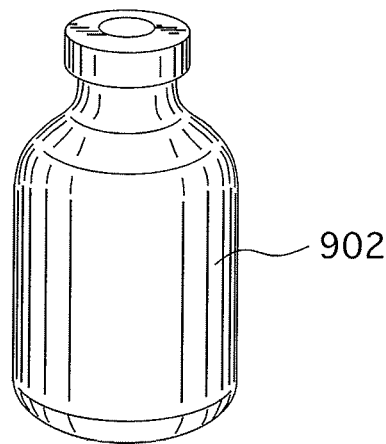
FIG. 4C is an elevational view of a pharmaceutical container that may be used in the fluid delivery system according to an embodiment.

Returning to FIGS. 1A-1E, the fluid delivery system 10 may include a retractable lid or cover 20 having a primary handle including a latch release 1 (see FIGS. 1D and 1E) and a secondary handle 21. The lid 20 may cover an upper surface 103 that defines a number of recessed portions, such as wells and troughs, into which a container or container (see 902 in FIG. 4C) of a pharmaceutical or a radiopharmaceutical (discussed in more detail below) and various components of a multi-patient fluid path set 200 (hereinafter MPDS, discussed in more detail below) may be positioned during an injection procedure. A locking mechanism, such as a combination or a key lock (not shown), may be used to lock the lid 20 in a closed position to, for example, prevent use or access of the system 10 by unauthorized personnel. In another embodiment, the locking mechanism may be a software-implemented lock, such as a password-protected access point, that is accessible through the display 15 and is adapted to lock the cover in a closed position and/or to prevent unauthorized personnel from accessing or operating the system 10.

The lid 20 is slidable or retractable (by, for example, using primary handle and latch release 1) with respect to the cart 9 to allow for insertion and removal of the container or container 902 and MPDS 200 from the fluid delivery system 10. The lid 20, upper surface 103, and various other portions of the cart 9 preferably include suitable radioactive shielding (such as lead) for minimizing potential radiation exposure from the radiopharmaceutical to the operator. In this manner, the radiopharmaceutical container 902 and the components of the MPDS 200 can lie below the plane of surface 103, whereupon the surface 103 or one or more portions thereof can be covered by the lid 20 during use to limit radiation exposure to the operator or other medical personnel. Further, instead of a retractable lid 20, surface 103 itself could be disposed on a portion of the fluid delivery system 10 (e.g., a drawer-type mechanism) that slidably displaces with respect to a remainder of the fluid delivery system 10.

As further shown in FIGS. 1A, 1B, and 1D, the fluid delivery system 10 includes a pumping mechanism, such as a peristaltic pump 22, a removable/replaceable source of medical fluid 23 (such as saline), an output device such as printer 1032, and an interrupt button 25. The peristaltic pump 22 is shown in a closed position in FIG. 1A, but may be opened (see FIGS. 1B, 1C, and 2B) to receive a length of tubing 27 (see FIGS. 1C and 2A) in fluid connection with the source of medical fluid 23 to inject the fluid into a patient (discussed in more detail below). While a peristaltic pump 22 is currently preferred, any suitable type of pumping mechanism, such as a piston-driven syringe pump, gear pump, rotary pump, or in-line pump, may be used.

The printer 1032 may be used to generate records of the injection and/or imaging procedures performed on patients, for inclusion in patients' medical records or for billing or inventory purposes. The printer 1032 may be pivotally connected to the system 10 (see FIG. 1B) to allow an operator to load paper or labels into the printer 1032.

The interrupt button 25 allows an operator to quickly and easily pause or abort an injection procedure in the event of, for example, patient discomfort or an emergency, without having to resort to the GUI display 15 (which also can be manipulated to pause or abort an injection procedure). The interrupt button 25 may be connected to LEDs and/or a printed circuit board to provide visual and/or auditory alarms when the interrupt button 25 has been activated.

Turning to FIGS. 1C-1F, 2A, and 2B, additional features and components of the fluid delivery system 10, including the upper surface 103, the MPDS 200, a container access system 600, and a single-patient fluid path set 700 (hereinafter SPDS), will be discussed.

As shown in FIG. 1C, the upper surface 103 generally defines wells and recesses or troughs into which various components of the MPDS 200 are situated. Specifically, a first recess or trough 107 accommodates a first tubing section 204 of the MPDS 200 and a tubing holder 150 for holding the tubing section 204 and preventing it from getting kinked or tangled with, for example, the SPDS 700. The first tubing section 204 may also include the tubing length 27 that is placed within the peristaltic pump 22 and is in fluid connection with the medical fluid source 23.

Figure 3A:
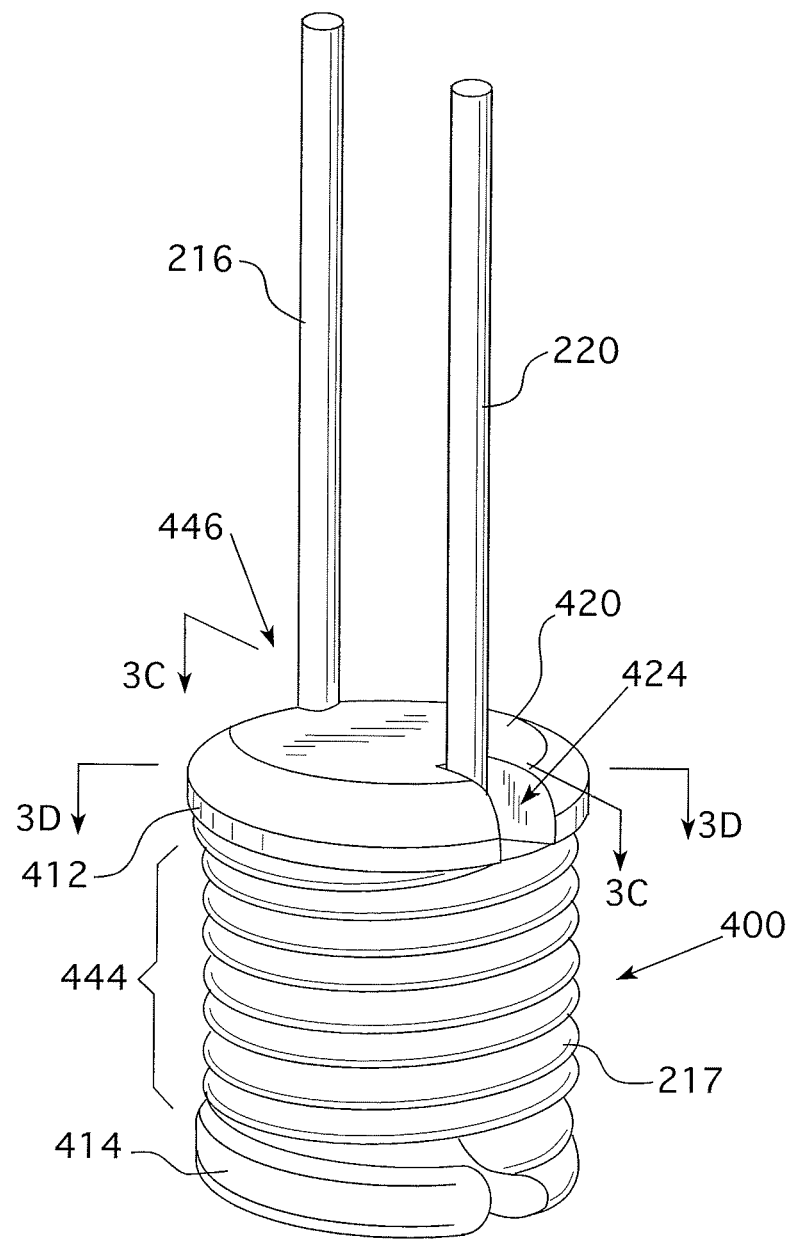
FIG. 3A is an elevational view of a preferred embodiment of a coil assembly according to an embodiment.
Figure 3D:
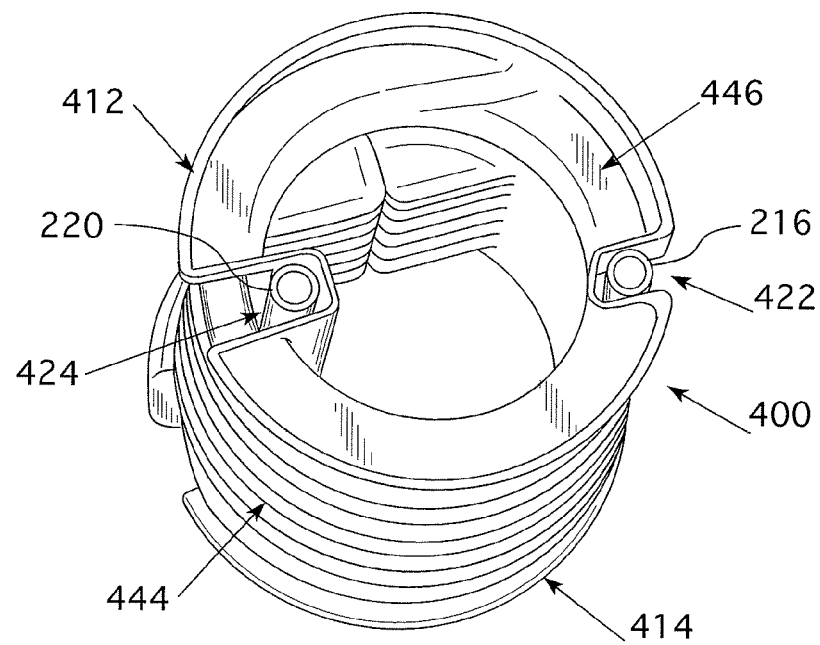
FIG. 3D is a cross-sectional view taken along line 3D-3D of FIG. 3A.

The first trough 107 leads into a second recess or trough 113 that accommodates a second pumping mechanism 180, such as a peristaltic pump, and a T-connector 205 (including check valves 214, 215) of the MPDS 200. As shown in FIG. 1C, the second trough 113 also leads to a first well 111 that accommodates a container access system 600 and a radiopharmaceutical vial or container 902 disposed in a container shield or PIG 554 (discussed in more detail below) and to a second well 121 that accommodates a dose calibrator or ionization chamber 160 for the fluid delivery system 10. As shown in FIGS. 1D and 3F, the ionization chamber 160 preferably accommodates a coil assembly 400 of the MPDS 200 (discussed in more detail below). Although the system is described as including an ionization chamber 160 for detecting activity of the radiopharmaceutical fluid, this is not to be considered as limiting the scope of this disclosure as any suitable activity detector may be used such as, but not limited to, a CZT crystal detector, a Geiger-Müller counter, a scintillating counter, and a parabolic detector, such as the parabolic sensor disclosed in U.S. patent application Ser. No. 12/664,653, which is hereby incorporated by reference.

A third recess or trough 125 extends from the second well 121 to a third well 127 and further along the surface 103 of the fluid delivery system 10. The trough 125 accommodates a T-connector 222 of the MPDS 200, two pinch valves 170, 172, an air detector 174, and a mount or retainer 176 for holding the connector end 228 of the MPDS 200. The pinch valves 170, 172 may be powered and controlled by the fluid delivery system 10, but alternately could be manually-operated. In another alternate embodiment, the pinch valves 170, 172 and the T-connector 222 of the MPDS 200 may be replaced with a manual or automated 3-way stopcock.

The third well 127 accommodates a waste receptacle or bag 224 for receiving medical fluid and/or pharmaceutical that is discarded during, for example, a priming procedure (discussed in more detail below) to prepare the system 10 for an injection procedure.

As shown in FIG. 1C, the SPDS 700 includes a length of tubing (preferably coiled, as shown) having a first end 702 that is attachable to the connector end 228 of the MPDS 200, and a patient end 704 having a luer connector that is attachable to, for example, a catheter (not shown) placed in a venous structure of a patient. As discussed in more detail below, the MPDS 200 may be used for multiple patients but the SPDS 700 is intended to be used on a per-patient basis and discarded after use with a single patient to prevent, for example, cross-contamination between patients.

As can be appreciated after reviewing FIG. 1A-1E, the secondary handle 21 of lid 20 overlies the tubing holder 150 and the mount 176 when the lid 20 and handle 21 are closed to cover the MPDS 200. The secondary handle 21 may be flipped open (from the closed position as shown in FIG. 1A) without retracting the cover 20 to allow an operator to connect the SPDS 700 to the MPDS 200 (as discussed in more detail below). As best shown in FIG. 1C, the SPDS 700 may be placed under the secondary handle 21 when it is closed.

The fluid delivery system 10 further includes the system controller 5 (see FIGS. 1D and 1E) in communication with the various components thereof, including the GUI 15, the pumps 22, 180, the dose calibrator or ionization chamber 160, the interrupt button 25, the air detector 174, the printer 1032, and motors 30, 31 (see FIG. 3F) for pinch valves 170, 172, respectively, for controlling the operation of the system 10. The system controller 5 may be embodied as the computer 1000 as discussed in greater detail hereinabove with reference to FIG. 1F.

As can be appreciated, the wells and troughs formed in the upper surface 103 can be sized, configured, or arranged as suitable for the length, design, or configuration of the MPDS 200 or other components thereof, including the radiopharmaceutical container 902, container shield 554, container access system 600, ionization chamber 160, waste receptacle 224, etc.

It should be understood that FIG. 1C in no way is intended to convey dimensions or relative dimensions of the aforementioned recessed portions or MPDS components; instead, FIG. 1C conveys general positional relationships of such recessed portions with respect to one another.

It should further be understood and appreciated that the recessed portions shown and described with respect to FIG. 1C are encased throughout with suitable radioactive shielding to further minimize exposure to an operator.

Figure 2A:
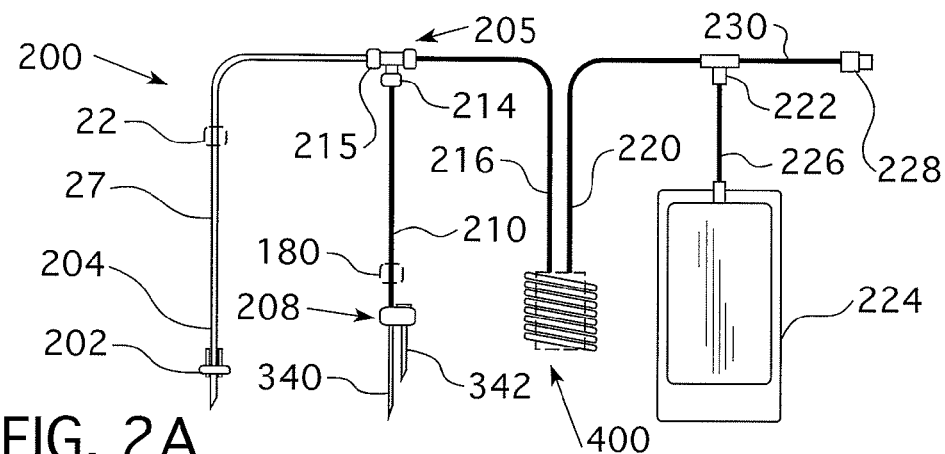
FIG. 2A is a schematic illustration of the multi-patient fluid path set and components thereof according to an embodiment.
Figure 2B:
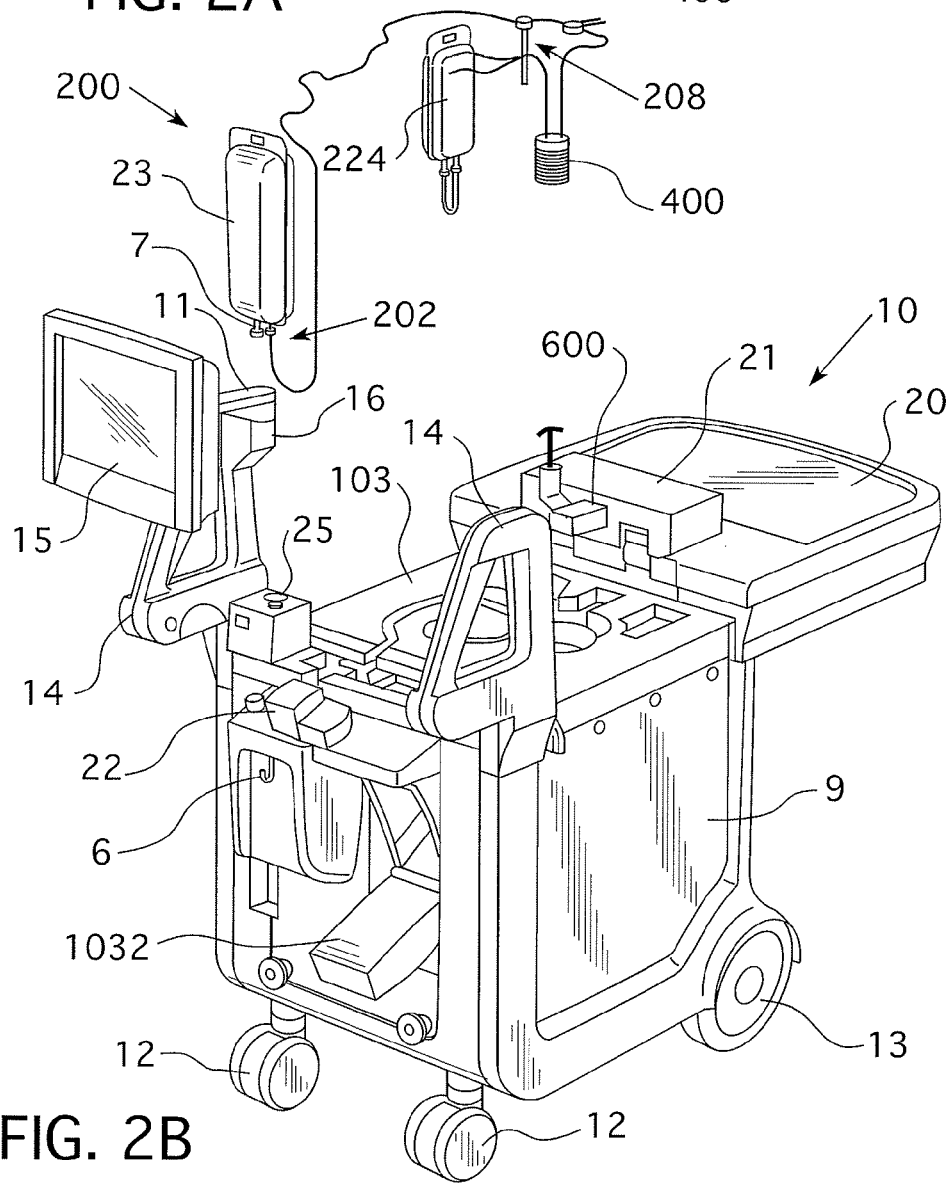
FIG. 2B is an exploded view showing the multi-patient fluid path set shown in FIG. 2A connected to a fluid source and disposed above the fluid delivery system shown in FIGS. 1A-1E.

Turning now to FIGS. 2A and 2B, an embodiment of the MPDS 200 and components thereof will be discussed. In addition, specific details of the coil assembly 400 employed in the MPDS 200 are shown and described with respect to FIGS. 3A-3F and FIG. 1D.

By way of a general overview, the MPDS 200 in accordance with at least one embodiment allows for FDG (or other radiopharmaceutical) to be drawn from a bulk radiopharmaceutical container 902 and placed into a coil assembly 400 that allows an ionization chamber 160 to measure the amount of activity in the coil assembly 400. Once the system prepares a dose having the desired activity level, the fluid delivery system 10 will deliver the FDG dose to the patient (through the SPDS 700).

Generally, the MPDS 200 can be considered in terms of four components: (1) a medical fluid or saline component; (2) an FDG or pharmaceutical component; (3) a coil assembly component; and (4) a waste component. The saline component draws saline out of a bulk source 23 (e.g., via peristaltic pump 22). This is then used to prime the MPDS 200 (i.e., remove air therefrom), position FDG in the coil assembly 400 in the ionization chamber 160, and then deliver the dose to the patient.

The FDG component serves to draw FDG out of bulk radiopharmaceutical container 902 (e.g., via peristaltic pump 180) and place the same into the fluid path to the ionization chamber 160.

The coil assembly component is employed to position the radiopharmaceutical to allow its radioactivity level to be optimally measured by the ionization chamber 160. Through the arrangement of the coil assembly 400 (as discussed in more detail below), the radiopharmaceutical can be optimally oriented and located within the "linear region" of the ionization chamber 160 to more accurately measure its activity level and prepare an optimal dose for injection into a patient.

The waste component holds the saline fluid and/or radiopharmaceutical that are discarded during the prime and dose preparation procedures, which are conducted to prepare the fluid path and the pharmaceutical dose for injection into a patient.

FIG. 2A schematically illustrates the MPDS 200 according to an embodiment. The MPDS 200 shown in FIG. 2A may be pre-connected as shown and may originally be stored in a sterile packet or container for use in an injector apparatus, such as fluid delivery system 10, when desired. For a non-restrictive and illustrative appreciation of a manner in which MPDS 200 can be incorporated in an injector apparatus, simultaneous reference may be made to FIGS. 1A-1E and 2B (and the discussion thereof hereinabove).

Primary components of MPDS 200 include, as shown: a spike 202 for connecting the MPDS 200 to the medical fluid or saline source 23; a vented cannula 208 for connecting with a source of FDG or other radiopharmaceutical; a coil assembly 400; a T-connector 205 with check valves 214, 215 for fluidly connecting the saline source 23, the radiopharmaceutical source, and the coil assembly 400; a waste bag 224; a connector end 228; and a T-connector 222 for fluidly connecting the coil assembly 400, the waste bag 224, and the connector end 228.

In general, MPDS 200 and fluid delivery system 10 are configured for priming (i.e., purging air from) the MPDS 200, delivering pharmaceutical (e.g., FDG) to a patient, and providing a saline flush, while minimizing or eliminating exposure of administering or operating personnel to the detrimental effects of the pharmaceutical and minimizing or eliminating creation of contaminated waste. Moreover, MPDS 200 and other elements disclosed herein also facilitate safe delivery of the pharmaceutical to multiple destinations (for example, dose delivery to a series of patients).

A T-connector 205 and check valves 214, 215 accommodate a first tubing section 204 that is in fluid connection with spike 202 and a second tubing section 210 in fluid connection with cannula 208. The check valves 214, 215 may be integrally formed with the T-connector 205 or may be separate components, or they could be combined into a single dual check valve. The check valves 214, 215 prevent saline from being pumped by peristaltic pump 22 into second tubing section 210 and the pharmaceutical from being pumped by peristaltic pump 180 into the first tubing section 204.

A third tubing section 216 leads to coil assembly 400 (including tube coil 444), and a fourth tubing section 220 leads from the coil assembly 400 to the T-connector 222. As described below, the tube coil 444 is formed from a tubing section 217 that has dimensions different from those of the third tubing section 216 and the fourth tubing section 220.

A fifth tubing section 226 leads from the T-connector 222 to the waste receptacle 224 and a sixth tubing section 230 leads from the T-connector 222 to the connector end 228. As shown above in FIG. 1C, the connector end 228 mates with the first end 702 of the SPDS 700 for delivery of a pharmaceutical to a patient.

The connector end 228 may be a swabable luer valve (Part No. 245204024 provided by Halkey-Roberts Corporation of St. Petersburg, Fla.) that is biased to close or seal off the connector end 228 of the MPDS 200 when the SPDS 700 is not connected thereto. The swabable luer valve prevents the MPDS 200 from being contaminated and allows an operator to swab or clean (by, for example, an alcohol wipe) the connector end 228 prior to connecting an SPDS 700 thereto. Alternately, however, the connector end 228 may be a standard luer connector as known in the art.

As schematically shown in FIG. 2A, the tubing length 27 of the first tubing section 204 can be placed within pump 22 (indicated by dotted lines) to pump saline or other medical fluid from source 23 and a portion of the second tubing section 210 can be placed within pump 180 (indicated by dotted lines) to pump a radiopharmaceutical from a radiopharmaceutical source.

Absolute and relative dimensions of the components shown in FIG. 2A, including tubing, may be chosen to best suit the applications at hand. The first tubing section 204 may be approximately 56.75 inches in length, has an outer diameter (OD) of approximately 0.188 inches and an inner diameter (ID) of approximately 0.062 inches, and has a 45 durometer. The second tubing section 210 may be approximately 8.75 inches in length and is formed of microbore tubing having an OD of about 0.094 inches and an ID of about 0.032 inches and a 45 durometer. The third tubing section 216 may be approximately 15 inches in length, has an OD of approximately 0.163 inches and an ID of approximately 0.062 inches, and has a 60 durometer. The fourth tubing section 220 may be approximately 12 inches in length, has an OD of approximately 0.163 inches and an ID of approximately 0.062 inches, and has a 60 durometer. The fifth tubing section 226 and the sixth tubing section 230 may each be approximately 5 inches in length, have an OD of approximately 0.163 inches and an ID of approximately 0.062 inches, and have a 60 durometer. The tubing in tube coil 444 may be approximately 41 inches in length, has an OD of about 0.218 inches and an ID of about 0.156 inches and an 80 durometer. All of these dimensions are provided for exemplary purposes only and are not to be construed as limiting the present disclosure.

The microbore tubing of second tubing section 210 may be formed of, for example, silicone, C-Flex, or silicone-like PVC material. Essentially, the use of microbore tubing in second tubing section 210 improves volume accuracy and thereby improves measured activity accuracy (i.e., of pharmaceutical delivered to the patient) and reduces radiopharmaceutical waste.

By way of tubing material for the other tubing sections 204, 216, 220, 226, 230 and tube coil 444, essentially any suitable polymeric material, including standard PVC or pump tubing, may be employed.

Referring again to FIGS. 1A-2B, the placement of the MPDS 200 in the fluid delivery system 10 and the connection of the SPDS 700 will now be discussed. To set up the system 10 at, for example, the beginning of the day, the operator lifts the secondary handle 21, grasps the primary handle and latch release 1, and retracts the lid 20 to reveal the upper surface 103 of the system 10. If a used MPDS 200 is present in the system 10, the operator will remove and discard it.

A new MPDS 200 may be removed from its (typically sterile) packaging and placed in the system 10 as shown in FIG. 1C. This includes placing the waste receptacle 224 into well 127, placing coil assembly 400 into ionization chamber 160, placing second tubing section 210 into operative connection with pump 180, placing the tubing length 27 of the first tubing section 204 into operative connection with pump 22 and tubing holder 150, placing vented cannula 208 into fluid connection with radiopharmaceutical source or container 902 located in well 111, placing fifth tubing section 226 in operative connection with pinch valve 170, and placing sixth tubing section 230 in operative connection with pinch valve 172, air detector 174, and mount 176. A saline source 23 may be hung on a hook 6 (see FIGS. 1A, 1B, and 2B) or otherwise mounted on fluid delivery system 10, and spike 202 is inserted into port 7 (see FIGS. 1A, 1B, and 2B) of source 23 to fluidly connect the MPDS 200 to the source 23. Of course, this installation procedure does not need to be completed in the order described above, but may be completed in any suitable order consistent with the description or drawings hereof.

After the MPDS 200 is installed and primed (as discussed below), the first end 702 of the SPDS 700 is connected to the connector end 228 of the MPDS 200 and the SPDS 700 is primed to provide a wet connection at the patient end 704 of the SPDS 700, which is then connected to a catheter (not shown) located in a patient. The SPDS 700 may be a coiled tubing formed of standard PVC, approximately 60 inches in length and having an OD of approximately 0.100 inches and an ID of approximately 0.060 inches and a 90 durometer.

As shown in FIGS. 2A and 2B, the MPDS 200 includes a coil assembly 400. In the broadest sense, coil assembly 400 may include a section of tubing (including portions of third and fourth tubing sections 216, 220) that is simply gathered (in a coiled or an uncoiled, amorphous fashion) and placed inside ionization chamber 160.

As shown in FIGS. 3A-3F, however, a more desirable embodiment of coil assembly 400 includes a (preferably thermoformed) core element or structure 446 that is preferably configured for allowing tubing section 217 to be wrapped thereupon and to assume the coiled tube section indicated at 444. As such, the coiled tube section or tube coil 444 may be formed on the core element 446 to facilitate optimal positioning of the tube coil 444 within the ionization chamber 160.

To facilitate positioning of the tube coil 444, the core element 446 may include a tube channel 410 defined by shoulders 412, 414 (see FIG. 3B) that retain tube coil 444 therebetween to hold the tube coil 444 in position and to prevent tube kinking. Further, the upper surface 420 of core element 446 defines an inlet channel or groove 422 and an outlet channel or groove 424 to accommodate third tubing section 216 and fourth tubing section 220, respectively.

The core element 446 preferably may be self-centering when inserted into the sleeve 162 of the ionization chamber 160 of the fluid delivery system 10 to thereby facilitate optimal performance (see FIG. 3F). This may be achieved either through structural features of the coil assembly 400, the structure of core element 446 itself, or a combination thereof when used with the sleeve 162 of the ionization chamber 160.

Figure 3E:
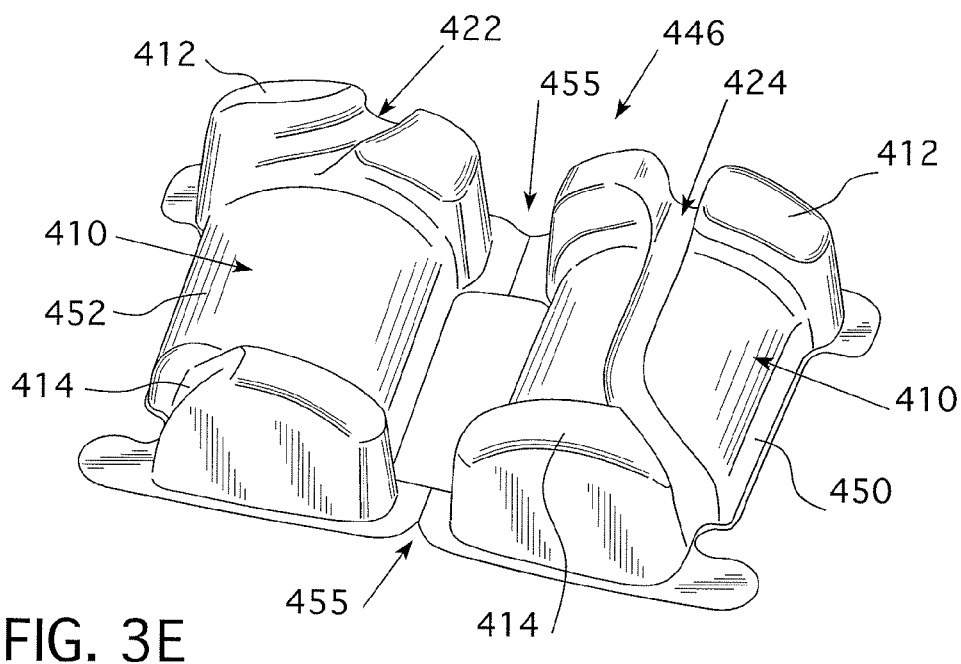
FIG. 3E is a perspective view of the core element of the coil assembly shown in FIG. 3A.
Figure 3F:
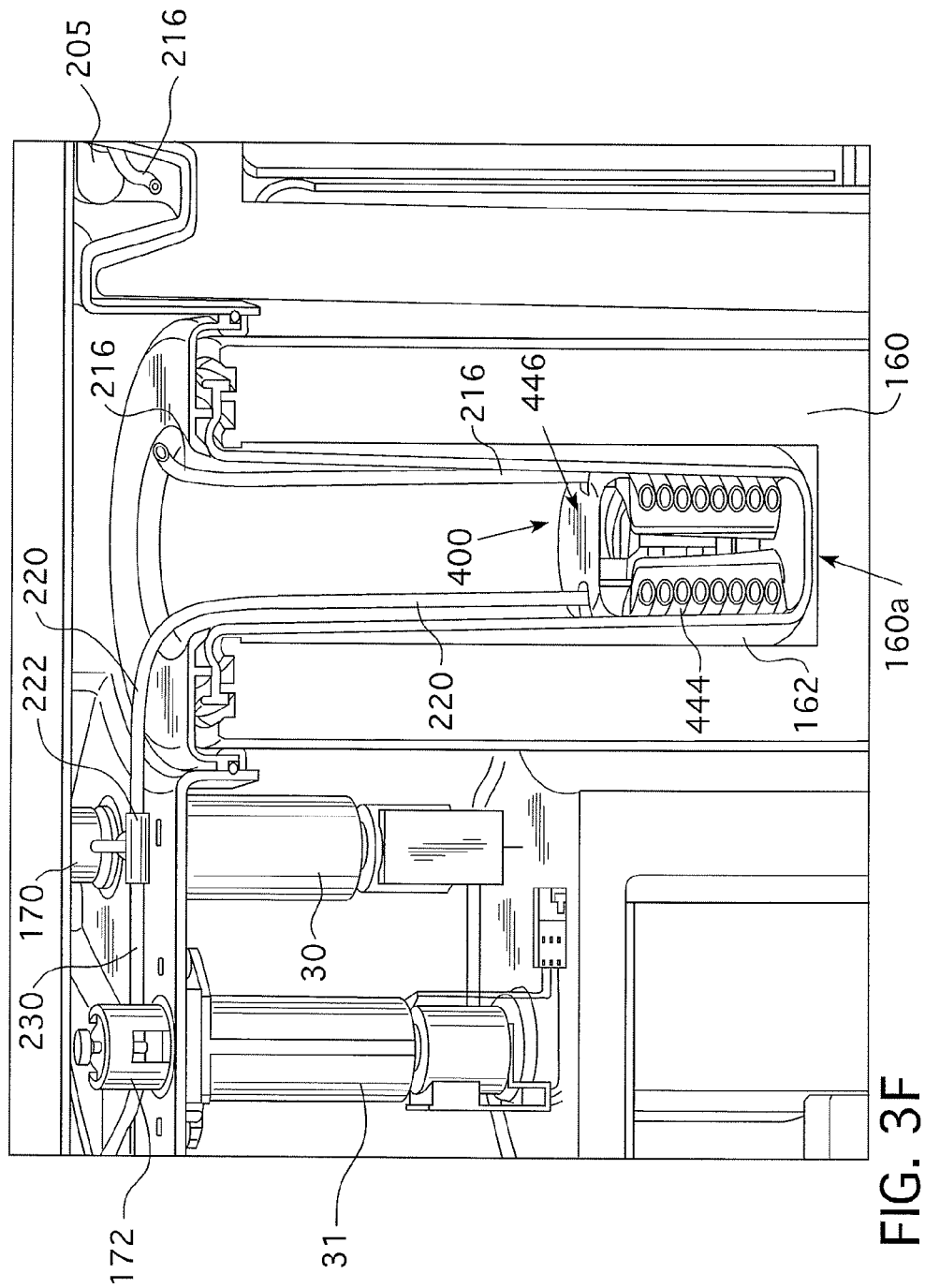
FIG. 3F is an enlarged view of FIG. 1D showing the coil assembly in the ionization chamber of the fluid delivery system.

As best shown in FIG. 3E, the core element 446 may be formed by folding two elements (450, 452) together along an integral hinge 455. Suitable form-locking mechanisms can be molded onto the core element 446 to facilitate clasping of the elements 450, 452 together.

FIGS. 1C, 1D, and 3F show coil assembly 400 positioned concentrically in the sleeve 162 of the ionization chamber 160. The core element 446 and the tube coil 444 are sized and dimensioned so that the coil assembly 400 is optimally positioned within the "linear region" of the ionization chamber 160 so that the ionization chamber 160 can accurately determine the activity level of one or more volumes of radiopharmaceutical that is located within the tube coil 444. The "linear region" of an ionization chamber is the region in which activity level measurements are repeatable and predictable. For an exemplary ionization chamber (Model IK-102 Short Ionization Chamber provided by Veenstra Instruments) used in system 10, the "linear region" is located within a window of 5 mm to 65 mm measured from the base or bottom wall 160a of the ionization chamber 160 (see FIG. 3F).

The tube coil 444 may be comprised of approximately 7 turns (see FIGS. 3A and 3B) formed from a length of tubing that is approximately 41.0 inches. As shown in FIG. 3B, the height h of the tube coil 444 is approximately 1.53 inches and the diameter w of the tube coil 444 is approximately 1.95 inches. The tube coil 444 is preferably formed from a tube having an OD of 0.218 inches and an ID of 0.156 inches. Further, based on the length and ID of the tubing, the tube coil 444 preferably has a volume capacity of approximately 12.5 ml.

As discussed heretofore, a source, container, or container 902 (see FIG. 4C) of a pharmaceutical or radiopharmaceutical is placed into the fluid delivery system 10 (e.g., in well 111 formed in upper surface 103) to prepare and perform an injection procedure. A radiopharmaceutical container or container 902 is typically placed in a conventional container shield or PIG 554 for transport by personnel.

Turning now to FIGS. 4A and 4B, an exemplary embodiment of a container shield carrying device or system 500 and a container access system 600 are shown. Container access system 600 is removably disposed within well 111 of fluid delivery system 10 and operates to hold container shield 554 and to access the contents of the container 902 contained therein.

As best shown in FIG. 4A, the container shield 554 (containing a radiopharmaceutical container 902) includes a flange 504 formed along a top end thereof and a removable septum cap 562 that is securely and removably engaged with the container shield 554 (e.g., via threading) to allow insertion and removal of the container 902 therefrom.

As shown in FIGS. 4A and 4B, the carrying system 500 includes a collar unit 502 that removably engages the flange 504 formed on the container shield 554. The collar 502 may be formed in two pieces 506, 508 that are pivotally connected together (e.g., at one end thereof) to allow the collar 502 to engage and disengage the flange 504.

The collar 502 includes two elongated slots 510 formed in a top surface therein. As best shown in FIG. 4B, the slots 510 each include a pin 512 disposed therein and extending between two opposing walls 514 thereof.

The carrying system 500 further includes a handle unit 520 that engages with the collar unit 502 and the septum cap 562 to allow the container shield 554 (and container 902) to be carried and installed in the fluid delivery system 10. The handle unit 520 includes a handle 556 that is rigidly connected to a generally U-shaped cross piece 564a. The cross piece 564a defines two downwardly extending arms 530 having slots 532 formed thereon.

The slots 532 each form a slight hook on the ends thereof and are adapted to engage and retain a second cross piece 564b that supports a plunger 566 having a generally frustoconical shape that mates with a generally frustoconical recess of the septum cap 562 (see FIG. 4B).

The second cross piece 564b is also generally U-shaped and defines two downwardly extending arms 534 having hooks 536 formed therein. The open ends of the hooks 536 are formed on opposite ends of the arms 534 and are adapted to accept and retain the pins 512 in slots 510 of collar 502. The slots 510 are sized to provide sufficient clearance for the arms 534 to be inserted thereinto (in a downward direction) and for the hooks 536 to engage pins 512 (through rotation of handle 556).

The plunger 566 is connected to the second cross piece 564b by means of a connector (such as a screw 540) and a spring 538. The plunger 566 is biased by spring 538 to ensure a tight fit between the plunger 566 and the septum cap 562.

To engage and carry the container shield 554, the collar 502 is connected to the flange 504 of the container shield 554 as described above. The handle unit 520 is then moved into proximity to the container shield 554 (by an operator grasping the handle 556 and moving the unit 520 into position) and the arms 534 are lowered into the slots 510 of the collar 502. At substantially the same time, the plunger 566 is engaged with the septum cap 562, with the spring 538 ensuring a tight fit between the two. The operator then turns the handle unit 520 in a clockwise direction (see arrow AA in FIG. 4A) to seat the pins 512 in slots 510 into the hooks 536 of arms 534.

The operator then lifts the combined container shield 554 and container carrying system 500 (by moving the handle unit 520 in an upward direction) and transports it to, for example, the fluid delivery system 10. The operator then lowers the container shield 554 into the container access system 600 disposed in well 111 (see FIG. 4A) and rotates the handle unit 520 in a counter-clockwise direction to disengage the hooks 536 from the pins 512. The operator then lifts the handle 556 in an upward direction to remove the arms 534 from the slots 510 and the plunger 566 from the septum cap 562, thereby leaving the container shield 554 (with septum cap 562 and collar 502) in container access system 600 in well 111 (see FIG. 4B).

In an exemplary embodiment, the plunger 566 includes radioactive shielding (such as lead) to shield the operator from radiation that would otherwise leak through or be emitted from the septum of the septum cap 562. Together with the container shield 554 and the septum cap 562, the plunger 566 of the container carrying system 500 shields the operator from the radiation emitted by the radiopharmaceutical and prevents unnecessary radiation exposure. Further, by extending the handle 556 from the container shield 554, the distance between the two functions to lessen any possible radiation exposure to the operator.

As discussed above with respect to FIGS. 4A-4B, the fluid delivery system 10 includes a container access system 600 that is removably disposed within well 111 of fluid delivery system 10 and is adapted to hold container shield 554 and to provide access to the contents of the container 902 within container shield 554.

Because containers (such as container 902 described herein) typically come in various sizes, such as 10 ml, 15 ml, 20 ml, and 30 ml, the fluid delivery system 10 is intended to accommodate various container sizes. To do so, the fluid delivery system 10 may include one or more container shields and container access systems. Thus, depending on the size of the container used at a clinical site or for a particular procedure, an operator of the fluid delivery system 10 can select the appropriate container shield and container access system and place it in the well 111 of the fluid delivery system to enable a fluid injection procedure.

Referring again to FIGS. 1C and 2A, once the MPDS 200 is installed in the fluid delivery system 10, the spike 202 is placed in fluid connection with the saline source 23 and the cannula 208 is inserted into the container 902 and placed in fluid connection with the pharmaceutical therein, and an injection procedure can be implemented.

An exemplary injection procedure is discussed hereinafter with reference to FIGS. 5-11. Many variations on the injection procedure may be implemented within the scope of this disclosure. For instance, the container 902 of radiopharmaceutical may be any suitable multi-dose container configuration. This multi-dose container configuration may include a dose of radiopharmaceutical for a plurality of patients provided in any suitable container for storing radiopharmaceuticals. The multi-dose container configuration may include a dose of radiopharmaceutical for a plurality of patients provided in a syringe. In addition, the multi-dose container configuration may be a plurality of containers suitable for storing radiopharmaceuticals where each container stores a certain amount of a radiopharmaceutical composition. A micro-fluidic device or other radiopharmaceutical generation technology capable of real-time generation of a certain amount of a radiopharmaceutical may also be utilized as the multi-dose container configuration. Furthermore, the multi-dose container configuration may be a plurality of suitable containers each holding a different radiopharmaceutical fluid. The multi-dose container configuration may also be a pre-loaded amount of radiopharmaceutical fluid in a coil of tubing of an administration set. Alternatively, a single dose container may also be utilized. Accordingly, the injection procedure described hereinafter is not to be construed as limiting this disclosure and while a container 902 is described hereinafter, this is not to be construed as limiting as any variety of radiopharmaceutical container may be used. Furthermore, the following procedure describes the use of a first volume, bolus, or slug 800 and a second volume, bolus, or slug 802 of radiopharmaceutical delivered to a patient. This also is not to be construed as limiting injection processes to the injection procedure disclosed herein as any suitable number of slugs may be delivered to the patient.

An exemplary injection procedure can generally be divided into five phases. In an initialization phase 910, the device is brought into a well-defined initial state. In a calibration phase 920, steps are performed for calibrating the radioactivity in container 902. In a delivery phase 930, the radiopharmaceutical is delivered to the destination. In a step 940, it is decided whether another injection shall be performed. If yes, operation will continue again with the calibration phase 920. If no, a shutdown phase 950 will follow.

Before starting the operation, the operator will have to determine two quantities: the desired activity Ar to be injected to the patient; and the estimated concentration of activity in the container (activity per unit of volume, e.g., expressed in MBq/ml) Cv. These data are provided to the system controller 5. Operation then starts with the initialization period 910.

Figure 5:
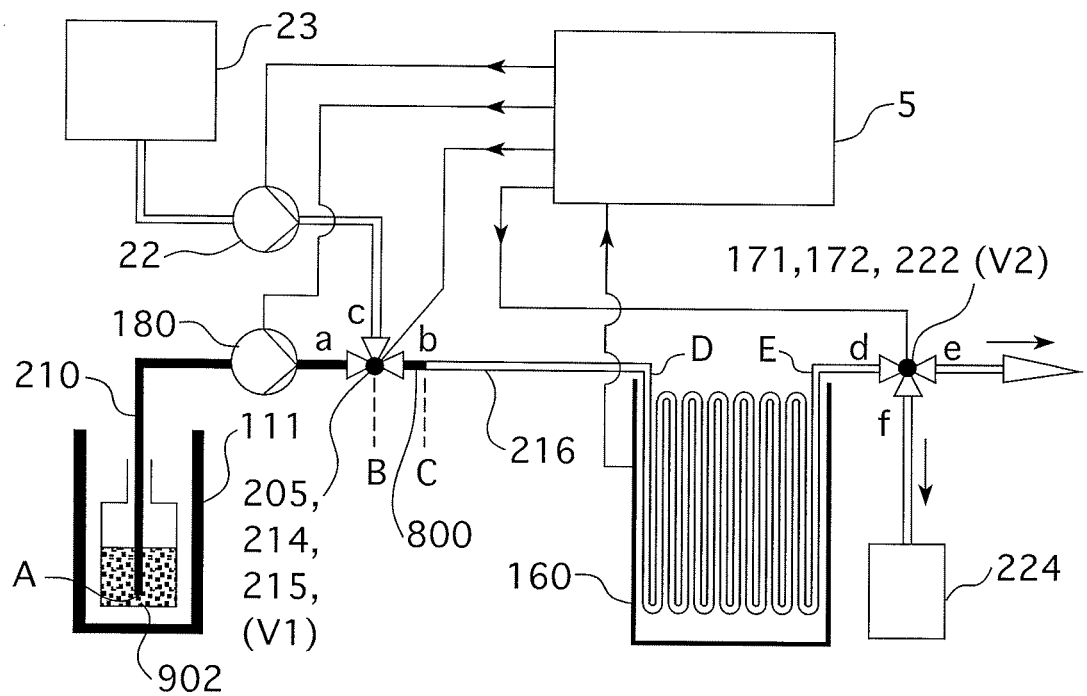
FIG. 5 is a simplified schematic illustration of the fluid delivery system of FIG. 1A in a first state of operation according to an embodiment.

The initialization period 910 comprises the following steps:

Step 911 (Initial filling of radiopharmaceutical to point C): In a first step, the complete tubing is filled with saline, thereby excluding air from the tubing system. For this, T-connector 205, check valve 214, and check valve 215 (hereinafter valve V1) are placed in a state that connects ports "c" and "b", while T-connector 222, pinch valve 170, and pinch valve 172 (hereinafter valve V2) are placed in positions "d" and "e". Pump 22 flushes saline up to point B (see FIG. 5). Then the tubing section 210 is inserted into a container containing saline. Valve V1 is brought into a state that connects ports "a" and "b", while valve V2 still connects "d" and "e". Pump 180 now flushes saline until the tubing is completely filled with saline from point A (see FIG. 5) to the destination beyond valve V2, and air is thus completely purged from the system. The tubing section 210 is then inserted into the container 902 containing the radiopharmaceutical. Valve V1 is brought into a state that connects ports "a" and "b", while valve V2 connects ports "d" and "f". Pump 180 is operated to pump radiopharmaceutical in container 902 from inlet point A and past point B at valve V1 to some point C in the third tubing section 216. The volume of radiopharmaceutical between points B and C in the third tubing section 216 does not need to be known exactly; it suffices to ensure that the section of tubing from A to B is filled completely with radiopharmaceutical, and that the activity in the volume between B and C is not larger than the desired end activity Ar. The situation at the end of step 911 is illustrated in FIG. 5, where the volume of radiopharmaceutical between points B and C is designated by reference number 800.

Figure 6:
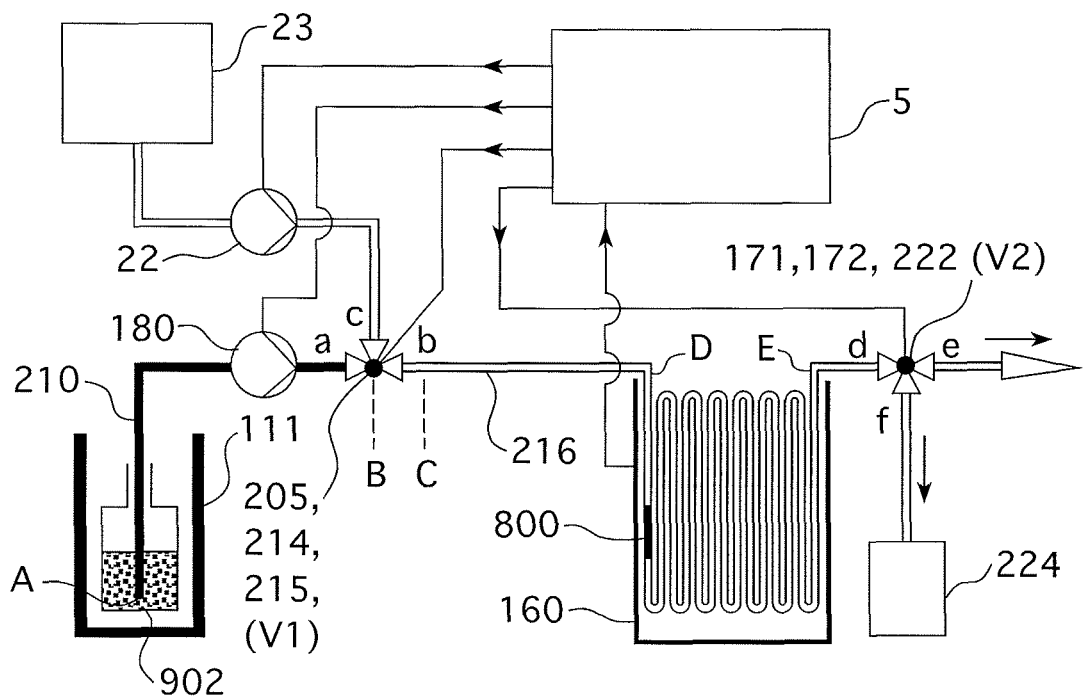
FIG. 6 is a simplified schematic illustration of the fluid delivery system of FIG. 1A in a second state of operation according to an embodiment.

Step 912 (Flushing of offset volume to dose calibrator): Valve V1 is now switched to a state in which it connects ports "c" and "b". Pump 22 is operated to pump saline from the source 23 towards valve V1. The volume to be pumped is slightly larger than the volume in the third tubing section 216, i.e., slightly larger than the volume between points B and D. This volume need not be known exactly. Thereby, the "offset volume" 800 is moved into the coil section 444. The situation at the end of this step is illustrated in FIG. 6.

Step 913 (Initial determination of activity): The activity of volume 800 in the coil section 444 is measured by the ionization chamber 160 (measurement M1). This activity will be called the "offset activity" A1. The system controller 5 now calculates the missing activity Am required to reach a total activity of Ar as shown in Equation 1 hereinafter:

$$Am = Ar - A1 \qquad \text{(Equation 1)}$$

Figure 11:
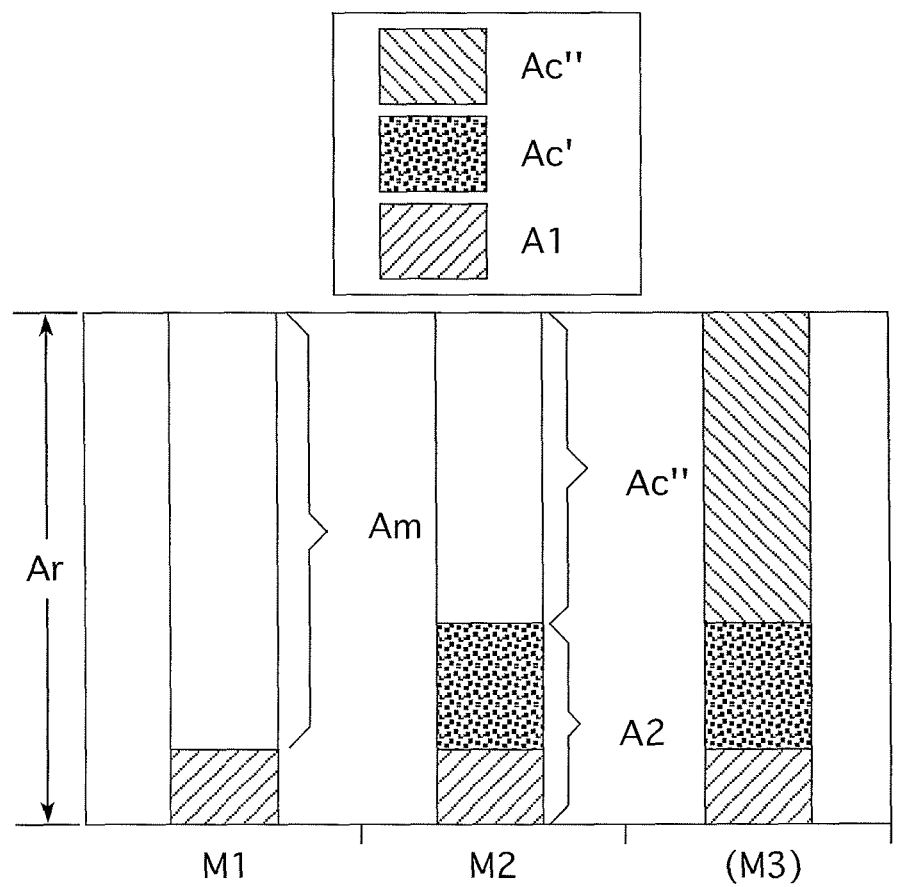
FIG. 11 is a bar graph showing the levels of activity measured in various stages of an injection procedure according to an embodiment.

This is illustrated in FIG. 11 in the leftmost column. From this and the estimated concentration of activity in the container, Cv, the estimated missing volume Va1 still to be delivered is calculated as shown in Equation 2 hereinafter:

$$Va1 = \frac{Am}{Cv} \qquad \text{(Equation 2)}$$

It is important to note that this calculation is still based on the estimate of the concentration of activity in the container, and the result cannot be expected to be highly accurate. It is further important to note that no knowledge about the offset volume 800 is required in this calculation. In addition, ionization chamber 160 may be any suitable activity detector. Such detectors include standard Geiger-Müller counters, scintillating counters, an ionization chamber, a cadmium zinc telluride (CZT) crystal detector, etc., which should be calibrated to yield a sufficiently precise measure of the actual activity in the coil section 444. Desirably, the activity detector is an ionization chamber.

Figure 7:
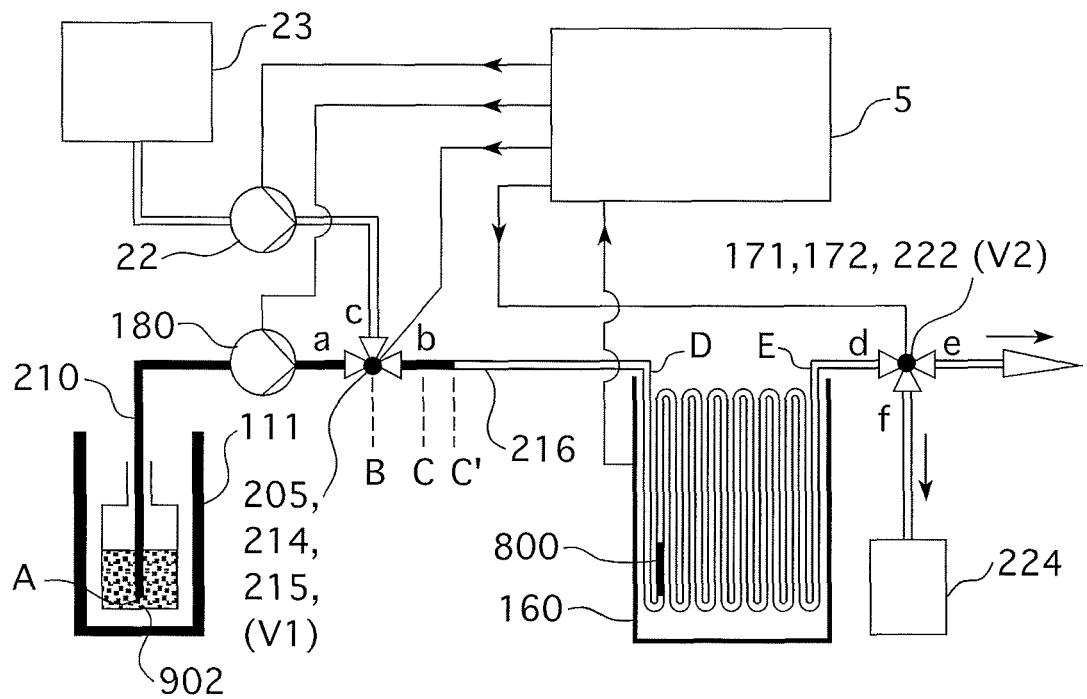
FIG. 7 is a simplified schematic illustration of the fluid delivery system of FIG. 1A in a third state of operation according to an embodiment.

This step concludes initialization 910. In the following calibration phase 920, the following steps are performed:

Step 921 (Filling of radiopharmaceutical to point C): Valve V1 is switched to a state in which it connects ports "a" and "b". Pump 180 is operated to pump a volume Vc' through valve V1, filling the fill-in section to point C. This situation is illustrated in FIG. 7, where this volume is designated by reference number 802. Volume Vc' is chosen to be approximately half of the estimated missing volume Va1 as set forth hereinafter in Equation 3:

$$Vc' \approx \frac{Va1}{2} \qquad \text{(Equation 3)}$$

It is important to note that volume Vc' is known exactly in system internal units. The exact nature of these units depends on the type of pump used, e.g., the units could be pump revolutions, pump cycles, etc. If a volume flow meter is placed in-line with the pump, the units provided by the flow meter can be used as system internal units. Depending on the type of pump and the type of tubing, the resolution of volume in this step can be very small, and even small volumes can be delivered accurately. In addition, the predictive flow rate determination system as discussed in greater detail hereinafter may be used as system internal units.

Figure 8:
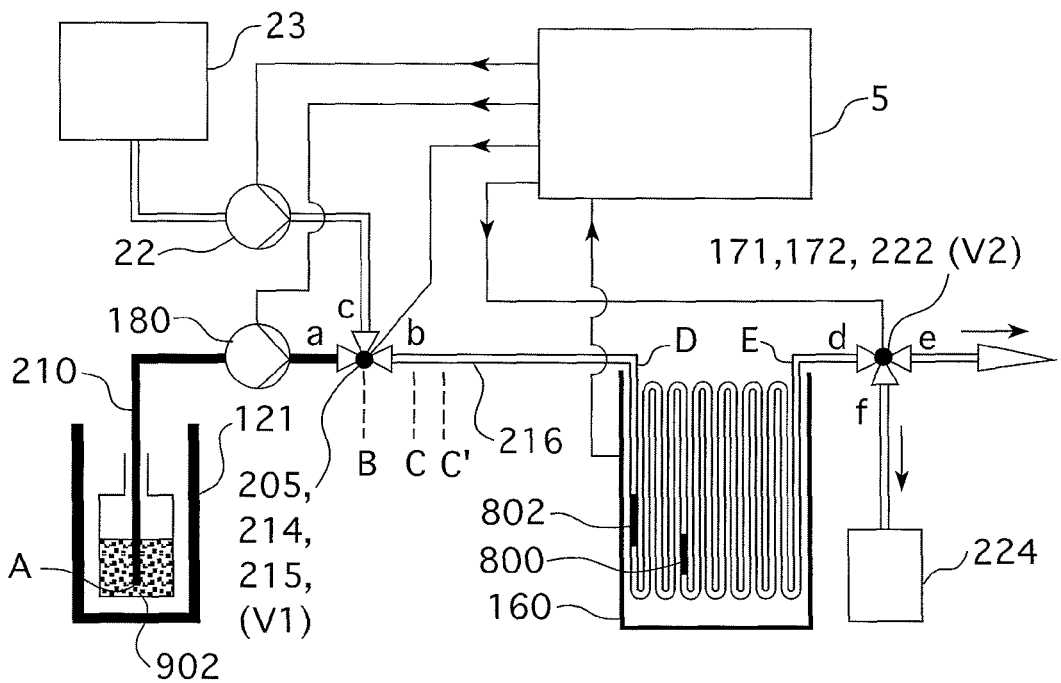
FIG. 8 is a simplified schematic illustration of the fluid delivery system of FIG. 1A in a fourth state of operation according to an embodiment.

Step 922 (Flushing of volume Vc' to the ionization chamber 160): Valve V1 is switched to connect ports "c" and "b". Pump 22 is operated to pump slightly more than the volume between points B and D of saline through valve V1. Thereby, volume 802, which is equal to Vc', of radiopharmaceutical is moved into the coil section 444. The situation at the end of this step is illustrated in FIG. 8.

Step 923 (Calibration of activity): The activity in the coil section 444 is measured by the ionization chamber (measurement M2). This activity level will be called A2. It corresponds to the sum of the offset activity A1 and the activity of the volume Vc', which will be called the "reference activity" Ac'. This is illustrated in the second column of FIG. 11. Now the activity concentration in the container in system internal units, Cs, is calculated as set forth hereinafter in Equation 4:

$$Cs = \frac{Ac'}{Vc'} = \frac{(A2-A1)}{Vc'} \qquad \text{(Equation 4)}$$

The system is now calibrated in system internal units. Thereafter the volume Vc" is determined. The activity Ac" still required to reach a total activity of Ar is determined as set forth in Equation 5:

$$Ac''=Ar-A2 \qquad \text{(Equation 5)}$$

From this, the volume Vc" still to be delivered is calculated in system internal units as set forth in Equation 6 hereinafter:

$$Vc'' = \frac{Ac''}{Cs} = \frac{(Ar-A2)}{Cs} = \frac{(Ar-A2)}{(A2-A1)Vc'} \qquad \text{(Equation 6)}$$

Figure 9:
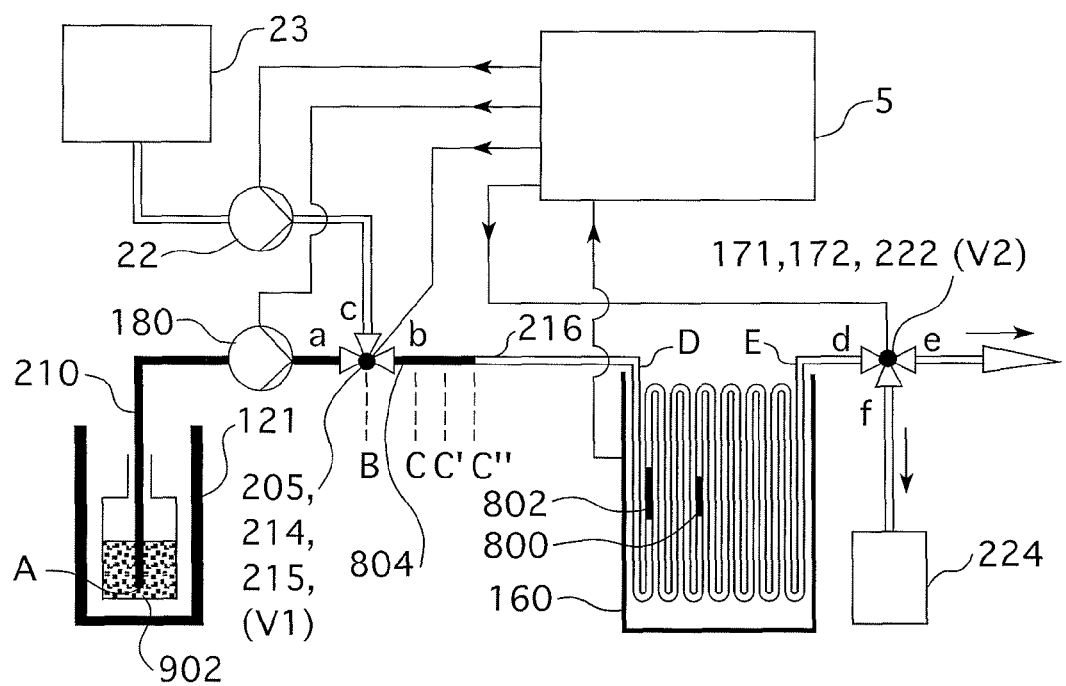
FIG. 9 is a simplified schematic illustration of the fluid delivery system of FIG. 1A in a fifth state of operation according to an embodiment.
Figure 10:
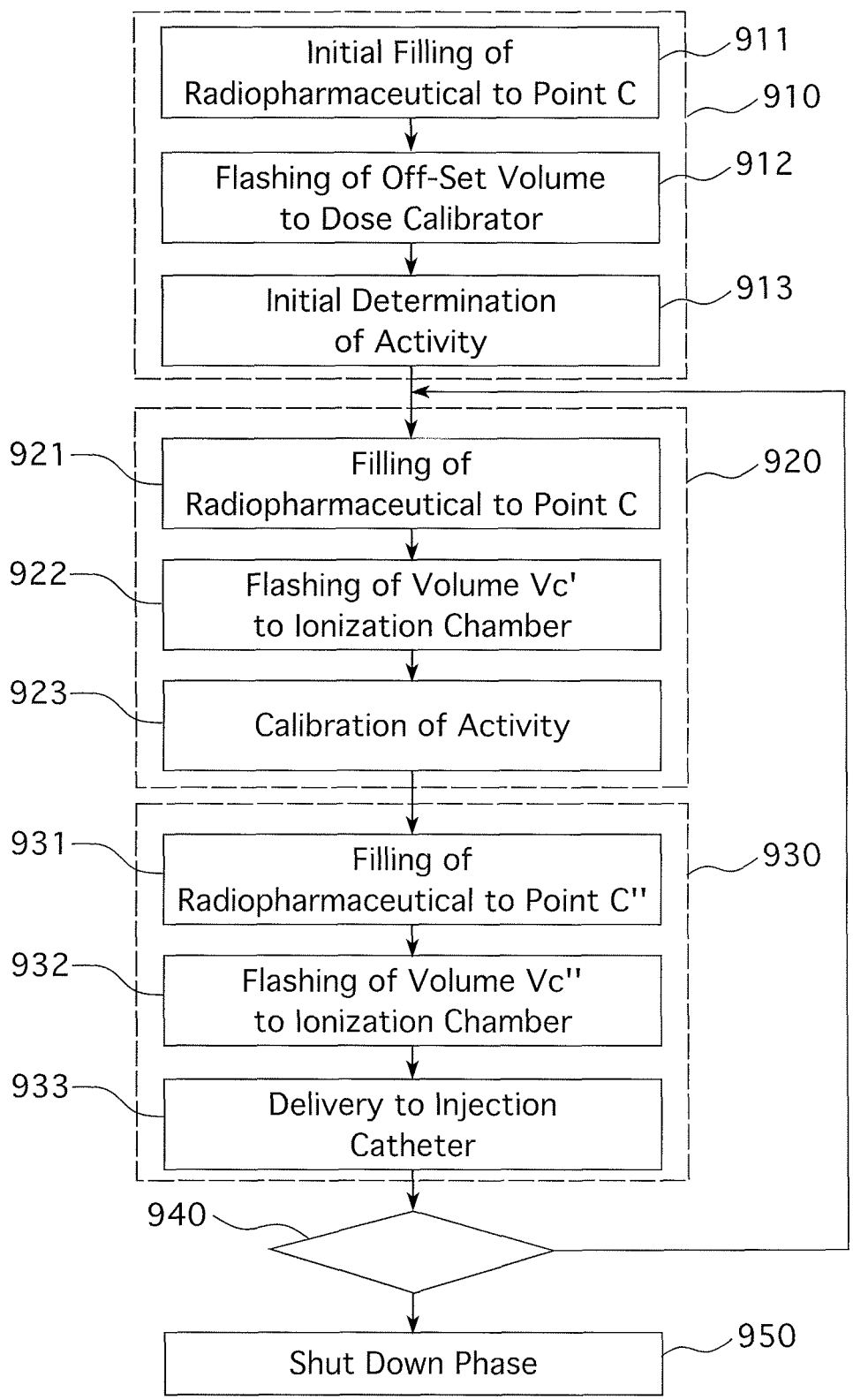
FIG. 10 is a flow diagram of a process for implementing an injection procedure according to an embodiment.

This completes the calibration phase 920. In the following delivery phase 930, the following steps are performed:

Step 931 (Filling of radiopharmaceutical to point C"): Valve V1 is switched to a state in which it connects ports "a" and "b". Pump 180 is operated to pump the volume Vc" through valve V1, filling third tubing section 216 to point C". This situation is illustrated in FIG. 9, where this volume is designated by reference number 804.

Step 932 (Flushing of volume Vc" to ionization chamber 160): Valve V1 is switched to connect ports "c" and "b". Pump 22 is operated to pump slightly more than the volume between points B and D of saline through valve V1. Thereby, volume 804, which is equal to Vc", of radiopharmaceutical is moved into the coil section 444. Alternatively, the total activity in the coil section 444 is now measured (optional measurement M3, see right column of FIG. 11). It should correspond exactly to the total desired activity Ar, provided that the volume of the coil section 444 is large enough to hold all three volumes 800, 802, and 804 within this section. The latter condition can always be fulfilled if the volume of the coil section 444 is at least five times the volume of the third tubing section 216. If a significant discrepancy is detected, the system is stopped.

Step 933 (Delivery to injection catheter): Valve V2 is switched to connect ports "d" and "e". Pump 22 is operated to pump at least the volume of the coil section 444, plus the volume of the tubing from the coil section 444 to the injection catheter and of the injection catheter itself, of saline through valve V1. Thereby, all liquid in the coil section 444 is flushed to the patient, and exactly the required dose of radioactivity is delivered to the patient.

This completes the delivery phase 930. If another injection of the same radiopharmaceutical (to the same or a different patient) is required, operation continues by repeating the calibration and delivery phases 920 and 930. Otherwise, operation stops by a suitable shutdown procedure, which may involve additional cycles of flushing with saline.

When repeating calibration phase 920, no additional initialization as in phase 910 is necessary, since the coil section 444 has been flushed with saline, and the radiopharmaceutical extends exactly to point B. No activity is present in the coil section 444. Therefore, in the above calculations, A1 can be set to zero in this case, and Am is set to Ar. No further changes are necessary. The three-phase procedure with phases 910, 920, and 930 now simplifies to a two-phase procedure with phases 920 and 930 only.

It will be appreciated that the various embodiments of the disclosed device and the associated methods of operation provide a number of inherent safety features. Specifically, there is a high degree of redundancy in the operation of the device, such that even in case of failure of one component, such as a pump or a valve, it is impossible that more than the desired dose will be delivered to the patient. Specifically, by its design the system will only allow the dose present within the coil section 444 to be delivered to the patient. This is because during the actual delivery of the radiopharmaceutical, there is no connection between the container 902 and the fluid delivery line. The discrete nature of the sequential measurements of activity within the coil section 444 is another feature which increases safety. In step 932, the activity in the coil section 444 is actually known beforehand, and measurement M3 just serves to confirm that the right amount of activity is present in the coil section 444. If significant discrepancies are detected between the expected result and the actual measurement, operation will be stopped immediately, and an alarm will be given.

It will also be appreciated that, in normal operation, no radiopharmaceutical will enter the waste reservoir 224. Thus, generation of radioactive waste is minimized.

The disclosure now turns to particular embodiments, as illustrated in FIGS. 12-23, that could conceivably be employed in programming and operating a fluid delivery system as broadly contemplated herein.

Figure 12:
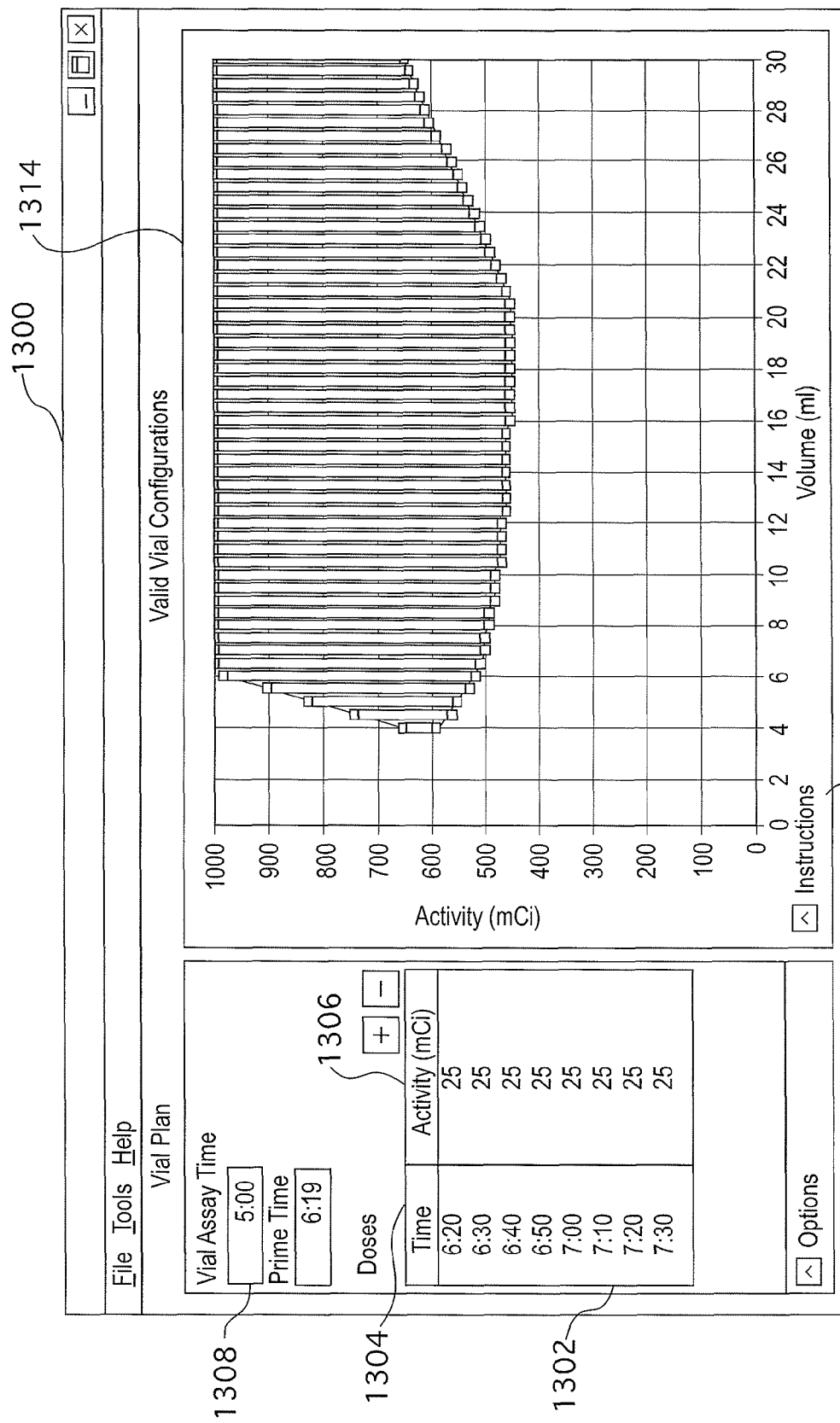
FIGS. 12-18 are various depictions of a display of a computer running software for planning multi-dose radiopharmaceutical usage on radiopharmaceutical according to an embodiment.

With reference to FIGS. 12-18, screen captures of a program used for determining a multi-dose container configuration that meets a planned patient schedule with a sufficient margin to account for reasonable schedule variation while minimizing multi-dose container cost are illustrated. Upon initiating the multi-dose container planning software on a computer, such as computer 1044, a clinician will be presented with a screen 1300 as illustrated in FIG. 12. A schedule 1302 is then provided as input to the multi-dose container planning. This schedule 1302 represents the patient load expected to be serviced by a multi-dose radiopharmaceutical container, such as container 902. The schedule 1302 may include the time of an injection procedure (entered into the column 1304 labeled time) for each patient, and an activity (entered in the column 1306 labeled activity) removed from the multi-dose container 902 of radiopharmaceutical for each patient.

The schedule 1302 may be entered by: manually entering time and activity for each patient into the computer 1044 using an input device, such as a keyboard; retrieving the time and activity for each patient from a memory device associated with the computer; or retrieving the time and activity for each patient from a remotely located patient device over a network. While the a computer may be used to enter the schedule 1302, this is not to be construed as limiting the present disclosure as any suitable computing device, such as, but not limited to, a cellular phone, a Personal Digital Assistant (PDA), or the control system 5 of the injector, may be utilized to enter the schedule 1302. In addition, while schedule 1302 has been described hereinabove as the schedule of injection procedures for a day. This is not to be construed as limiting the present disclosure as any period of time may be used such as a week, a month, or a year.

The Time of Prime block 1308 allows the clinician to enter a time, preferably immediately before the first scheduled patient, at which the clinician will be preparing the fluid delivery system 10 for use as described hereinabove. At this time, a small amount of activity may be removed from the container 902 to validate the container 902 contents or for the automatic injection system to remove air from the MPDS 200 and the SPDS 700. The activity associated with this action is not provided by the clinician.

Once the clinician has entered the schedule 1302 and entered the time of priming using the Time of Prime block 1308, the clinician presses the update chart button 1310. With specific reference to FIG. 13, the update chart button 1310 allows the processor of the computer 1044 to run an algorithm to determine various valid container configurations and plots these container configurations as blocks 1312 on graph 1314. The x-axis of the graph may be volume of the container 902 and the y-axis may be activity of the radiopharmaceutical fluid within the container 902. For instance, point 1316 would represent a container having a volume of 20 mL and containing a radiopharmaceutical fluid having an activity level of 700 mCi.

Figure 13:
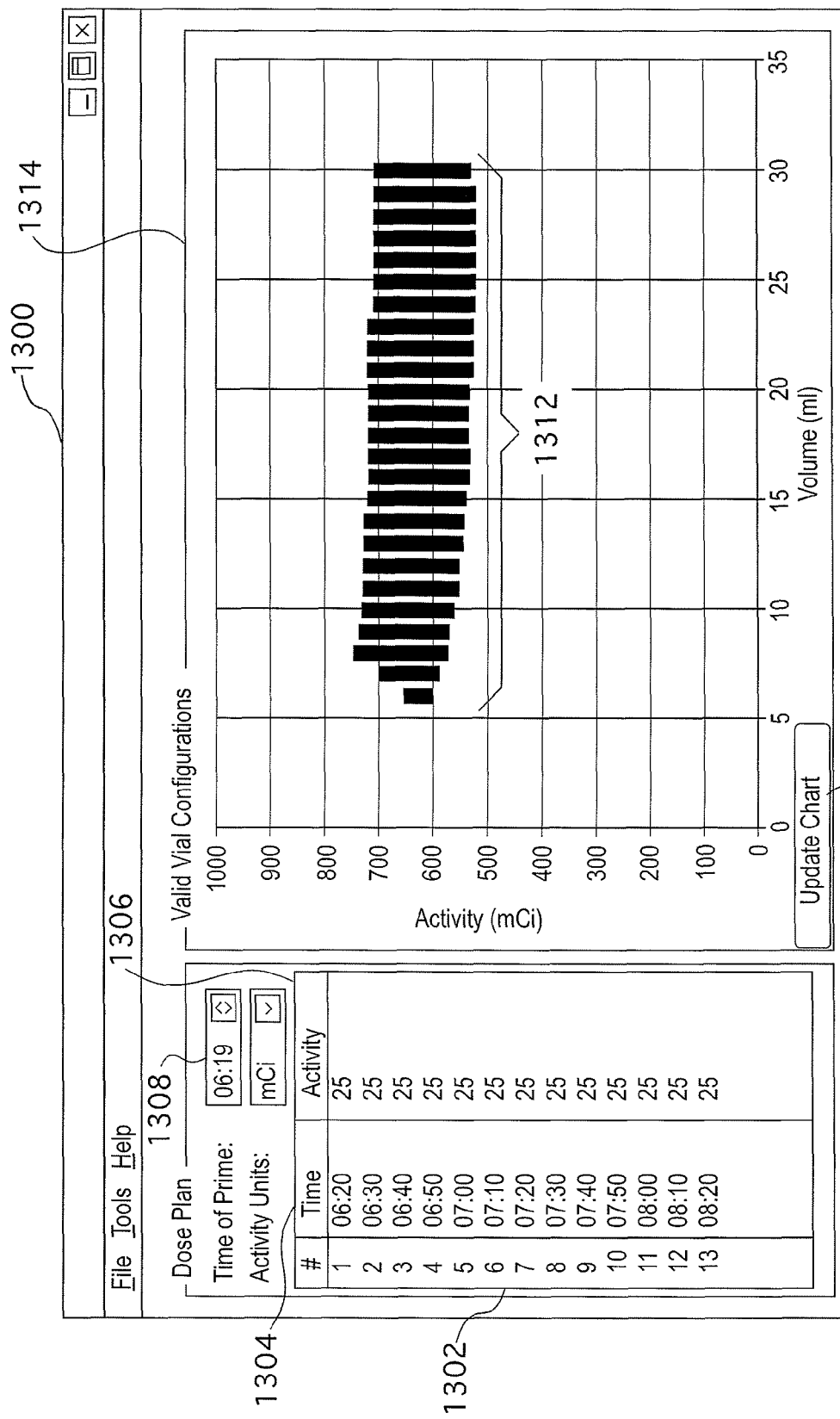

The system determines the correct placement of blocks 1312 on graph 1314 as follows. A radiopharmaceutical container order is typically specified with four parameters: (1) radiopharmaceutical/radioisotope; (2) assay time; (3) assay volume; and (4) assay activity. The radiopharmaceutical is generally set by the application (e.g., FDG for PET). The assay time is the time at which the container contains the specified assay activity. The assay time is generally prescribed based on normal delivery schedules and can be defined by the clinician. The unknown factors that must be determined are the assay volume and assay activity. When the system determines these factors, all available solutions are plotted on graph 1314 as blocks 1312 as shown in FIG. 13.

These values are determined by calculating all container volume and activity pairs at a specified assay time that can meet the given schedule taking into account injection system constraints to produce blocks 1312 on graph 1314.

Figure 18:
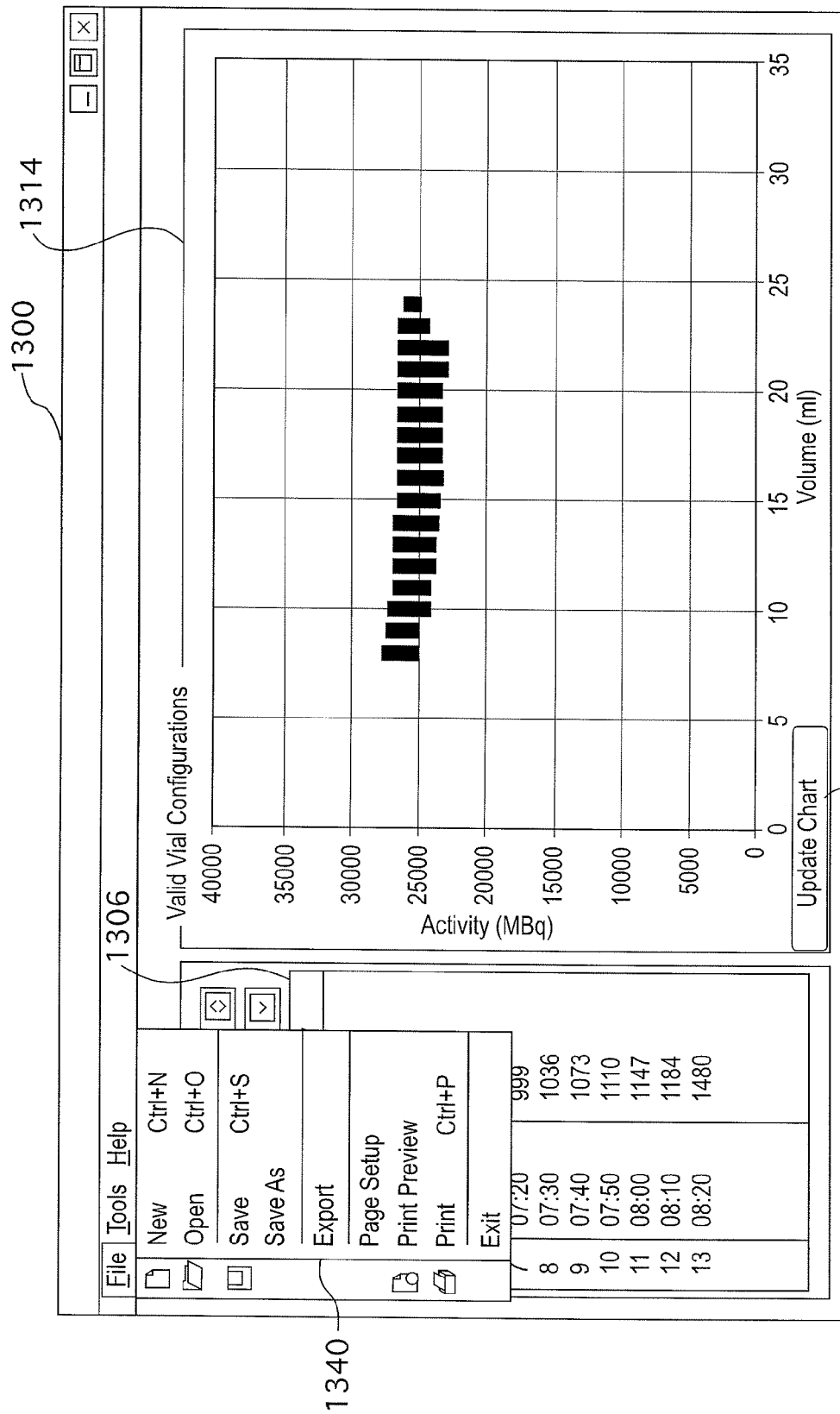

The following system constraints are considered in the model: (1) Prime Volume: volume removed from the container to complete system setup operations that cannot be used for patient dosing; (2) Minimum Dose Volume 1316: the minimum volume of radiopharmaceutical fluid in a single patient dose; (3) Maximum Dose Volume 1318: the maximum volume of radiopharmaceutical fluid in a single patient dose; (4) Unextractable Volume 1320: volume of radiopharmaceutical fluid the system is unable to remove from the container; (5) Maximum Container Activity 1322: maximum activity in a container that can be inserted in the system (separate values may be used for priming 1322a and for patient dosing 1322b); (6) Maximum Container Concentration 1324: maximum activity concentration that is expected from the radiopharmaceutical fluid; (7) Maximum Container Volume 1326: the maximum volume the container can reasonably hold; and (8) Decay Constant: radioactive decay value for the radiopharmaceutical of interest. These values can be adjusted and changed by accessing the options menu 1328 from the tools pull-down menu 1330 as shown in FIG. 18.

Figure 19:
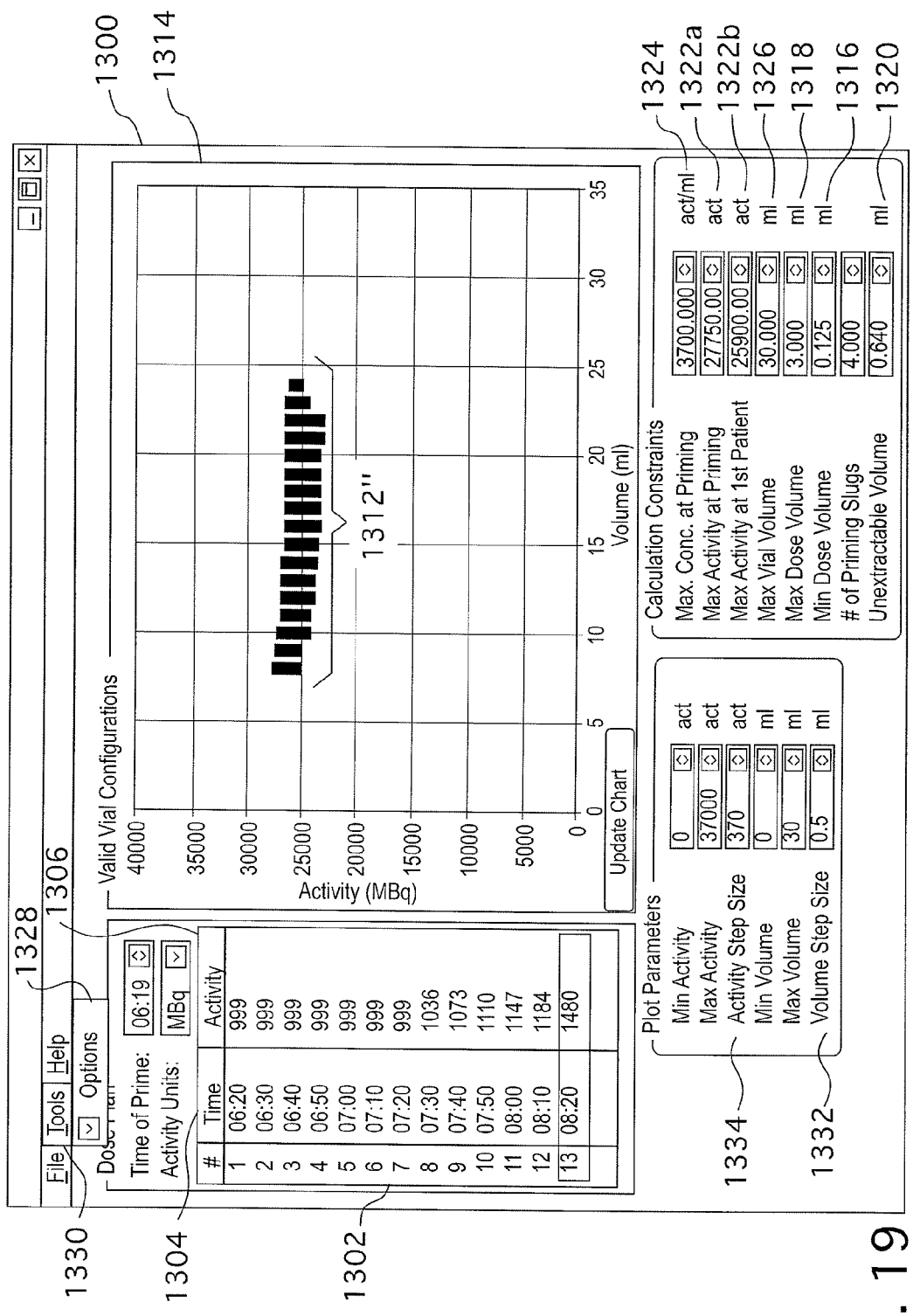
FIGS. 19-26 are various depictions of a graphical user interface for use in injection procedures according to an embodiment.

For the purposes of making calculations tenable, the clinician can provide the system with a prescribed Volume Step 1332 (e.g., 0.5 ml) and Activity Step 1334 (e.g., 10 mCi) that provide reasonable precision with respect to the overall solution space. These values can also be adjusted and changed by accessing the options menu 1328 from the tools pull-down menu 1330 as shown in FIG. 19.

Based on the constraints listed above, it should be clear that only container volumes in the range from Unextractable Volume 1320 to Maximum Container Volume 1326 in increments of Volume Step 1332 need be considered, and container activities in the range from zero to Maximum Container Activity at Priming 1322a, referenced to the given assay time, in increments of Activity Step 1334 need be considered by the system.

Given this operating range constraint, the rules for determining the container activity/container volume pairs as represented by blocks 1312 in FIG. 13 that meet the schedule are as follows:

First, Starting Concentration must be determined as Container Activity divided by Container Volume, referenced by the container assay time. Thereafter, first patient activity is determined as follows: calculating activity remaining after priming by decaying the Starting Concentration to the Planned Injection Time, and calculating activity pursuant to the following equation: (concentration*(Container Volume−Prime Volume)). Then, this activity is decayed to the first patient's Planned Injection Time. Next, the volume required for each patient dose is determined by decaying the Starting Concentration to the Planned Injection Time, then calculating dose volume as Planned Dose/concentration.

The Container Volume/Container Activity pair is considered a valid solution if all the following hold: 1) the Starting Concentration is greater than the Maximum Container Concentration; 2) the Minimum Dose Volume is less than or equal to all dose volumes, which is less than or equal to the Maximum Dose Volume; 3) the difference between the Container Volume and the sum of the Prime Volume and all Dose Volumes is greater than the Unextractable Volume; and 4) the first patient activity is greater than the Maximum Container Activity at the first patient injection.

Figure 14:
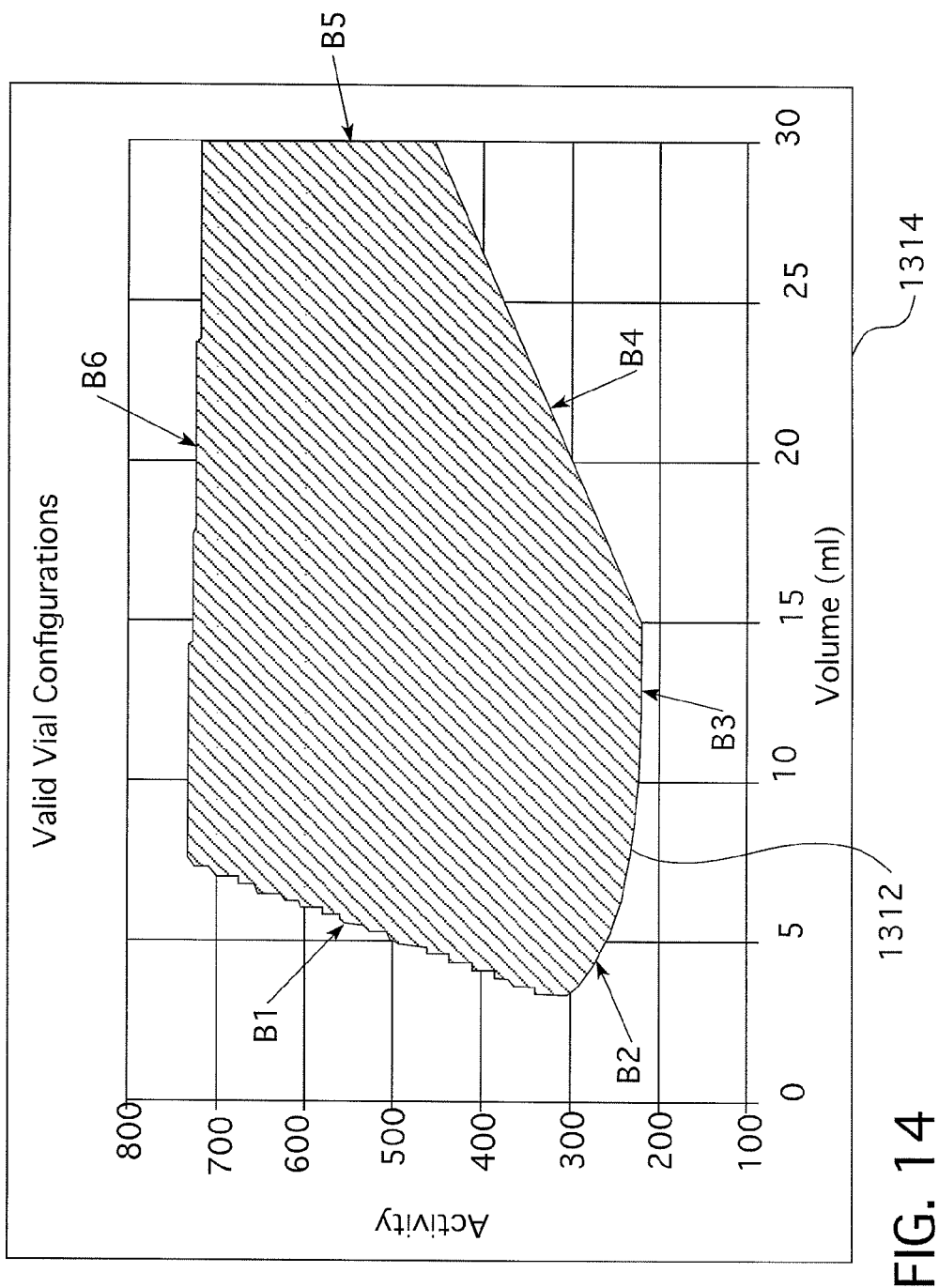

The shaded area provided by block 1312 in FIG. 13 shows the typical solution space from the preceding algorithm for a given patient schedule 1302 and container assay time. With reference to FIG. 14, this solution space is constrained as follows: B1) this boundary represents the highest achievable concentration in the system. The slope of this line is the lesser of: a) the Maximum Container Concentration, and b) First Patient's Planned Dose/Minimum Dose Volume; B2) this boundary represents leaving exactly the Unextractable Volume remaining in the container 902 with the last patient (the last patient dose size is bounded by the remaining extractable volume in the system instead of the absolute Maximum Dose Size); B3) this boundary represents the minimum activity required to meet all scheduled patients and priming without other system constraints taking effect (for container configurations along this boundary, the last patient dose volume will be between the Minimum Dose Volume and Maximum Dose Volume and there will be a small amount of extractable activity left in the container); B4) this boundary represents the minimum concentration limit. The slope of this line is the last patient's Planned Dose/Maximum Dose Volume. For container configurations along this boundary, the last patient dose volume will be the Maximum Dose Volume and there may be a relatively large volume of radiopharmaceutical remaining in the container; B5) this boundary is the Maximum Vial Volume; and B6) this boundary represents absolute maximum vial activity limits. A slope at this boundary appears if there is a higher Maximum Vial Activity at priming than at dosing, and the first patient's Planned Injection Time is very near the Priming Planned Injection Time. Clinicians may choose any solution within the space provided by blocks 1312 to meet their schedule.

Figure 15:
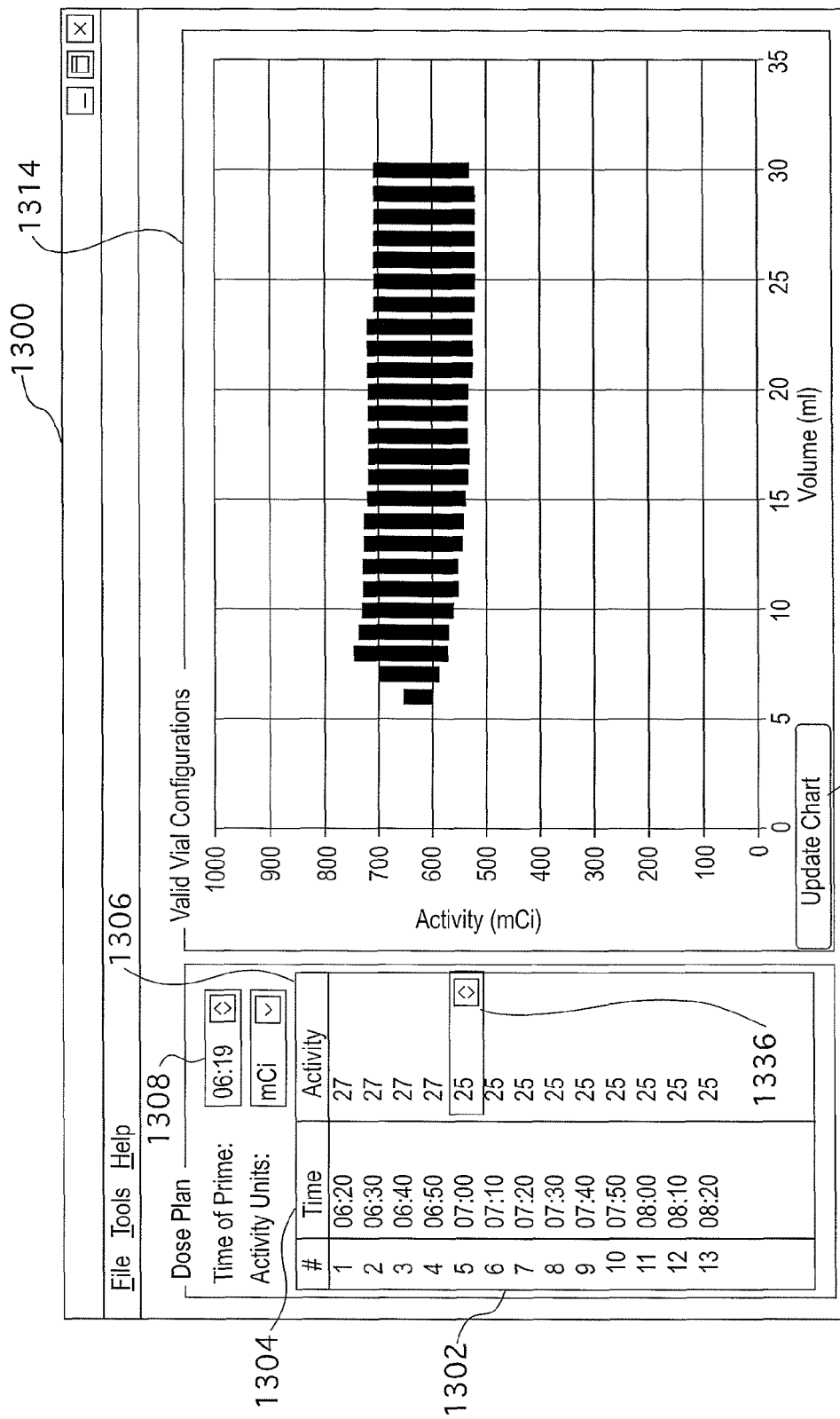
Figure 16:
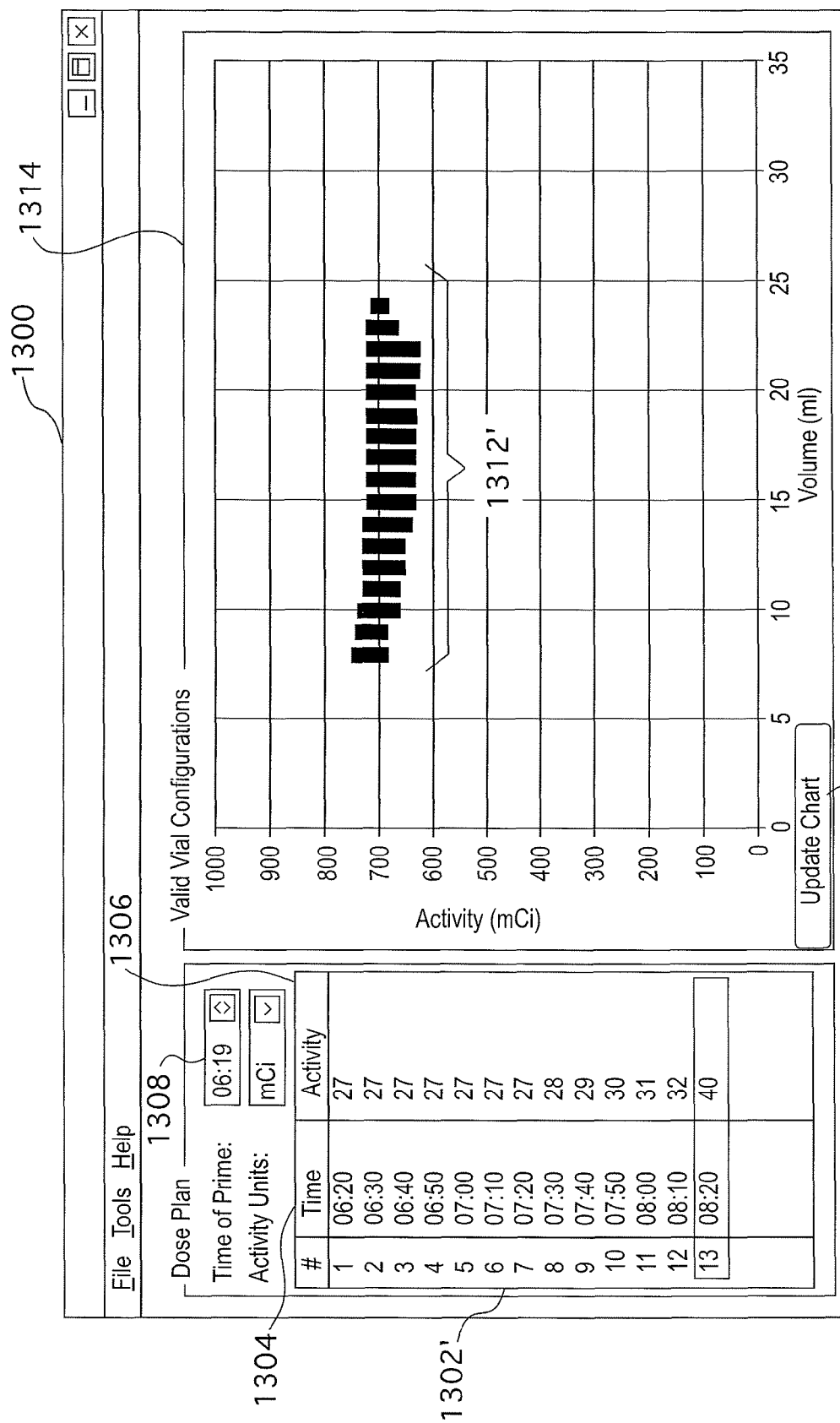

With reference to FIG. 15, the schedule 1302 is editable after being initially provided to accommodate add-on patients, cancellations, time modifications to patients already provided on the planned patient schedule, modifications to an activity removed from the multi-dose container of radiopharmaceutical to patients already provided on the planned patient schedule, or any combination thereof. For instance, a clinician may click on one of the activity values in the schedule 1302 using a mouse or any other suitable input device. A menu 1336 then appears allowing the user to change the activity value for a patient. Once the clinician has completed updating any values in schedule 1302 to produce a new schedule 1302', the update chart button 1310 is pressed and the algorithm discussed hereinabove is run on new schedule 1302' to produce all container volume and activity pairs at a specified assay time that can meet the new schedule 1302' taking into account injection system constraints as represented by blocks 1312' on graph 1314 in FIG. 16.

Figure 17:
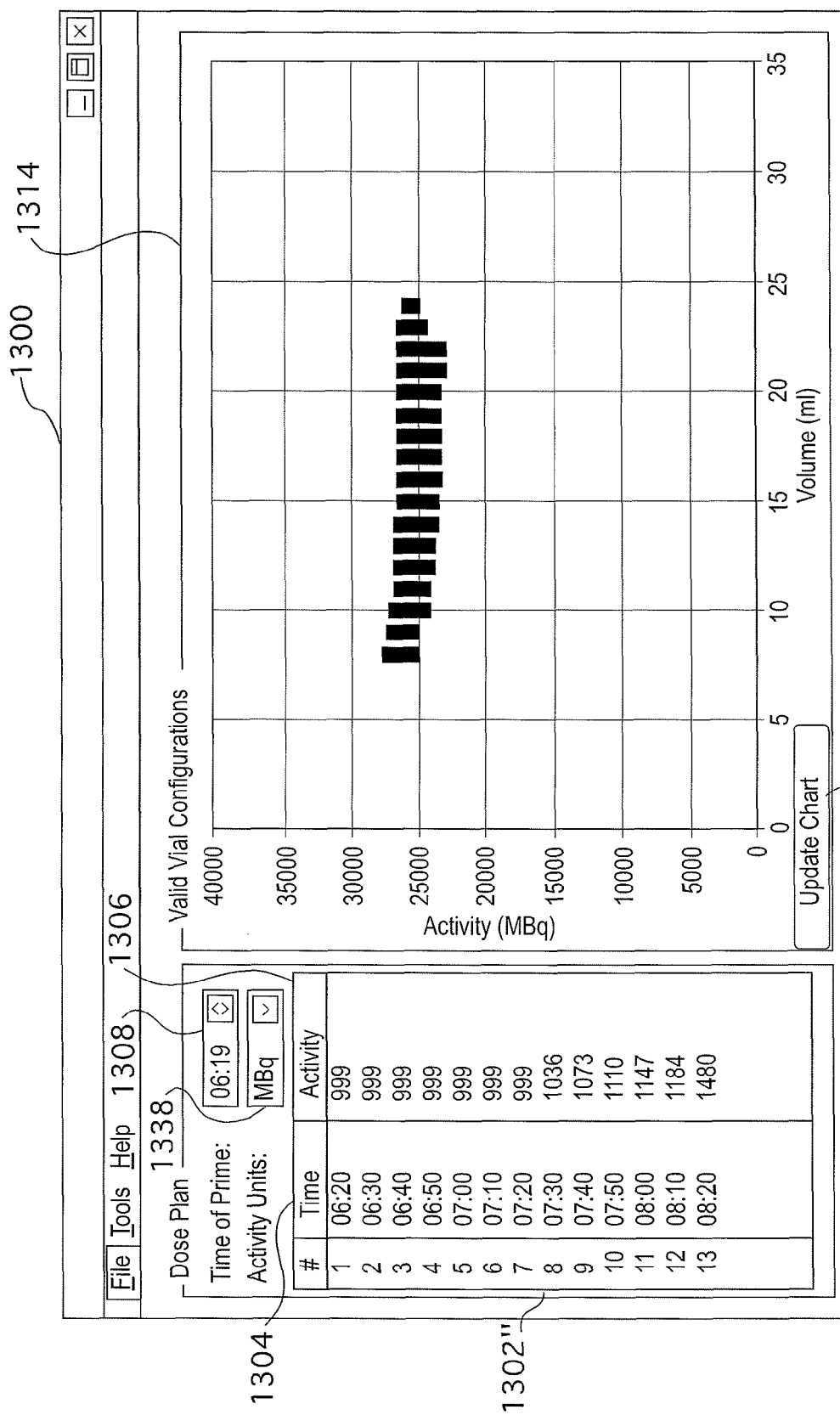

With reference to FIG. 17 activity units may be changed from mCi to MBq using menu 1338 to produce a new schedule 1302" where the activity is measured in MBq. In addition, after the activity units have been changed to MBq, the clinician presses the update chart button 1310 such that the algorithm discussed hereinabove is run on new schedule 1302" to produce all container volume and activity pairs at a specified assay time that can meet the new schedule 1302" taking into account injection system constraints as represented by blocks 1312" on graph 1314 in FIG. 17. The computer 1044 may be coupled to a printer such that a hardcopy (printout) may be generated of both the schedule 1302, 1302', or 1302" and the valid container configuration graph 1314.

With reference to FIG. 18, the schedule 1302,1302', or 1302" may be transferred to a radiopharmaceutical fluid delivery system 10 by selecting the Export button 1340 from the file drop-down menu. This causes the computer 1044 to either save the schedule to a removable memory storage device, such as a flash memory drive, or send the schedule to the fluid delivery system 10 over a network. The clinician then orders the correct multi-dose container configuration and provides the multi-dose container configuration to the radiopharmaceutical fluid delivery system 10 as described hereinabove.

With reference to FIGS. 20-26, a multi-dose container configuration monitoring system that forecasts multi-dose radiopharmaceutical usage over a pending patient schedule and alerts clinicians when there is a risk of not being able to dose the full schedule is described. Shown schematically in FIGS. 20-26 are various incarnations of a touch screen arrangement 1100 displayed on a graphical user interface, such as GUI 15, that could be employed with the fluid delivery system 10. As a non-restrictive example, such a touch screen arrangement could be utilized in conjunction with the system controller 5 of any of a variety of fluid delivery systems as broadly contemplated herein.

In order to clearly and unambiguously communicate to an operator the current status of the fluid delivery system 10, a GUI 15 with easily legible symbols and icons, including exceedingly operator-friendly data entry mechanisms, is broadly contemplated. An operator will thus be able to intuitively understand and undertake various tasks for operating fluid delivery system 10.

While a touch screen arrangement is contemplated in connection with FIGS. 20-26, it is to be understood that other types of data entry arrangements are conceivable that would achieve an equivalent purpose. For example, soft or hard key entry could be used, as well as trackball arrangements, mouse arrangements, or a cursor control touch pad (remote from the screen).

Figure 20:
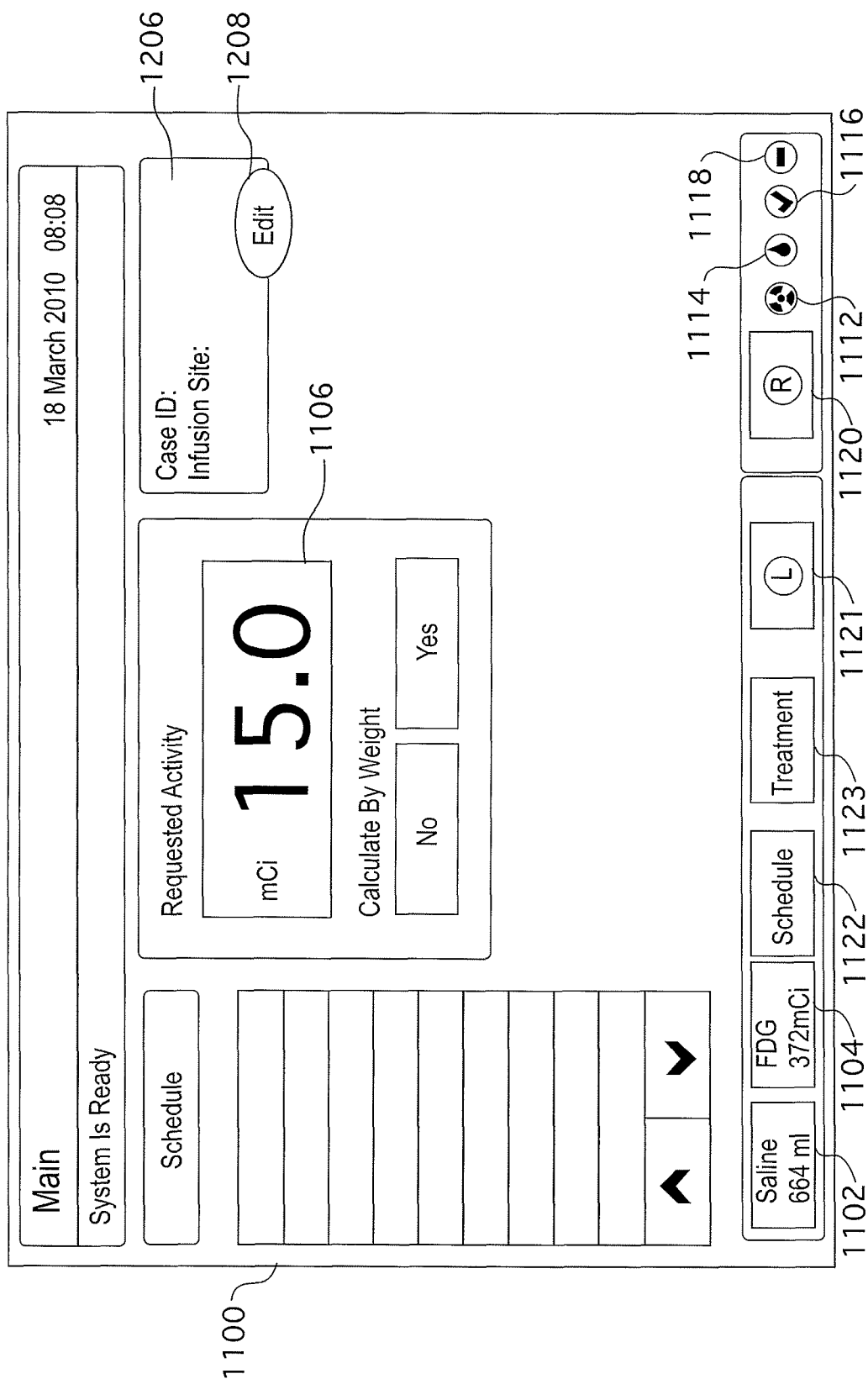

With continued reference to FIG. 20, a main operator interface provided on a touch screen is illustrated before an injection procedure has been started and before a schedule has been transferred thereto. After the operator prepares the system 10 for a fluid delivery procedure, the system 10 generates the display 1100 shown in FIG. 20 which indicates in the upper left hand side thereof that the "System is ready". The touch screen includes a saline field 1102 and a pharmaceutical or FDG field 1104 providing an indication of the amount of saline in source 23 and FDG in container 902, respectively. For example, the saline field 1102 indicates that 664 ml of saline is available and the FDG field 1104 indicates that 372 mCi of FDG are available, as shown. Indicated at 1106 is a touch field showing requested activity (currently displayed as 15.0 mCi) for an injection procedure to be performed. When the system 10 is activated, the requested activity field 1106 may display a default activity value that can be pre-programmed into the system 10 or pre-set by the operator. Alternatively, the requested activity field 1106 can default to the last activity level that was programmed into the system 10.

Indicated at 1112, 1114, 1116, and 1118, respectively, in FIG. 20 are circular status icons that provide quick and easy reference to different aspects of system status and, as such, will highlight when an aspect of system status is "on" or "active", or provide status information on the system 10. Thus, icons 1112-1118 from left to right, respectively, convey information on the following system aspects: activity present 1112, fluid motion/injection status 1114, check for air/priming status 1116, and system battery status 1118.

The system battery (not shown) provides power to the system controller 5 and to the ionization chamber 160 (to maintain the ionization chamber at its normal operating state) in the event that the system 10 is disconnected from an AC power source. The system battery is charged while the system 10 is connected to an AC power source.

FIG. 20 also shows four additional touch fields 1120-1123 along the bottom thereof. Reset button 1120 is activated to reset or clear information, such as case identification information, desired activity level, etc., from the treatment screens. Configuration button 1121 is activated to access the configuration screens for the system 10. Schedule button 1122 is activated to access a scheduling interface to allow an operator to schedule a plurality of injection procedures into the system 10. Treatment button 1123 is activated to access the injection control screen shown in FIG. 19. In addition, the operator can input case information including patient identification and injection site information into the system 10. When the operator activates the edit button 1208 in the case ID field 1206, a "Case Information" pop-up display is provided for inputting a patient or other identification number and an injection site at which the radiopharmaceutical will be administered or injected.

Figure 21:
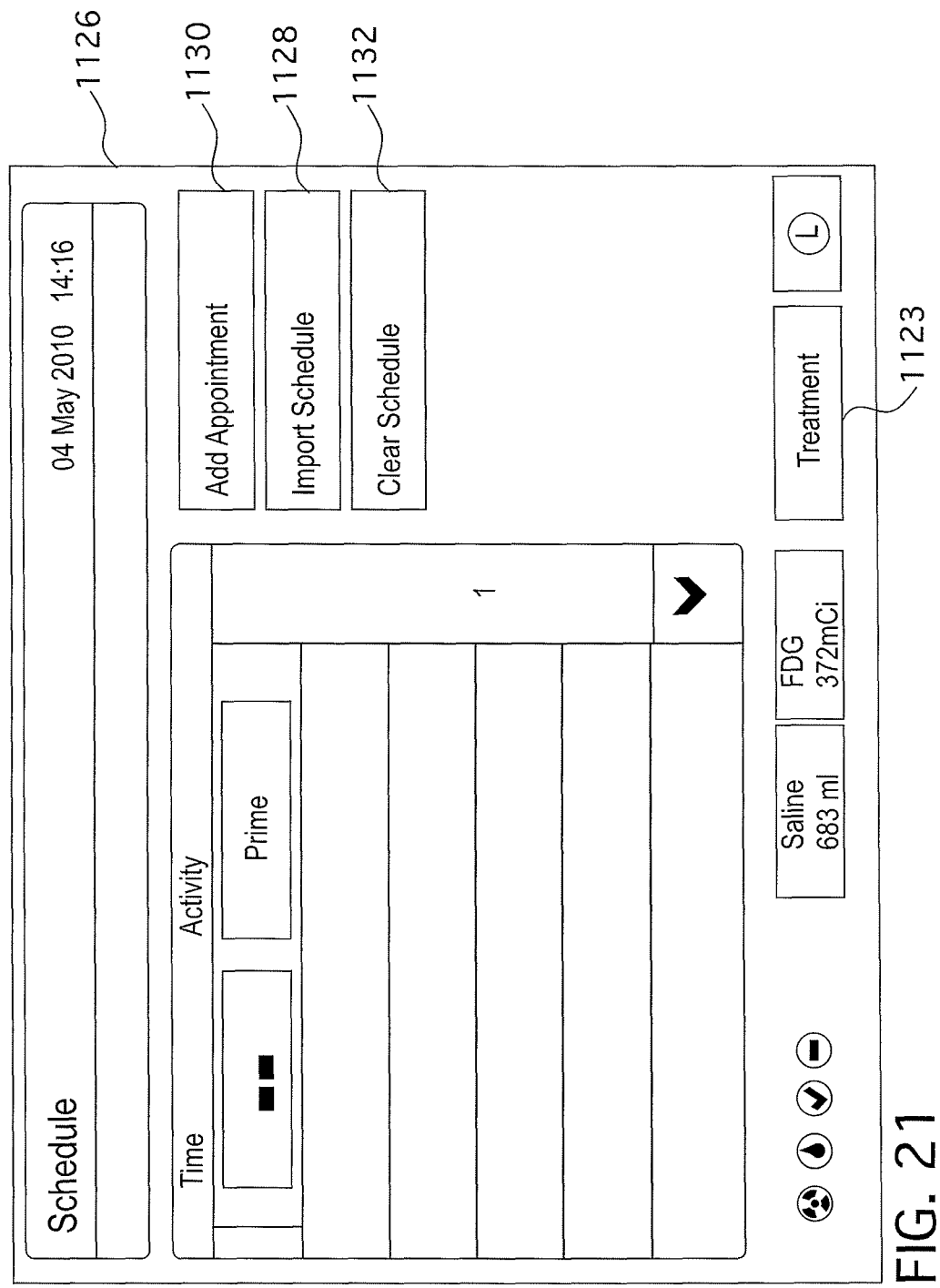
Figure 22:
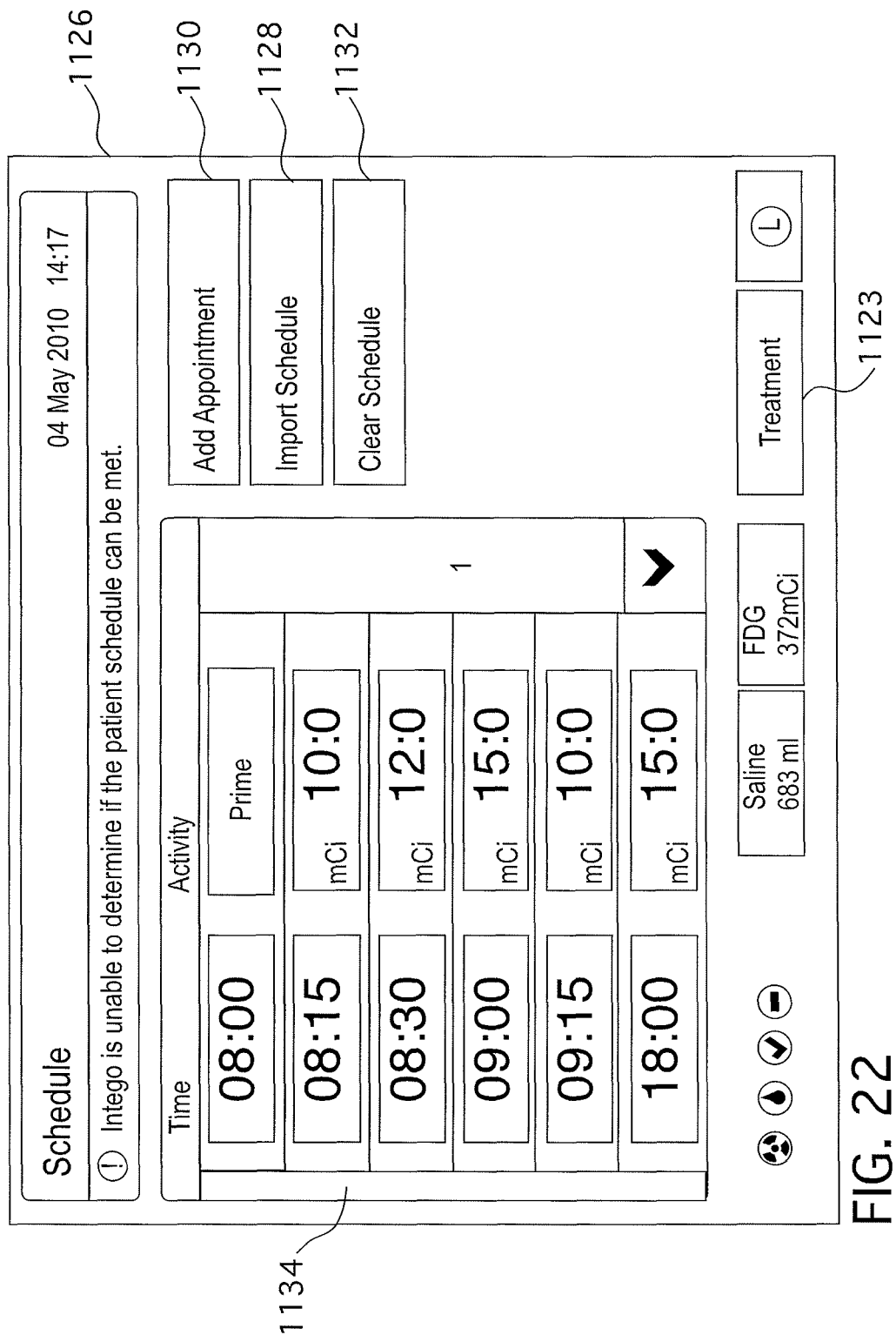
Figure 23:
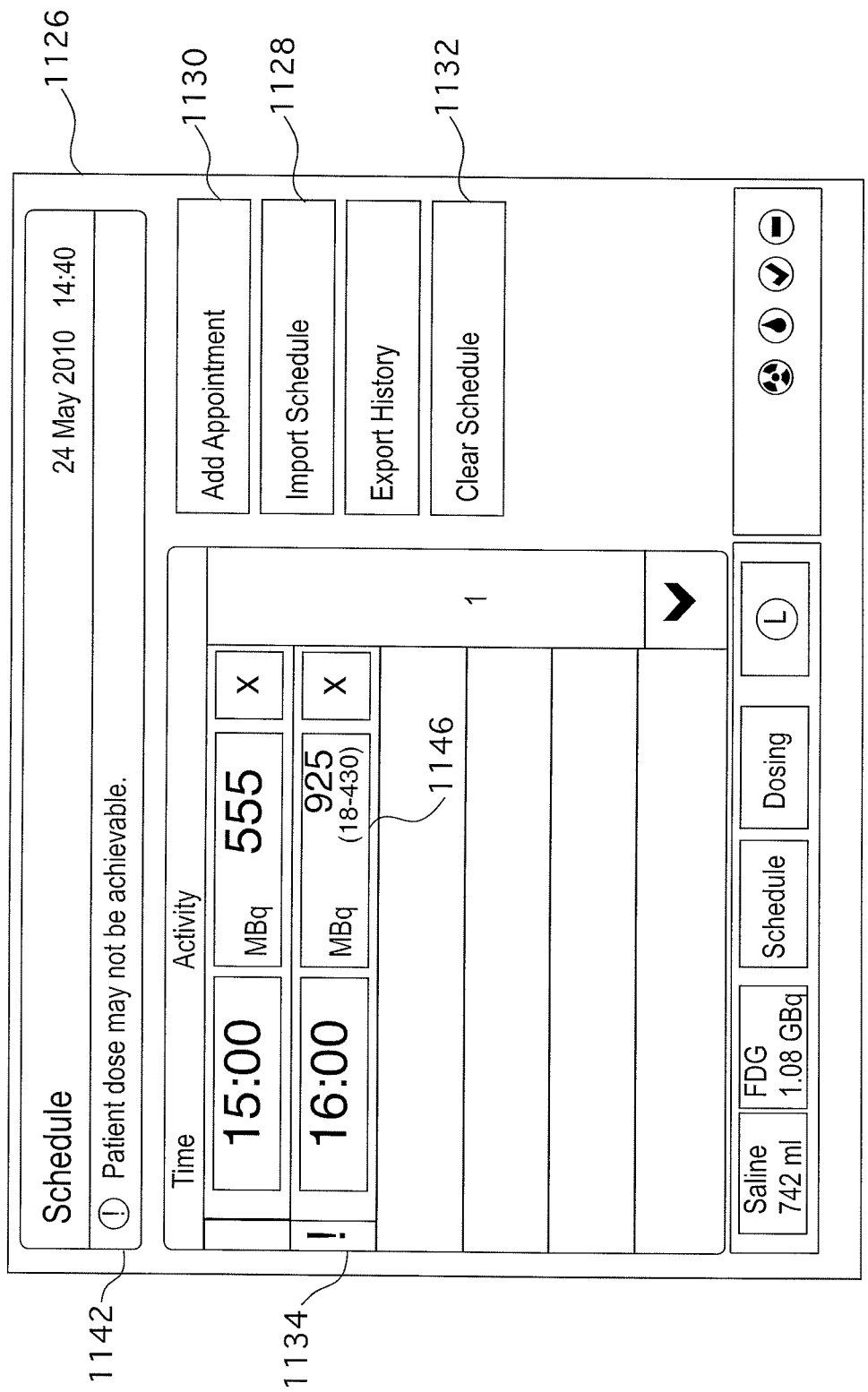

If the operator desires to schedule one or more injection procedures, he activates schedule button 1122, thereby generating pop-up 1126 shown in FIG. 21. At this point, the operator may import a schedule 1302, 1302', or 1302" generated as described hereinabove by pressing the import schedule button 1128. The operator can alter this schedule 1302, 1302', or 1302" or generate a new schedule by pressing the add appointment button 1130. The operator can also clear any schedule that is already in the system 10 by pressing the clear schedule button 1132. Once the schedule is imported, it appears in schedule window 1134. The operator can review the schedule and make any appropriate changes with the add appointment button 1130. Once the operator is satisfied with the schedule, he presses the treatment button 1123 and is returned to a main operating screen 1101 with the schedule pane 1136 populated with the imported schedule as shown in FIG. 22. If for some reason during operation, the system determines that the current multi-dose container configuration will not be able to provide a scheduled patient with the scheduled activity at the scheduled time, the system will provide a warning to the operator in information pane 1142 and highlight the scheduled injection procedure 1144 in the schedule window 1134 as shown in FIG. 23. The system controller 5 may suggest resolutions to the schedule to be able to acceptably infuse the patient which may include adjusting the time of the injection procedure or adjusting the activity of the scheduled does such as by presenting the operator with a range of activity levels 1146 that are available to the patient. For instance, an operator attempted to schedule an injection procedure at 16:00 that required a radiopharmaceutical having an activity level of 925 MBq. If the current multi-dose container configuration is unable to accommodate such an injection procedure, the scheduled injection procedure 1144 is highlighted and a range of activity levels 1146, such as 18-430 MBq, is presented to the operator that would allow the operator to schedule a patient at 16:00. This range represents the Minimum Dose Activity and Maximum Dose Activity achievable for that patient. If this activity level is acceptable to operator, the operator can adjust the injection procedure at 16:00 to have an activity level anywhere between 18-430 MBq. If this level is unacceptable, the operator must cancel the procedure or adjust the infusion time.

The system may also be able to recommend or suggest changes in radioactive dose and/or infusion times for future patients in the schedule collectively to maximize the ability of the system and operator to infuse all of the patients in the schedule. The suggested changes may be for each future patient or for the entire schedule. Any suggested changes in the schedule must be approved by an operator.

Figure 24:
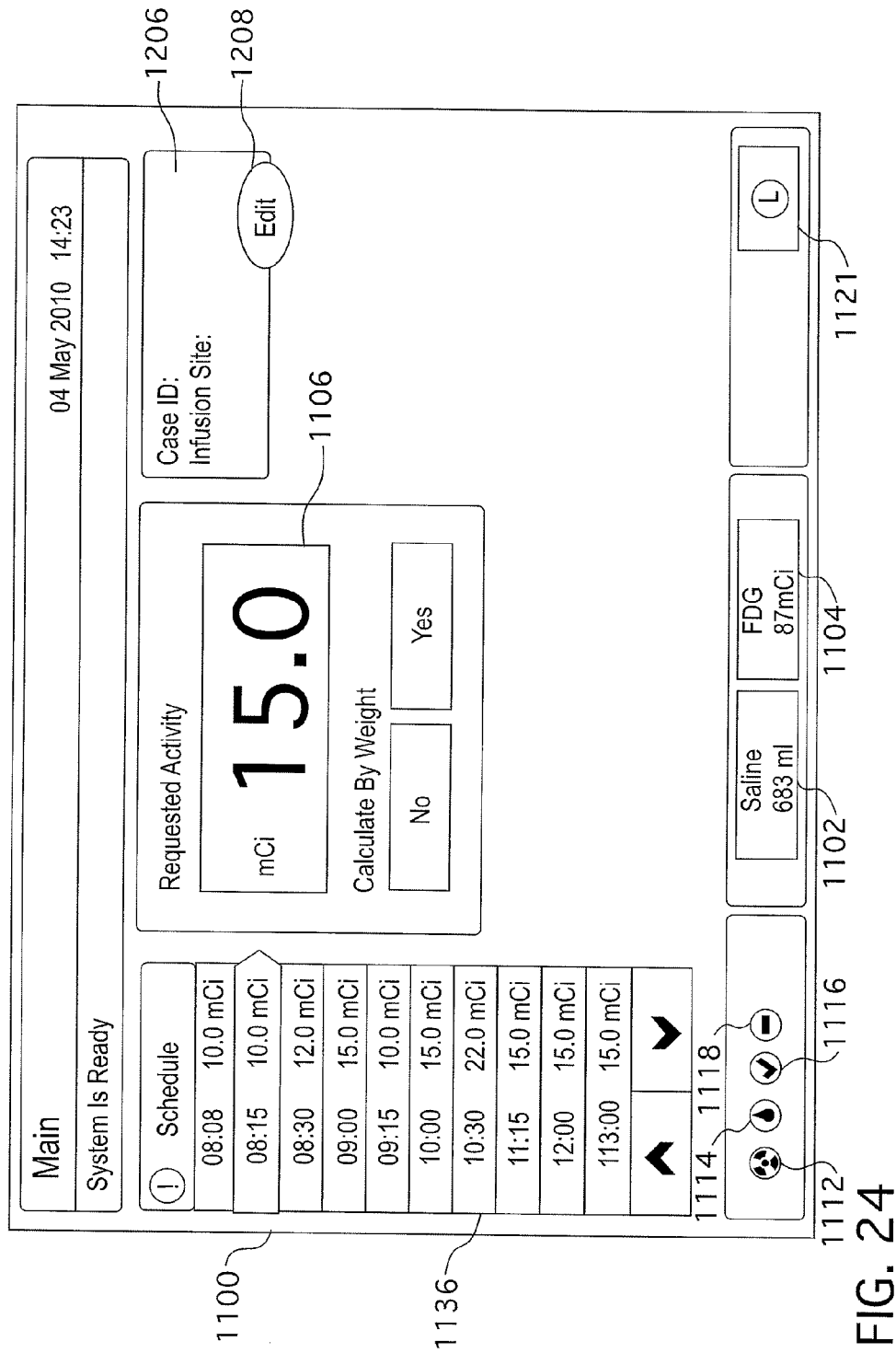

With reference to FIG. 24, the operator, after priming the system as discussed hereinabove, then activates the Infuse button (not shown) to begin the injection procedures provided in the schedule pane 1136.

The system 10 further includes a multi-dose container configuration monitoring system that forecasts multi-dose radiopharmaceutical usage over a pending patient schedule and alerts clinicians when there is a risk of not being able to dose the full schedule. Proper functioning of the monitoring algorithm requires several preconditions to be met. If any of these preconditions are not met, in lieu of forecasting container usage per the schedule the monitor should indicate to the user that it is unable to provide a radiopharmaceutical usage forecast until the precondition has been satisfied.

The preconditions are as follows. First, the monitoring requires, as input, a patient schedule to be imported as discussed hereinabove. The schedule is editable after initial entry to accommodate add-on patients, cancellations, and time/dose modifications to scheduled patients. For the monitor to work properly, the operator must have scheduled priming entry and times/doses scheduled for all patients.

The next precondition is that the monitor requires an estimate of the remaining extractable radiopharmaceutical activity and volume at the present time. This is typically based on the original multi-dose container assay information, less fluid removed from the multi-dose container, and adjusted for unextractable volume and isotope decay. An activity monitoring device, such as an ionization chamber, a CZT crystal detector, a Geiger-Müller counter, or a scintillating counter, may be used to determine this information.

The third precondition comes from the fact that the monitor algorithm is intended to forecast dosing for future patients. It is feasible for one patient to be past due, in which case the monitor can realistically associate that patient with the current time. However, reliable forecasting is not possible if more than one patient is past due. Accordingly, the monitor requires that no more than one patient pending dosing is scheduled in the past.

If all preconditions are met, the monitor uses the following algorithm to determine if a given patient schedule can be met. The monitor uses the same system constraints discussed hereinabove, as well as: 1) Extractable Volume: volume remaining in the multi-dose container available for dosing (it is the total volume remaining in the multi-dose container less the Unextractable Volume); and 2) Extractable Activity: activity remaining in the multi-dose container available for dosing. Given these parameters, the monitor will determine the viability of meeting the given schedule with the multi-dose container per the following algorithm: 1) establish initial parameter values such as, Start Concentration and Start Time; and 2) for each item in the schedule that has not yet been executed (e.g., priming, undosed patients), take the following action in order according to scheduled injection time: 2.1) set Delta Time to the higher of the difference between the scheduled injection time and the start time or zero; 2.2) set the Current Concentration by decaying the Start Concentration by Delta Time; 2.3) for patient items, set Dose Activity to the Planned Dose and for priming items, set the Dose Activity to Prime Volume multiplied by the Current Concentration; 2.4) for patient items, calculate Dose Volume as Dose Activity divided by Current Concentration, and for priming items, set the Dose Volume to the Prime Volume; 2.5) calculate the Maximum Dose Activity as Current Concentration multiplied by the lesser of Maximum Dose Volume or Extractable Volume; 2.6) calculate the Minimum Dose Activity as Minimum Dose Volume multiplied by Current Concentration; and 2.7) if any of the following are true, mark the current and all subsequent items in the schedule as at risk for dosing with the current multi-dose container 902:

a. Dose Activity less than Minimum Dose Activity; and b. Dose Activity greater than Maximum Dose Activity.

If the step 2.7 determined that the scheduled item was at risk, the processing must be halted and the operator must be notified. Otherwise, parameters for processing the next item in the schedule are updated by updating Extractable Volume by subtracting from it the Dose Volume.

Figure 25:
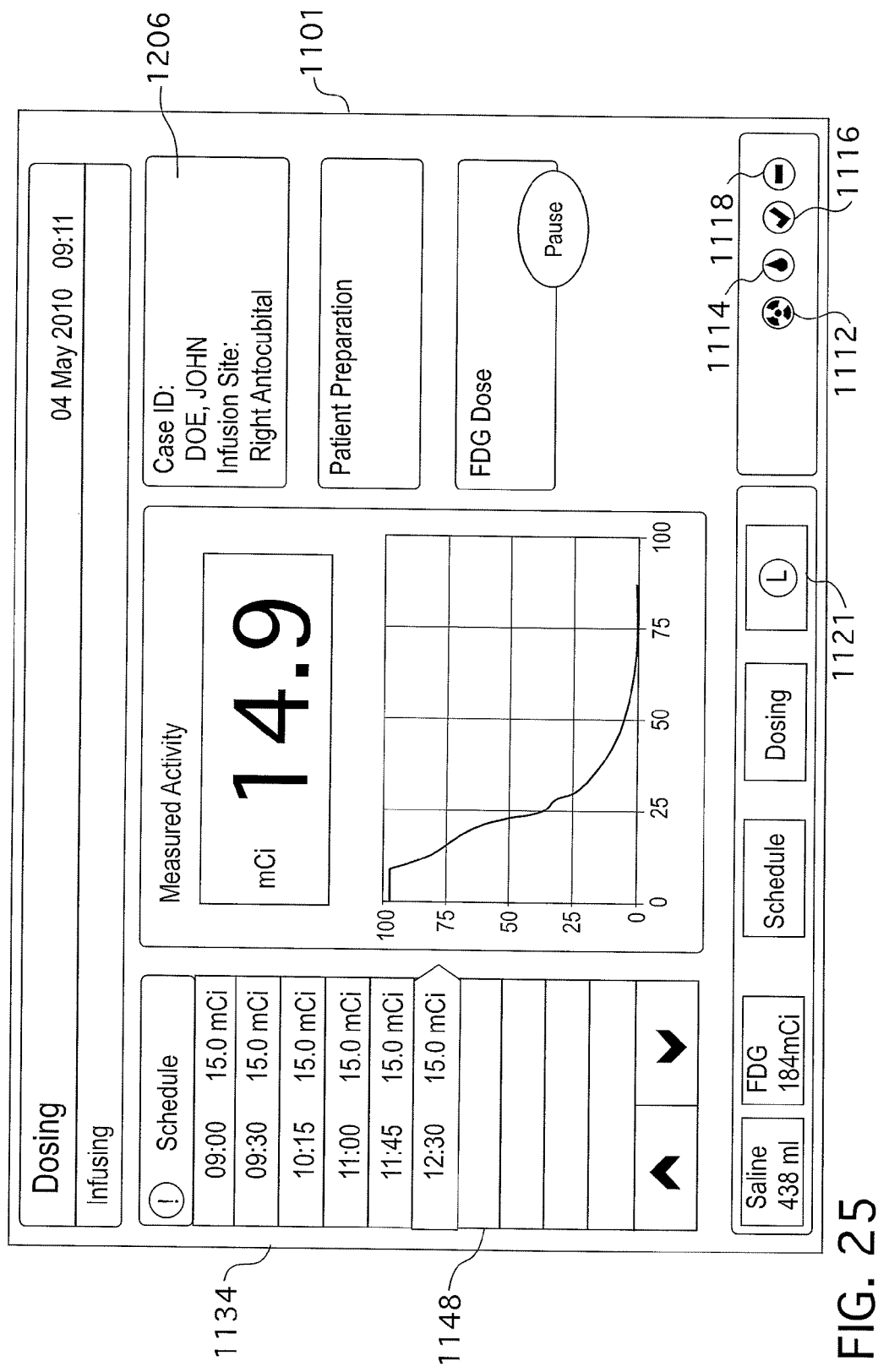

The items in the schedule may be marked by highlighting the items within the schedule pane 1136 as shown in FIG. 25 by reference numeral 38 to alert the operator action is likely required on their part. Furthermore, the first at risk item in the schedule should present the Minimum Dose Activity and Maximum Dose Activity achievable for that patient, thereby giving the operator sufficient information to determine the best course of action for this item. For example, the clinician may elect to dose the patient with the current container 902 even if the patient is at risk if the shortfall is still within acceptable dosing limits.

Figure 26:
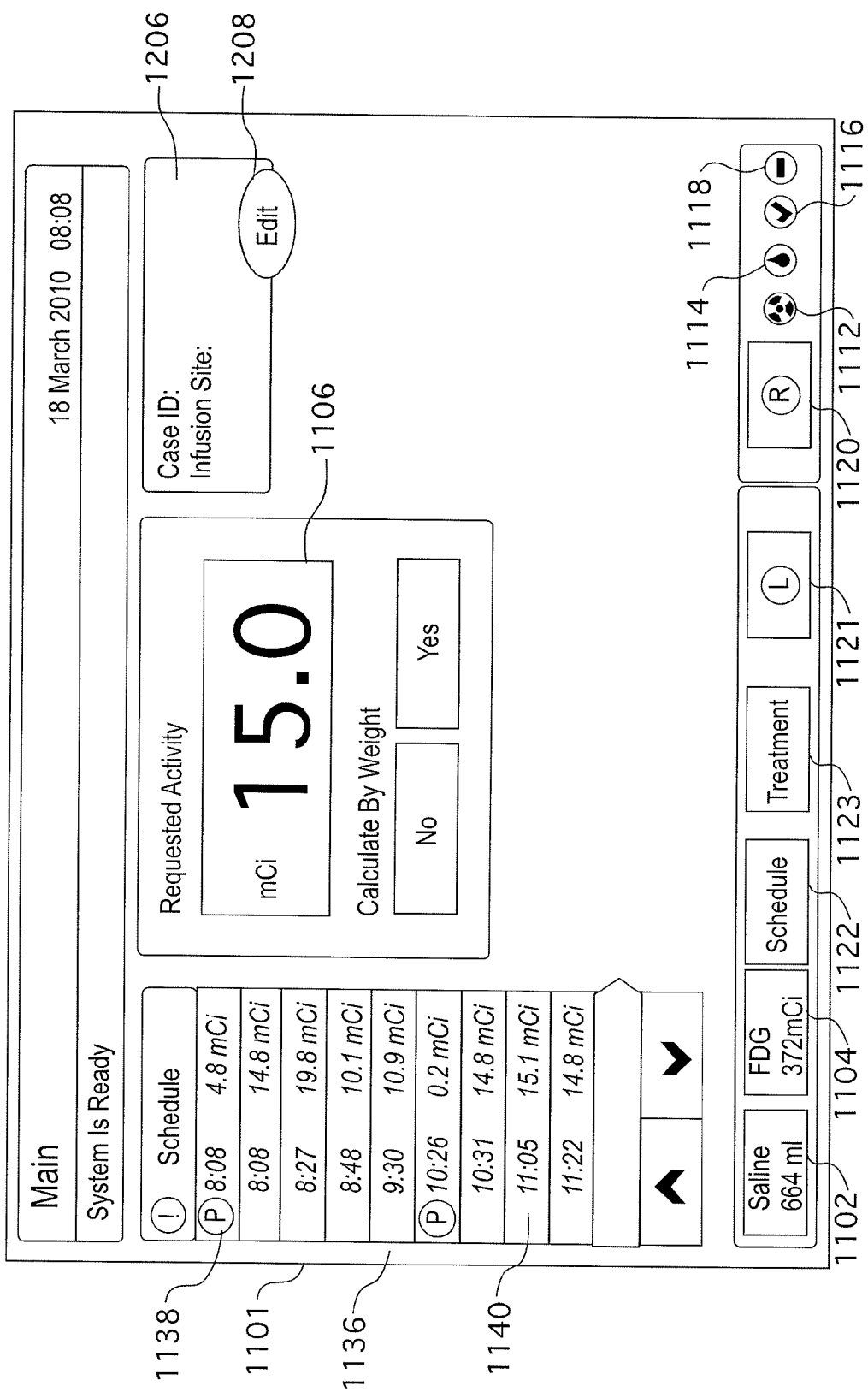

In addition, as items are completed, the schedule is updated with actual injection times and doses. This provides the clinician with a history of injections performed with the current container. In addition, an icon, such as a green check mark 1140 for a completed injection procedure and a yellow P 1138 for a partial injection procedure, may be placed next to each item in the schedule in the schedule pane 1136 as shown in FIG. 26.

The main objective of the planning and monitoring of multi-dose pharmaceutical procedures is to optimize a schedule of injection procedures to minimize the amount of radiopharmaceutical that is wasted and maximize the number of injection procedures that are performed with a given radiopharmaceutical configuration. Accordingly, the system utilizes a two step procedure to achieve this objective. First, an operator loads a schedule of injection procedures into the system that includes a time and a required activity level for each of the procedures and provides a user with a plurality of multi-dose radiopharmaceutical container configurations that can be used to meet his needs as discussed hereinabove with reference to FIGS. 12-19. Along with the time and required activity level for each of the injection procedures, the system may also consider at least one of the following factors in determining the plurality of multi-dose radiopharmaceutical container configurations that are presented to the user: 1) delivery logistics; 2) distance from the radiopharmaceutical production facility; 3) container size; 4) flexibility of the radiopharmaceutical; 5) production schedule of the radiopharmaceutical production facility; 6) injection system loses (e.g., waste, priming, etc.); and 7) radiopharmaceutical half-life. However, these factors are not to be construed as limiting the present disclosure as the system may also consider a variety of other factors may need to be considered in this determination. Thereafter, the operator selects an appropriate multi-dose radiopharmaceutical container configuration and begins the scheduled injection procedures.

The second step of the procedure is if the schedule changes during the injection procedures, the system then recommends a new schedule that optimizes the number of patient scans and/or injections that can be performed by suggesting changes in the radioactive dose and/or the infusions times for each future patient or for the entire schedule. This maximizes the system's ability to infuse all of the patients in the schedule and minimizes radiopharmaceutical waste.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

What is claimed is:

1. A method of planning and monitoring radiopharmaceutical usage, the method comprising:
    receiving a patient schedule for a plurality of radiopharmaceutical injection procedures;
    based on the patient schedule, determining a multi-dose container configuration for use during the plurality of radiopharmaceutical injection procedures;
    wirelessly transferring the patient schedule to a radiopharmaceutical fluid delivery system;
    wirelessly providing the multi-dose container configuration to the radiopharmaceutical fluid delivery system;
    conducting the plurality of radiopharmaceutical injection procedures based on the patient schedule;
    wirelessly monitoring the multi-dose container configuration during the plurality of radiopharmaceutical injection procedures;
    determining whether there is a risk that at least one of the plurality of radiopharmaceutical injection procedures may not be completed properly due to one or more patient schedule changes; and
    providing an alert in response to the risk being determined.

2. The method of claim 1, wherein the patient schedule comprises, for each of a plurality of patients, a time of a radiopharmaceutical injection procedure for a patient and an activity of radiopharmaceutical to be removed from the multi-dose container configuration for the patient.

3. The method of claim 1, wherein the multi-dose container configuration includes a plurality of multi-dose containers each holding a different radiopharmaceutical fluid.

4. The method of claim 1, further comprising:
    editing the patient schedule after providing the multi-dose container configuration to accommodate one or more patient schedule changes selected from the group consisting of an additional patient, a cancelled patient, a time modification for a patient on the patient schedule, and a modification to an activity of radiopharmaceutical to be removed from the multi-dose container configuration for a patient on the patient schedule.

5. The method of claim 1, wherein wirelessly monitoring the multi-dose container configuration comprises:
    determining a remaining activity and volume of radiopharmaceutical in the multi-dose container configuration to provide a remaining activity estimation; and
    adjusting the remaining activity estimation based on isotope decay.

6. The method of claim 1, further comprising:
    updating the patient schedule to accommodate a maximum number of the plurality of radiopharmaceutical injection procedures in response to the risk being determined.

7. The method of claim 1, further comprising:
    displaying the patient schedule on a graphical user interface of the radiopharmaceutical fluid delivery system.

8. The method of claim 7, wherein the graphical user interface is a wireless touch-screen.

9. An article comprising a non-transitory machine-readable storage medium comprising instructions that, if executed, enable a processor to:
    receive a patient schedule of a plurality of radiopharmaceutical injection procedures;
    based on the patient schedule, determine a multi-dose container configuration for use during the plurality of radiopharmaceutical injection procedures;
    monitor the multi-dose container configuration during the plurality of radiopharmaceutical injection procedures;
    determine whether there is a risk that at least one of the plurality of radiopharmaceutical injection procedures may not be completed properly due to one or more patient schedule changes; and
    provide an alert in response to the risk being determined, wherein at least a portion of the instructions are transmitted by a wireless network.

10. The article of claim 9, wherein the non-transitory machine-readable storage medium further comprises instructions that, if executed, enable the processor to wirelessly transfer the patient schedule to a radiopharmaceutical fluid delivery system.

11. The article of claim 9, wherein the patient schedule comprises, for each of a plurality of patients:
    a time of an injection procedure for a patient; and
    an activity of radiopharmaceutical removed from the multi-dose container configuration for the patient.

12. The article of claim 11, wherein the instructions that, if executed, enable the processor to receive the patient schedule enable the processor to perform at least one step selected from the group consisting of:

wirelessly receive the time of the injection procedure and the activity of radiopharmaceutical for the patient from a user via a computer;

wirelessly receive the time of the injection procedure and the activity of radiopharmaceutical for the patient from a memory device associated with the computer; and wirelessly receive the time of the injection procedure and the activity of radiopharmaceutical for the patient from a remotely located patient device over a network.

13. The article of claim 9, wherein the non-transitory machine-readable storage medium further comprises instructions that, if executed, enable the processor to edit the patient schedule after providing the multi-dose container configuration to accommodate one or more patient schedule changes selected from the group consisting of an additional patient, a cancelled patient, a time modification for a patient on the patient schedule, and a modification to an activity of radiopharmaceutical to be removed from the multi-dose container configuration for a patient on the patient schedule.

14. The article of claim 9, wherein the multi-dose container configuration includes a plurality of multi-dose containers each holding a different radiopharmaceutical fluid.

15. A planning and monitoring software stored on a non-transitory_storage medium to plan and monitor radiopharmaceutical usage, the software comprising programming instructions that, if executed, enable a processor to wirelessly:

receive a patient schedule of a plurality of radiopharmaceutical injection procedures;

based on the patient schedule, determine a multi-dose container configuration for use during the plurality of radiopharmaceutical injection procedures;

monitor the multi-dose container configuration during the plurality of radiopharmaceutical injection procedures;

determine whether there is a risk that at least one of the plurality of radiopharmaceutical injection procedures may not be completed properly due to one or more patient schedule changes; and provide an alert in response to the risk being determined.

16. The planning and monitoring software of claim 15, wherein the software comprises further programming instructions that, if executed, enable the processor to transfer the patient schedule to a radiopharmaceutical fluid delivery system.

17. A radiopharmaceutical fluid delivery device comprising:

a radiopharmaceutical source comprising a multi-dose container;

a disposable administration set configured to allow fluid flow from the radiopharmaceutical source to a patient;

a pumping mechanism in operative communication with the disposable administration set and the radiopharmaceutical source, and configured to pump fluid from the radiopharmaceutical source through the disposable administration set to the patient;

a control unit operatively coupled to the pumping mechanism, and configured to wirelessly receive a patient schedule, determine a multi-dose container configuration for use during a plurality of radiopharmaceutical injection procedures, control the pumping mechanism to conduct the plurality of radiopharmaceutical injection procedures based on the patient schedule, monitor the multi-dose container configuration during the plurality of radiopharmaceutical injection procedures, determine whether there is a risk that at least one of the plurality of radiopharmaceutical injection procedures may not be completed properly due to one or more patient schedule changes, and provide an alert in response to the risk being determined; and a display unit wirelessly coupled to the control unit for displaying the patient schedule.

18. The radiopharmaceutical fluid delivery system of claim 17, wherein the multi-dose container configuration comprises a plurality of multi-dose containers each holding a different radiopharmaceutical fluid.

* * * * *

UNITED STATES PATENT AND TRADEMARK OFFICE
CERTIFICATE OF CORRECTION

PATENT NO. : 9,463,335 B2
APPLICATION NO. : 14/826602
DATED : October 11, 2016
INVENTOR(S) : Griffith et al.

Page 1 of 1

It is certified that error appears in the above-identified patent and that said Letters Patent is hereby corrected as shown below:

In the Drawings
In Fig. 4A, Sheet 12 of 33, delete Tag "50b" and insert -- 506 --, therefor.

In the Claims
In Column 33, Line 24, in Claim 15, delete "non-transitory_storage" and insert -- non-transitory storage --, therefor.

Signed and Sealed this
Third Day of January, 2017

Michelle K. Lee
*Director of the United States Patent and Trademark Office*